United States Patent
Raheja et al.

(10) Patent No.: US 11,306,111 B2
(45) Date of Patent: Apr. 19, 2022

(54) ORGANOPHOSPHATE DERIVATIVES

(71) Applicant: January Therapeutics, Inc., San Diego, CA (US)

(72) Inventors: Raj Raheja, San Diego, CA (US); Robin M. Jackman, San Diego, CA (US)

(73) Assignee: JANUARY THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 16/635,469

(22) PCT Filed: Jul. 30, 2018

(86) PCT No.: PCT/US2018/044389
§ 371 (c)(1),
(2) Date: Jan. 30, 2020

(87) PCT Pub. No.: WO2019/027905
PCT Pub. Date: Feb. 7, 2019

(65) Prior Publication Data
US 2020/0369695 A1 Nov. 26, 2020

Related U.S. Application Data

(60) Provisional application No. 62/637,960, filed on Mar. 2, 2018, provisional application No. 62/538,879, filed on Jul. 31, 2017.

(51) Int. Cl.
| | | |
|---|---|---|
| *A61P 31/00* | (2006.01) | |
| *A61P 35/00* | (2006.01) | |
| *C07F 9/6574* | (2006.01) | |
| *C07F 9/6558* | (2006.01) | |

(52) U.S. Cl.
CPC .......... *C07F 9/65586* (2013.01); *A61P 35/00* (2018.01); *C07F 9/65744* (2013.01)

(58) Field of Classification Search
CPC ........ C07F 9/65744; A61P 31/00; A61P 35/00
See application file for complete search history.

(56) References Cited

U.S. PATENT DOCUMENTS

| | | |
|---|---|---|
| 10,071,084 B2 | 9/2018 | Lee et al. |
| 2010/0160249 A1 | 6/2010 | Couvreur et al. |
| 2012/0328701 A1 | 12/2012 | Edelson et al. |
| 2013/0131008 A1 | 5/2013 | Cui et al. |
| 2014/0128339 A1 | 5/2014 | Girijavallabhan et al. |
| 2014/0199404 A1 | 7/2014 | Heise |
| 2015/0105341 A1 | 4/2015 | Beigelman et al. |
| 2018/0155385 A1 | 6/2018 | Dousson et al. |
| 2018/0289620 A1 | 10/2018 | Desai et al. |
| 2021/0007999 A1 | 1/2021 | Raheja et al. |
| 2021/0038628 A1 | 2/2021 | Raheja et al. |
| 2021/0047358 A1 | 2/2021 | Raheha et al. |

FOREIGN PATENT DOCUMENTS

| | | | |
|---|---|---|---|
| CN | 101061131 A | 10/2007 | |
| CN | 103239733 A | 8/2013 | |
| CN | 101732258 B | 12/2013 | |
| CN | 104961786 A | 10/2015 | |
| CN | 106573011 A | 4/2017 | |
| CN | 107148423 A | 9/2017 | |
| EP | 3214090 A1 | 9/2017 | |
| TW | 201700492 A | 1/2017 | |
| WO | WO-2007022073 A2 | 2/2007 | |
| WO | WO-2013096679 A1 | 6/2013 | |
| WO | WO-2014138278 A1 | 9/2014 | |
| WO | WO-2015134334 A1 * | 9/2015 | ............. A61P 31/18 |
| WO | WO-2016068341 A1 | 5/2016 | |
| WO | WO-2016188943 A1 | 12/2016 | |
| WO | WO-2017120537 A1 | 7/2017 | |
| WO | WO-2019027905 A1 | 2/2019 | |
| WO | WO-2019169323 A1 | 9/2019 | |
| WO | WO-2019169324 A1 | 9/2019 | |
| WO | WO-2020041050 A1 | 2/2020 | |
| WO | WO-2020041051 A1 | 2/2020 | |
| WO | WO-2020223530 A1 | 11/2020 | |
| WO | WO-2021030472 A1 | 2/2021 | |

OTHER PUBLICATIONS

Golub et al., Science, vol. 286, Oct. 15, 1999, pp. 531-537. (Year: 1999).*
Bundgaard. Chapter 5: Design and Application of Prodrugs. A Textbook of Drug Design and Development. (pp. 113-191) (1991).
Bundgaard. Design of Prodrugs. Elsevier. Chapter 1. pp. 1-3 (1985).
Bundgaard. Means to Enhance Penetration: Prodrugs as a Means to Improve the Delivery of Peptide Drugs. Advanced Drug Delivery Review 8:1-38 (1992).
Bundgard, H. Design of Prodrugs. 1985; pp. 7-9, 21-24 (Elsevier, Amsterdam).
Lee et al. Synthesis and characterization of positive-charge functionalized mesoporous silica nanoparticles for oral drug delivery of an anti-inflammatory drug. Advanced Functional Materials 18:3283-3292 (2008).
Meier et al. Chapter 15: The cycloSal-Nucleotide Delivery System, pp. 353-401, Peters, Godefridus J., ed. Deoxynucleoside analogs in cancer therapy. Springer Science & Business Media (2007).
Meng et al. Use of a lipid-coated mesoporous silica nanoparticle platform for synergistic gemcitabine and paclitaxel delivery to human pancreatic cancer in mice. ACS NANO 9(4):3540-3557 (2015).
PCT/US2019/020389 International Search Report and Written Opinion dated Jul. 9, 2019.
PCT/US2019/020389 Invitation to Pay Additional Fees dated May 2, 2019.

(Continued)

*Primary Examiner* — Laura L Stockton
(74) *Attorney, Agent, or Firm* — Wilson Sonsini Goodrich & Rosati

(57) ABSTRACT

Provided herein are organophosphates and pharmaceutical compositions comprising said compounds.

19 Claims, No Drawings

(56) References Cited

OTHER PUBLICATIONS

PCT/US2019/020391 International Search Report and Written Opinion dated May 14, 2019.
PCT/US2020/045985 International Search Report and Written Opinion dated Nov. 24, 2020.
U.S. Appl. No. 16/992,036 Office Action dated Apr. 6, 2021.
U.S. Appl. No. 16/992,036 Office Action dated Dec. 1, 2020.
Widder et al. Section III: Prodrugs Kinetics. Method in Enzymology. 112:309-396 (1985).
Yu et al. An in vitro and in vivo study of gemcitabine-loaded albumin nanoparticles in a pancreatic cancer cell line. Int J Nanomedicine. 10:6825-6834 (2015).
Berge et al. Pharmaceutical Salts. Journal of Pharmaceutical Sciences 66(1):1-19 (Jan. 1977).
PCT/US2018044389 Invitation to Pay Additional Fees dated Oct. 2, 2018.
PCT/US2018/44389 International Search Report and Written Opinion dated Nov. 29, 2018.
Choudhuri et al. Chain-length dependence of lipophilic force: comparison with the two-body van der Waals' force J. Phys. Condens. Matter 30:355002 (2018).
Golub et al., Molecular classification of cancer: class discovery and class prediction by gene expression monitoring. Science. 286(5439):531-537 (1999).
Green et al. Abraxane®, a novel Cremophor®-free, albumin-bound particle form of paclitaxel for the treatment of advanced non-small-cell lung cancer. Ann Onc 17(8):1263-1268 (2006).
Lansakara et al. Synthesis and in vitro evaluation of novel lipophilic monophosphorylated gemcitabine derivatives and their nanoparticles. Int J Pharm 429(1-2):123-34 (2012).
Li et al. Experimental study on treatment of pancreatic cancer with gemcitabine albumin nanoparticles and arterial perfusion of pancreas. Chinese Doctoral Dissertations Full-text Database, Medicine and Health Sciences pp. E072-E078 (2015).
Park et al. The roles of short and long chain fatty acids on physicochemical properties and improved cancer targeting of albumin-based fattigation-platform nanoparticles containing doxorubicin. Intl J Pharm 564:124-135 (2019).
Qi et al. Enhanced Antitumor Activity of Monophosphate Ester Prodrugs of Gemcitabine: In Vitro and In Vivo Evaluation. J Pharm Sci 105(9):2966-2973 (2016).
Qi et al. In vitro anticancer activities of prodrugs engineered based on the structure of gemcitabine. Chinese Master's Theses Full-text Database, Medicine and Health Sciences pp. E079-E0314 (2016).
Thornton et al. Nucleoside Phosphate and Phosphonate Prodrug Clinical Candidates : Miniperspective. J Med Chem 59(23):10400-10410 (2016).
U.S. Appl. No. 16/635,469 Office Action dated Jun. 2, 2021.
U.S. Appl. No. 16/992,036 Office Action dated Jul. 27, 2021.
Yang et al. Studies on preparation and stability of human serum albumin nanoparticles containing gambogic acid. Chinese Journal of Pharmaceutics 14(4):107-119 (2016) (English Abstract).
Sleep. Albumin and its application in drug delivery. Expert Opin Drug Deliv. 12(5):793-812 (2015).
U.S. Appl. No. 16/976,909 Office Action dated Jan. 19, 2022.

\* cited by examiner

ORGANOPHOSPHATE DERIVATIVES

CROSS-REFERENCE TO RELATED APPLICATIONS

This application is a § 371 U.S. National Stage Application of International Application No. PCT/US2018/044389, filed Jul. 30, 2018, which claims benefit of U.S. Provisional Application No. 62/538,879, filed on Jul. 31, 2017, and U.S. Provisional Application No. 62/637,960, filed on Mar. 2, 2018, each of which is herein incorporated by reference in its entirety.

BACKGROUND

Cancer is among the leading causes of death worldwide. The number of new cancer cases is expected to rise to 22 million within the next two decades. Improved therapies are needed to treat this increasing patient population.

BRIEF SUMMARY OF THE INVENTION

This disclosure provides, for example, organophosphate compounds, their use as medicinal agents for the treatment of cancer, processes for their preparation, and pharmaceutical compositions that include disclosed compounds as at least one active ingredient. The disclosure also provides for the use of compounds described herein as medicaments and/or in the manufacture of medicaments for the treatment of cancer.

In one aspect is a compound of Formula (I):

Formula (I)

wherein:
$R^1$ is

, , or

;

$R^2$ is —C(O)$R^8$;
$R^3$ is H, —C(O)$R^9$, or —C(O)O$R^9$;
$R^4$ is H;
$R^5$ is H, $C_{3-22}$alkyl, $C_{3-22}$alkenyl, $C_{3-22}$alkynyl, $C_{3-22}$haloalkyl, —$C_{1-6}$alkyl-OC(O)$C_{1-22}$alkyl, $C_{3-8}$cycloalkyl, $C_{6-10}$aryl, —$C_{1-8}$alkyl-$C_{6-10}$aryl, $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl, $C_{2-9}$heteroaryl, or —$C_{1-8}$alkyl-$C_{2-9}$heteroaryl are optionally substituted with 1, 2, 3, or 4 $R^{14}$;
$R^6$ is $C_{3-22}$alkyl, $C_{3-22}$alkenyl, $C_{3-22}$alkynyl, $C_{3-22}$haloalkyl, —$C_{1-6}$alkyl-OC(O)$C_{1-22}$alkyl, $C_{3-8}$cycloalkyl, $C_{6-10}$aryl, —$C_{1-8}$alkyl-$C_{6-10}$aryl, $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl $C_{2-9}$heteroaryl, or —$C_{1-8}$alkyl-$C_{2-9}$heteroaryl are optionally substituted with 1, 2, 3, or 4 $R^{14}$;
each $R^7$ is independently selected from halogen, $C_{1-8}$alkyl, $C_{1-8}$haloalkyl, and $C_{1-8}$alkoxy;
$R^8$ is $C_{3-22}$alkyl, $C_{3-22}$alkenyl, $C_{3-22}$alkynyl, $C_{3-22}$haloalkyl, $C_{3-8}$cycloalkyl, $C_{6-10}$aryl, —$C_{1-8}$alkyl-$C_{6-10}$aryl $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl, $C_{2-9}$heteroaryl, or —$C_{1-8}$alkyl-$C_{2-9}$heteroaryl are optionally substituted with 1, 2, 3, or 4 $R^{14}$;
$R^9$ is $C_{1-12}$alkyl;
$R^{10}$ and $R^{11}$ are each independently H or $C_{1-12}$alkyl; or $R^{10}$ and $R^{11}$ form a 5- or 6-membered cycloalkyl ring or a 5- or 6-membered heterocycloalkyl ring, wherein the 5- or 6-membered cycloalkyl ring or the 5- or 6-membered heterocycloalkyl ring are optionally substituted with one or two $R^{13}$;
$R^{12}$ is H or $C_{1-12}$alkyl;
each $R^{13}$ is independently selected from $C_{1-12}$alkyl;
each $R^{14}$ is independently selected from halogen, $C_{1-8}$alkyl $C_{1-8}$haloalkyl $C_{1-8}$alkoxy, and —C(O)$R^{13}$;
m is 0 or 1;
n is 0, 1, 2, 3, or 4; and
p is 0 or 1;
or a pharmaceutically acceptable salt thereof.

In another aspect is a compound of Formula (I'):

Formula (I')

wherein:
$R^1$ is

, , or

;

$R^2$ is —C(O)$R^8$;
$R^3$ is H, —C(O)$R^9$, or —C(O)O$R^9$;
$R^4$ is H;

$R^5$ is H, $C_{3-22}$alkyl, $C_{3-22}$alkenyl, $C_{3-22}$alkynyl, $C_{3-22}$haloalkyl, —$C_{1-4}$alkyl-OC(O)$C_{1-8}$alkyl, $C_{3-8}$cycloalkyl, $C_{6-10}$aryl, —$C_{1-8}$alkyl-$C_{6-10}$aryl, $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl, $C_{2-9}$heteroaryl, or —$C_{1-8}$alkyl-$C_{2-9}$heteroaryl are optionally substituted with 1, 2, 3, or 4 $R^{14}$;

$R^6$ is $C_{3-22}$alkyl, $C_{3-22}$alkenyl, $C_{3-22}$alkynyl, $C_{3-22}$haloalkyl, —$C_{1-4}$alkyl-OC(O)$C_{1-8}$alkyl, $C_{3-8}$cycloalkyl, $C_{6-10}$aryl, —$C_{1-8}$alkyl-$C_{6-10}$aryl $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl, $C_{2-9}$heteroaryl, or —$C_{1-8}$alkyl-$C_{2-9}$heteroaryl are optionally substituted with 1, 2, 3, or 4 $R^{14}$;

each $R^7$ is independently selected from halogen, $C_{1-8}$alkyl, $C_{1-8}$haloalkyl, and $C_{1-8}$alkoxy;

$R^8$ is $C_{3-22}$alkyl, $C_{3-22}$alkenyl, $C_{3-22}$alkynyl, $C_{3-22}$haloalkyl, $C_{3-8}$cycloalkyl, $C_{6-10}$aryl, —$C_{1-8}$alkyl-$C_{6-10}$aryl, $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl $C_{2-9}$heteroaryl, or —$C_{1-8}$alkyl-$C_{2-9}$heteroaryl are optionally substituted with 1, 2, 3, or 4 $R^{14}$;

$R^9$ is $C_{1-12}$alkyl;

$R^{10}$ and $R^{11}$ are each independently H or $C_{1-12}$alkyl; or $R^{10}$ and $R^{11}$ form a 5- or 6-membered cycloalkyl ring or a 5- or 6-membered heterocycloalkyl ring, wherein the 5- or 6-membered cycloalkyl ring or the 5- or 6-membered heterocycloalkyl ring are optionally substituted with one or two $R^{13}$;

$R^{12}$ is H or $C_{1-12}$alkyl;

each $R^{13}$ is independently selected from $C_{1-12}$alkyl;

each $R^{14}$ is independently selected from halogen, $C_{1-8}$alkyl, $C_{1-8}$haloalkyl, $C_{1-8}$alkoxy, and —C(O)$R^{13}$;

m is 0 or 1;

n is 0, 1, 2, 3, or 4; and p is 0 or 1;

or a pharmaceutically acceptable salt thereof.

In another embodiment is a compound of Formula (I) or (I'), or a pharmaceutically acceptable salt thereof, wherein $R^1$ is

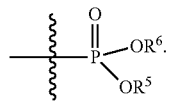

In another embodiment is a compound of Formula (I) or (I'), or a pharmaceutically acceptable salt thereof, wherein $R^5$ is $C_{3-16}$alkyl. In another embodiment is a compound of Formula (I) or (I'), or a pharmaceutically acceptable salt thereof, wherein $R^5$ is $C_{3-12}$alkyl. In another embodiment is a compound of Formula (I) or (I'), or a pharmaceutically acceptable salt thereof, wherein $R^5$ is $C_{6-14}$alkyl. In another embodiment is a compound of Formula (I) or (I'), or a pharmaceutically acceptable salt thereof, wherein $R^5$ is $C_{6-10}$alkyl. In another embodiment is a compound of Formula (I), or a pharmaceutically acceptable salt thereof, wherein $R^5$ is —$C_{1-4}$alkyl-OC(O)$C_{1-16}$alkyl. In another embodiment is a compound of Formula (I), or a pharmaceutically acceptable salt thereof, wherein $R^5$ is —$C_{1-4}$alkyl-OC(O)$C_{1-12}$alkyl. In another embodiment is a compound of Formula (I) or (I'), or a pharmaceutically acceptable salt thereof, wherein $R^5$ is —$C_{1-4}$alkyl-OC(O)$C_{1-8}$alkyl. In another embodiment is a compound of Formula (I) or (I'), or a pharmaceutically acceptable salt thereof, wherein $R^5$ is —$C_{1-2}$alkyl-OC(O)$C_{1-6}$alkyl. In another embodiment is a compound of Formula (I) or (I'), or a pharmaceutically acceptable salt thereof, wherein $R^5$ is —CH$_2$—OC(O)C(CH$_3$)$_3$. In another embodiment is a compound of Formula (I) or (I'), or a pharmaceutically acceptable salt thereof, wherein $R^5$ is H. In another embodiment is a compound of Formula (I) or (I'), or a pharmaceutically acceptable salt thereof, wherein $R^6$ is $C_{3-16}$alkyl. In another embodiment is a compound of Formula (I) or (I'), or a pharmaceutically acceptable salt thereof, wherein $R^6$ is $C_{3-12}$alkyl. In another embodiment is a compound of Formula (I) or (I'), or a pharmaceutically acceptable salt thereof, wherein $R^6$ is $C_{6-10}$alkyl. In another embodiment is a compound of Formula (I), or a pharmaceutically acceptable salt thereof, wherein $R^6$ is —$C_{1-4}$alkyl-OC(O)$C_{1-16}$alkyl. In another embodiment is a compound of Formula (I), or a pharmaceutically acceptable salt thereof, wherein $R^6$ is —$C_{1-4}$alkyl-OC(O)$C_{1-12}$alkyl. In another embodiment is a compound of Formula (I) or (I'), or a pharmaceutically acceptable salt thereof, wherein $R^6$ is —$C_{1-4}$alkyl-OC(O)$C_{1-8}$alkyl. In another embodiment is a compound of Formula (I) or (I'), or a pharmaceutically acceptable salt thereof, wherein $R^6$ is —$C_{1-2}$alkyl-OC(O)$C_{1-6}$alkyl. In another embodiment is a compound of Formula (I) or (I'), or a pharmaceutically acceptable salt thereof, wherein $R^6$ is —CH$_2$—OC(O)C(CH$_3$)$_3$. In another embodiment is a compound of Formula (I) or (I'), or a pharmaceutically acceptable salt thereof, wherein $R^1$ is

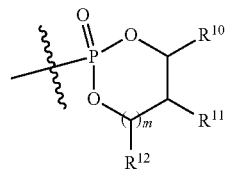

In another embodiment is a compound of Formula (I) or (I'), or a pharmaceutically acceptable salt thereof, wherein m is 0. In another embodiment is a compound of Formula (I) or (I'), or a pharmaceutically acceptable salt thereof, wherein m is 1. In another embodiment is a compound of Formula (I) or (I'), or a pharmaceutically acceptable salt thereof, wherein $R^{10}$ is H. In another embodiment is a compound of Formula (I) or (I'), or a pharmaceutically acceptable salt thereof, wherein $R^{10}$ is $C_{1-12}$alkyl. In another embodiment is a compound of Formula (I) or (I'), or a pharmaceutically acceptable salt thereof, wherein $R^{11}$ is H. In another embodiment is a compound of Formula (I) or (I'), or a pharmaceutically acceptable salt thereof, wherein $R^{10}$ and $R^{11}$ form a 5- or 6-membered cycloalkyl ring or a 5- or 6-membered heterocycloalkyl ring, wherein the 5- or 6-membered cycloalkyl ring or the 5- or 6-membered heterocycloalkyl ring are optionally substituted with one or two $R^{13}$. In another embodiment is a compound of Formula (I) or (I'), or a pharmaceutically acceptable salt thereof, wherein $R^1$ is

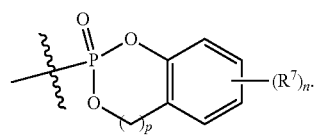

In another embodiment is a compound of Formula (I) or (I'), or a pharmaceutically acceptable salt thereof, wherein each $R^7$ is independently selected from $C_{1-8}$alkyl, $C_{1-8}$haloalkyl, and $C_{1-8}$alkoxy. In another embodiment is a compound of Formula (I) or (I'), or a pharmaceutically acceptable salt thereof, wherein each $R^7$ is independently selected from $C_{1-8}$alkyl. In another embodiment is a compound of Formula (I) or (I'), or a pharmaceutically acceptable salt thereof, wherein n is 1 or 2. In another embodiment is a compound of Formula (I) or (I'), or a pharmaceutically acceptable salt thereof, wherein n is 0. In another embodiment is a compound of Formula (I) or (I'), or a pharmaceutically acceptable salt thereof, wherein p is 0. In another embodiment is a compound of Formula (I) or (I'), or a pharmaceutically acceptable salt thereof, wherein p is 1. In another embodiment is a compound of Formula (I) or (I'), or a pharmaceutically acceptable salt thereof, wherein $R^8$ is $C_{3-15}$alkyl. In another embodiment is a compound of Formula (I) or (I'), or a pharmaceutically acceptable salt thereof, wherein $R^8$ is $C_{6-18}$alkyl. In another embodiment is a compound of Formula (I) or (I'), or a pharmaceutically acceptable salt thereof, wherein $R^8$ is $C_{6-12}$alkyl. In another embodiment is a compound of Formula (I) or (I'), or a pharmaceutically acceptable salt thereof, wherein $R^8$ is —$(CH_2)_7CH_3$.

In another aspect is a compound of Formula (II):

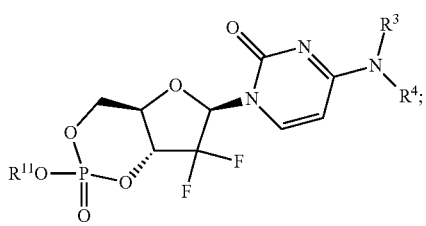

Formula (II)

wherein:
  $R^3$ is H, H, —C(O)$R^9$, or —C(O)O$R^9$;
  $R^4$ is H;
  $R^9$ is $C_{1-8}$alkyl;
  $R^{11}$ is $C_{3-22}$alkyl, $C_{3-22}$alkenyl, $C_{3-22}$alkynyl, $C_{3-22}$haloalkyl, —$C_{1-4}$alkyl-OC(O)$C_{1-8}$alkyl, $C_{6-10}$aryl, —$C_{1-8}$alkyl-$C_{6-10}$aryl, $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl, $C_{2-9}$heteroaryl, or —$C_{1-8}$alkyl-$C_{2-9}$heteroaryl are optionally substituted with 1, 2, 3, or 4 $R^{12}$;
  each $R^{12}$ is independently selected from halogen, $C_{1-8}$alkyl, $C_{1-8}$haloalkyl, $C_{1-8}$alkoxy, and —C(O)$R^{13}$; and
  each $R^{13}$ is independently selected from $C_{1-12}$alkyl;
  or a pharmaceutically acceptable salt thereof.

In another embodiment is a compound of Formula (II), or a pharmaceutically acceptable salt thereof, wherein $R^{11}$ is $C_{3-15}$alkyl. In another embodiment is a compound of Formula (II), or a pharmaceutically acceptable salt thereof, wherein $R^{11}$ is $C_{6-12}$alkyl. In another embodiment is a compound of Formula (II), or a pharmaceutically acceptable salt thereof, wherein $R^{11}$ is $C_{8-10}$alkyl. In another embodiment is a compound of Formula (II), or a pharmaceutically acceptable salt thereof, wherein $R^{11}$ is $C_{8-22}$alkyl. In another embodiment is a compound of Formula (II), or a pharmaceutically acceptable salt thereof, wherein $R^{11}$ is $C_{16-22}$alkyl. In another embodiment is a compound of Formula (II), or a pharmaceutically acceptable salt thereof, wherein $R^{11}$ is —$C_{1-4}$alkyl-OC(O)$C_{1-8}$alkyl. In another embodiment is a compound of Formula (II), or a pharmaceutically acceptable salt thereof, wherein $R^{11}$ is —$C_{1-2}$alkyl-OC(O)$C_{1-6}$alkyl. In another embodiment is a compound of Formula (II), or a pharmaceutically acceptable salt thereof, wherein $R^{11}$ is —$CH_2$—OC(O)C($CH_3$)$_3$. In another embodiment is a compound of Formula (II), or a pharmaceutically acceptable salt thereof, wherein $R^{11}$ is $C_{6-10}$aryl optionally substituted with 1, 2, 3, or 4 $R^{12}$. In another embodiment is a compound of Formula (II), or a pharmaceutically acceptable salt thereof, wherein $R^{11}$ is phenyl optionally substituted with 1, 2, or 3 $R^{12}$. In another embodiment is a compound of Formula (II), or a pharmaceutically acceptable salt thereof, wherein $R^{11}$ is phenyl optionally substituted with 1, 2, or 3 $R^{12}$ and each $R^{12}$ is independently selected from $C_{1-8}$alkyl, $C_{1-8}$alkoxy, and —C(O)$R^{13}$. In another embodiment is a compound of Formula (II), or a pharmaceutically acceptable salt thereof, wherein $R^{11}$ is phenyl optionally substituted with 1 or 2 $R^{12}$ and each $R^{12}$ is independently selected from $C_{1-8}$alkyl and $C_{1-8}$alkoxy. In another embodiment is a compound of Formula (II), or a pharmaceutically acceptable salt thereof, wherein $R^{11}$ is —$C_{1-8}$alkyl-$C_{6-10}$aryl optionally substituted with 1, 2, 3, or 4 $R^{12}$. In another embodiment is a compound of Formula (II), or a pharmaceutically acceptable salt thereof, wherein $R^{11}$ is —$CH_2$-phenyl optionally substituted with 1, 2, or 3 $R^{12}$. In another embodiment is a compound of Formula (II), or a pharmaceutically acceptable salt thereof, wherein $R^{11}$ is —$CH_2$-phenyl optionally substituted with 1, 2, or 3 $R^{12}$ and each $R^{12}$ is independently selected from $C_{1-8}$alkyl, $C_{1-8}$alkoxy, and —C(O)$R^{13}$. In another embodiment is a compound of Formula (II), or a pharmaceutically acceptable salt thereof, wherein $R^{11}$ is —$CH_2$-phenyl optionally substituted with 1, 2, or 3 $R^{12}$ and each $R^{12}$ is independently selected from $C_{1-8}$alkyl and $C_{1-8}$alkoxy. In another embodiment is a compound of Formula (I), (I'), or (II), or a pharmaceutically acceptable salt thereof, wherein $R^3$ is H. In another embodiment is a compound of Formula (I), (I'), or (II), or a pharmaceutically acceptable salt thereof, wherein $R^3$ is —C(O)$R^9$. In another embodiment is a compound of Formula (I), (I'), or (II), or a pharmaceutically acceptable salt thereof, wherein $R^3$ is —C(O)O$R^9$.

In another embodiment is a pharmaceutical composition comprising a compound of Formula (I), (I'), or (II) described herein, or a pharmaceutically acceptable salt thereof, and at least one pharmaceutically acceptable excipient.

In another embodiment is a method of treating cancer in a patient, comprising administering to the patient in need thereof a therapeutically effective amount of a compound of Formula (I), (I'), or (II) described herein, or a pharmaceutically acceptable salt thereof. In another embodiment is a method of treating an infectious disease in a patient, comprising administering to the patient in need thereof a therapeutically effective amount of a compound of Formula (I), (I'), or (II) described herein, or a pharmaceutically acceptable salt thereof.

DETAILED DESCRIPTION OF THE INVENTION

Nucleoside analogues constitute a major class of chemotherapeutic agents and are used for the treatment of patients with cancer. This group of agents, known as antimetabolites, includes a variety of pyrimidine and purine nucleoside derivatives with cytotoxic activity in both hematological and solid tumors. Gemcitabine (2',2'-difluoro-2'-deoxycytidine) is a pyrimidine nucleoside analogue, shown to be active against several solid tumor types.

Both innate and acquired resistance to nucleoside analogues is a problem in the treatment of cancer and is regarded as a driver of poor patient survival outcomes. Gemcitabine faces inherent and acquired cancer resistance mechanisms that limit its effectiveness. These include (i) poor conversion of gemcitabine into the active forms, dFdCDP and dFdCTP; (ii) rapid degradation into toxic byproducts; and (iii) limited uptake by cancer cells. These effects are due to the following: (i) down-regulation of the key initial phosphorylating enzyme deoxycytidine kinase (dCK) required to convert gemcitabine into the monophosphate form; (ii) expression of the key deactivating enzyme cytidine deaminase; and (iii) deficiency of nucleoside transporter proteins. In addition, increased expression and/or activity of cytidine deaminase (CDA) increases the degradation of gemcitabine into the toxic metabolite 2',2'-difluoro-2'-deoxyuridine (dFdU). Because of these processes, single agent gemcitabine has limited activity in cancer treatment.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Alkyl" or "alkylene" refers to a straight or branched hydrocarbon chain radical consisting solely of carbon and hydrogen atoms, containing no unsaturation, having from one to eighteen carbon atoms (e.g., $C_1$-$C_{18}$ alkyl). In certain embodiments, an alkyl comprises three to eighteen carbon atoms (e.g., $C_3$-$C_{18}$ alkyl). In certain embodiments, an alkyl comprises one to fifteen carbon atoms (e.g., $C_1$-$C_{15}$ alkyl). In certain embodiments, an alkyl comprises one to twelve carbon atoms (e.g., $C_1$-$C_{12}$ alkyl). In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)O$R^a$, —C(O)N($R^a)_2$, —$N(R^a)$C(O)O$R^f$, —OC(O)—N$R^a R^f$, —$N(R^a)$C(O)$R^f$, —$N(R^a)$S(O)$_t R^f$ (where t is 1 or 2), —S(O)$_t OR^a$ (where t is 1 or 2), —S(O)$_t R^f$ (where t is 1 or 2) and —S(O)$_t N(R^a)_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to eighteen carbon atoms. In certain embodiments, an alkenyl comprises three to eighteen carbon atoms. In certain embodiments, an alkenyl comprises three to twelve carbon atoms. In certain embodiments, an alkenyl comprises six to twelve carbon atoms. In certain embodiments, an alkenyl comprises six to ten carbon atoms. In certain embodiments, an alkenyl comprises eight to ten carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)O$R^a$, —C(O)N($R^a)_2$, —$N(R^a)$C(O)O$R^f$, —OC(O)—N$R^a R^f$, —$N(R^a)$C(O)$R^f$, —$N(R^a)$S(O)$_t R^f$ (where t is 1 or 2), —S(O)$_t OR^a$ (where t is 1 or 2), —S(O)$_t R^f$ (where t is 1 or 2) and —S(O)$_t N(R^a)_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Alkynyl" refers to a straight or branched hydrocarbon chain radical group consisting solely of carbon and hydrogen atoms, containing at least one carbon-carbon triple bond, having from two to eighteen carbon atoms. In certain embodiments, an alkynyl comprises three to eighteen carbon atoms. In certain embodiments, an alkynyl comprises three to twelve carbon atoms. In certain embodiments, an alkynyl comprises six to twelve carbon atoms. In certain embodiments, an alkynyl comprises six to ten carbon atoms. In certain embodiments, an alkynyl comprises eight to ten carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^f$, —$N(R^a)_2$, —C(O)$R^a$, —C(O)O$R^a$, —C(O)N$(R^a)_2$, —N($R^a$)C(O)O$R^f$, —OC(O)—N$R^aR^f$, —N($R^a$)C(O)$R^f$, —N($R^a$)S(O)$_tR^f$ (where t is 1 or 2), —S(O)$_tOR^a$ (where t is 1 or 2), —S(O)$_tR^f$ (where t is 1 or 2) and —S(O)$_tN(R^a)_2$ (where t is 1 or 2) where each $R^a$ is independently hydrogen, alkyl, haloalkyl, cycloalkyl, aryl, aralkyl, heterocycloalkyl, heteroaryl, or heteroarylalkyl, and each $R^f$ is independently alkyl, haloalkyl, cycloalkyl, aryl, aralkyl, heterocycloalkyl, heteroaryl, or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents selected from alkyl, alkenyl, alkynyl, halo, haloalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—N($R^a$)C(O)$OR^a$, —$R^b$—N($R^a$)C(O)$R^a$, —$R^b$—N($R^a$)S(O)$_tR^a$ (where t is 1 or 2), —$R^b$—S(O)$_tOR^a$ (where t is 1 or 2), —$R^b$—S(O)$_tR^a$ (where t is 1 or 2), and —$R^b$—S(O)$_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O— aralkyl, where aralkyl is as defined above.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyls are saturated, (i.e., containing single C—C bonds only) or partially unsaturated (i.e., containing one or more double bonds or triple bonds.) Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless stated otherwise specifically in the specification, the term "cycloalkyl" is meant to include cycloalkyl radicals that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$C(O)$R^a$, —$R^b$—C(O)$OR^a$, —$R^b$—C(O)$N(R^a)_2$, —$R^b$—O—$R^c$—C(O)$N(R^a)_2$, —$R^b$N($R^a$)C(O)$OR^a$, —$R^b$—N($R^a$)C(O)$R^a$, —$R^b$—N($R^a$)S(O)$_tR^a$ (where t is 1 or 2), —$R^b$—S(O)$_tOR^a$ (where t is 1 or 2), —$R^b$—S(O)$_tR^a$ (where t is 1 or 2), and —$R^b$—S(O)$_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Halo" or "halogen" refers to bromo, chloro, fluoro or iodo substituents.

"Haloalkyl" refers to an alkyl radical, as defined above, that is substituted by one or more halo radicals, as defined above.

"Haloalkoxy" refers to an alkoxy radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic, or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tR^a$ (where t is 1 or 2), and $-R^b-S(O)_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"Heteroaryl" refers to a radical derived from a 3- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above which are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tOR^a$ (where t is 1 or 2), $-R^b-S(O)_tR^a$ (where t is 1 or 2), and $-R^b-S(O)_tN(R^a)_2$ (where t is 1 or 2), where each $R^a$ is independently hydrogen, alkyl, haloalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O-heteroaryl, where heteroaryl is as defined above.

"Heteroarylalkyl" refers to a radical of the formula $-R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

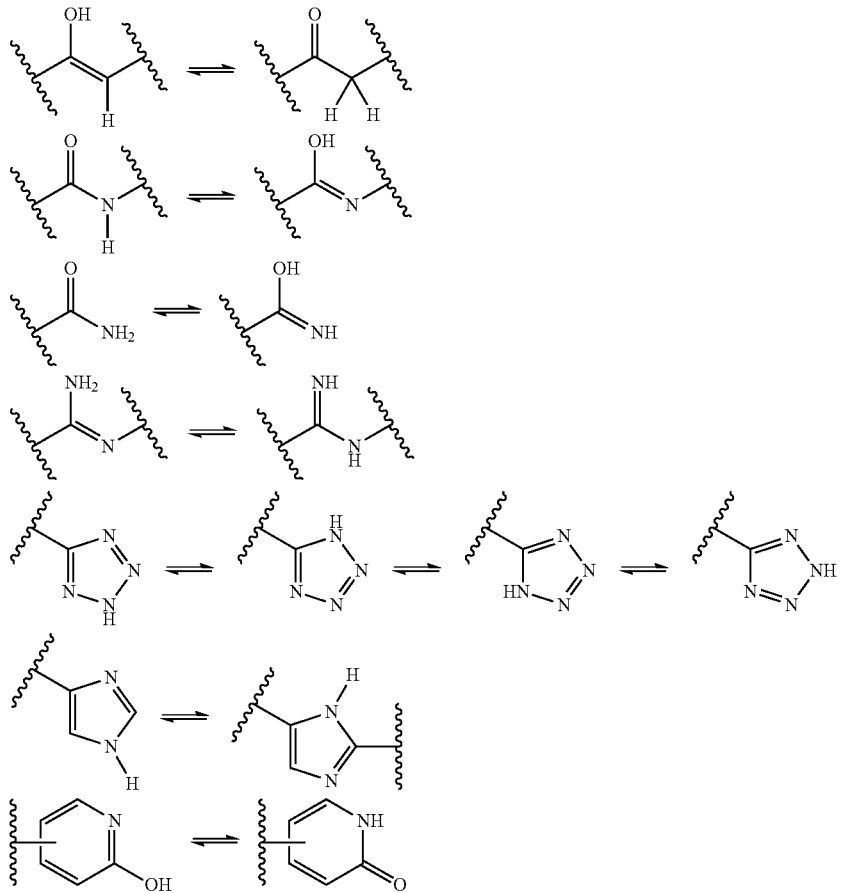

"Optional" or "optionally" means that a subsequently described event or circumstance may or may not occur and that the description includes instances when the event or circumstance occurs and instances in which it does not. For example, "optionally substituted aryl" means that the aryl radical are or are not substituted and that the description includes both substituted aryl radicals and aryl radicals having no substitution.

"Pharmaceutically acceptable salt" includes both acid and base addition salts. A pharmaceutically acceptable salt of any one of the pyrazole compounds described herein is intended to encompass any and all pharmaceutically suitable salt forms. Preferred pharmaceutically acceptable salts of the compounds described herein are pharmaceutically acceptable acid addition salts, and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

As used herein, "treatment" or "treating" or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

Compounds

In some embodiments, the compounds of Formula (I), (I'), (Ia), (Ib), (Ic), or (II) described herein, and compositions comprising these compounds, are useful for the treatment of cancer. In some embodiments, the compounds of Formula (I), (I'), (Ia), (Ib), (Ic), or (II) described herein, and compositions comprising these compounds, are useful for the treatment of an infectious disease.

In some embodiments is a compound of Formula (I):

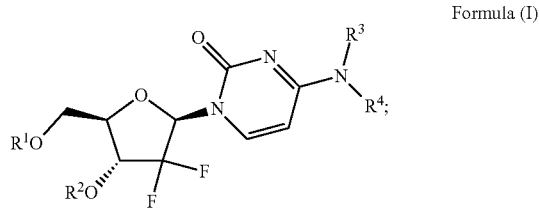

Formula (I)

wherein:

$R^1$ is

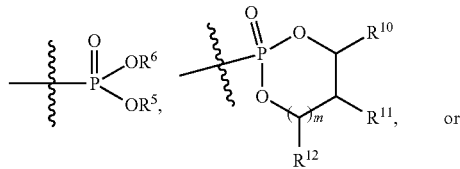

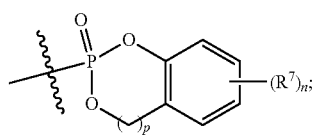

$R^2$ is —C(O)$R^8$;

$R^3$ is H, —C(O)$R^9$, or —C(O)O$R^9$;

$R^4$ is H;

$R^5$ is H, $C_{3-22}$alkyl, $C_{3-22}$alkenyl, $C_{3-22}$alkynyl, $C_{3-22}$haloalkyl, —$C_{1-6}$alkyl-OC(O)$C_{1-22}$alkyl, $C_{3-8}$cycloalkyl, $C_{6-10}$aryl, —$C_{1-8}$alkyl-$C_{6-10}$aryl, $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl, $C_{2-9}$heteroaryl, or —$C_{1-8}$alkyl-$C_{2-9}$heteroaryl are optionally substituted with 1, 2, 3, or 4 $R^{14}$;

$R^6$ is $C_{3-22}$alkyl, $C_{3-22}$alkenyl, $C_{3-22}$alkynyl, $C_{3-22}$haloalkyl, —$C_{1-6}$alkyl-OC(O)$C_{1-22}$alkyl, $C_{3-8}$cycloalkyl, $C_{6-10}$aryl, —$C_{1-8}$alkyl-$C_{6-10}$aryl, $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl, $C_{2-9}$heteroaryl, or —$C_{1-8}$alkyl-$C_{2-9}$heteroaryl are optionally substituted with 1, 2, 3, or 4 $R^{14}$;

each $R^7$ is independently selected from halogen, $C_{1-8}$alkyl, $C_{1-8}$haloalkyl, and $C_{1-8}$alkoxy;

$R^8$ is $C_{3-22}$alkyl, $C_{3-22}$alkenyl, $C_{3-22}$alkynyl, $C_{3-22}$haloalkyl, $C_{3-8}$cycloalkyl, $C_{6-10}$aryl, —$C_{1-8}$alkyl-$C_{6-10}$aryl, $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl, $C_{2-9}$heteroaryl, or —$C_{1-8}$alkyl-$C_{2-9}$heteroaryl are optionally substituted with 1, 2, 3, or 4 $R^{14}$;

$R^9$ is $C_{1-12}$alkyl;

$R^{10}$ and $R^{11}$ are each independently H or $C_{1-12}$alkyl; or $R^{10}$ and $R^{11}$ form a 5- or 6-membered cycloalkyl ring or a 5- or 6-membered heterocycloalkyl ring, wherein the 5- or 6-membered cycloalkyl ring or the 5- or 6-membered heterocycloalkyl ring are optionally substituted with one or two $R^{13}$;

$R^{12}$ is H or $C_{1-12}$alkyl;

each $R^{13}$ is independently selected from $C_{1-12}$alkyl;

each $R^{14}$ is independently selected from halogen, $C_{1-8}$alkyl $C_{1-8}$haloalkyl $C_{1-8}$alkoxy, and —C(O)$R^{13}$;

m is 0 or 1;

n is 0, 1, 2, 3, or 4; and p is 0 or 1;

or a pharmaceutically acceptable salt thereof.

In some embodiments is a compound of Formula (I'):

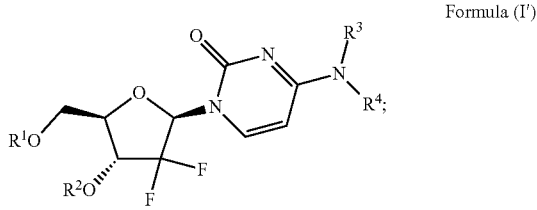

Formula (I')

wherein:
R¹ is

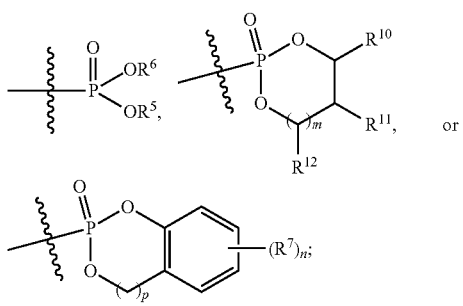

R² is —C(O)R⁸;
R³ is H, —C(O)R⁹, or —C(O)OR⁹;
R⁴ is H;
R⁵ is H, $C_{3-18}$alkyl, $C_{3-18}$alkenyl, $C_{3-18}$alkynyl, $C_{3-18}$haloalkyl, —$C_{1-4}$alkyl-OC(O)$C_{1-8}$alkyl, $C_{3-8}$cycloalkyl, $C_{6-10}$aryl, —$C_{1-8}$alkyl-$C_{6-10}$aryl, $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl, $C_{2-9}$heteroaryl, or —$C_{1-8}$alkyl-$C_{2-9}$heteroaryl are optionally substituted with 1, 2, 3, or 4 R¹⁴;
R⁶ is $C_{3-18}$alkyl, $C_{3-18}$alkenyl, $C_{3-18}$alkynyl, $C_{3-18}$haloalkyl, —$C_{1-4}$alkyl-OC(O)$C_{1-8}$alkyl, $C_{3-8}$cycloalkyl, $C_{6-10}$aryl, —$C_{1-8}$alkyl-$C_{6-10}$aryl $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl, $C_{2-9}$heteroaryl, or —$C_{1-8}$alkyl-$C_{2-9}$heteroaryl are optionally substituted with 1, 2, 3, or 4 R¹⁴;
each R⁷ is independently selected from halogen, $C_{1-8}$alkyl, $C_{1-8}$haloalkyl, and $C_{1-8}$alkoxy;
R⁸ is $C_{3-18}$alkyl, $C_{3-18}$alkenyl, $C_{3-18}$alkynyl, $C_{3-18}$haloalkyl, $C_{3-8}$cycloalkyl, $C_{6-10}$aryl, —$C_{1-8}$alkyl-$C_{6-10}$aryl, $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl, $C_{2-9}$heteroaryl, or —$C_{1-8}$alkyl-$C_{2-9}$heteroaryl are optionally substituted with 1, 2, 3, or 4 R¹⁴;
R⁹ is $C_{1-12}$alkyl;
R¹⁰ and R¹¹ are each independently H or $C_{1-12}$alkyl; or R¹⁰ and R¹¹ form a 5- or 6-membered cycloalkyl ring or a 5- or 6-membered heterocycloalkyl ring, wherein the 5- or 6-membered cycloalkyl ring or the 5- or 6-membered heterocycloalkyl ring are optionally substituted with one or two R¹³;
R¹² is H or $C_{1-12}$alkyl;
each R¹³ is independently selected from $C_{1-12}$alkyl;
each R¹⁴ is independently selected from halogen, $C_{1-8}$alkyl, $C_{1-8}$haloalkyl, $C_{1-8}$alkoxy, and —C(O)R¹³;

m is 0 or 1;
n is 0, 1, 2, 3, or 4; and
p is 0 or 1;
or a pharmaceutically acceptable salt thereof.

In another embodiment is a compound of Formula (I) or (I'), or a pharmaceutically acceptable salt thereof, wherein R¹ is

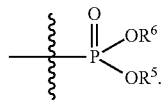

In another embodiment is a compound of Formula (I) or (I'), or a pharmaceutically acceptable salt thereof, wherein R¹ is

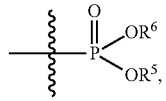

R⁵ is $C_{3-18}$alkyl, and R⁶ is $C_{3-18}$alkyl. In another embodiment is a compound of Formula (I) or (I'), or a pharmaceutically acceptable salt thereof, wherein R¹ is

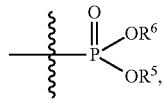

R⁵ is $C_{3-16}$alkyl, and R⁶ is $C_{3-16}$alkyl. In another embodiment is a compound of Formula (I) or (I'), or a pharmaceutically acceptable salt thereof, wherein R¹ is

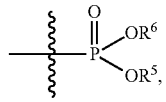

R⁵ is $C_{3-15}$alkyl, and R⁶ is $C_{3-15}$alkyl. In another embodiment is a compound of Formula (I) or (I'), or a pharmaceutically acceptable salt thereof, wherein R¹ is

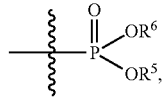

R⁵ is $C_{3-12}$alkyl, and R⁶ is $C_{3-12}$alkyl. In another embodiment is a compound of Formula (I) or (I'), or a pharmaceutically acceptable salt thereof, wherein R¹ is

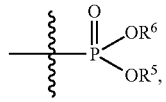

R⁵ is $C_{6-15}$alkyl, and R⁶ is $C_{6-15}$alkyl. In another embodiment is a compound of Formula (I) or (I'), or a pharmaceutically acceptable salt thereof, wherein R¹ is

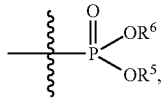

$R^5$ is $C_{6-14}$alkyl, and $R^6$ is $C_{6-14}$alkyl. In another embodiment is a compound of Formula (I) or (I'), or a pharmaceutically acceptable salt thereof, wherein $R^1$ is

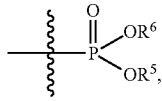

$R^5$ is $C_{6-12}$alkyl, and $R^6$ is $C_{6-12}$alkyl. In another embodiment is a compound of Formula (I) or (I'), or a pharmaceutically acceptable salt thereof, wherein $R^1$ is

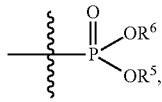

$R^5$ is $C_{6-10}$alkyl, and $R^6$ is $C_{6-10}$alkyl. In another embodiment is a compound of Formula (I) or (I'), or a pharmaceutically acceptable salt thereof, wherein $R^1$ is

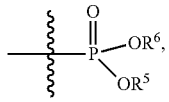

$R^5$ is $C_{3-18}$alkyl, and $R^6$ is $C_{3-18}$alkyl. In another embodiment is a compound of Formula (I) or (I'), or a pharmaceutically acceptable salt thereof, wherein $R^1$ is

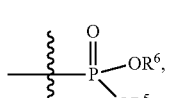

$R^5$ is $C_{3-15}$alkyl, and $R^6$ is $C_{3-15}$alkyl. In another embodiment is a compound of Formula (I) or (I'), or a pharmaceutically acceptable salt thereof, wherein $R^1$ is

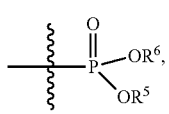

$R^5$ is $C_{6-15}$alkyl, and $R^6$ is $C_{6-15}$alkyl. In another embodiment is a compound of Formula (I) or (I'), or a pharmaceutically acceptable salt thereof, wherein $R^1$ is

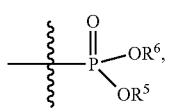

$R^5$ is $C_{6-12}$alkyl, and $R^6$ is $C_{6-12}$alkyl. In another embodiment is a compound of Formula (I) or (I'), or a pharmaceutically acceptable salt thereof, wherein $R^1$ is

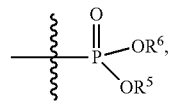

$R^5$ is $C_{6-10}$alkenyl, and $R^6$ is $C_{6-10}$alkenyl. In another embodiment is a compound of Formula (I) or (I'), or a pharmaceutically acceptable salt thereof, wherein $R^1$ is

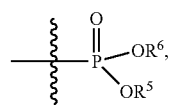

$R^5$ is $C_{3-18}$alkynyl and $R^6$ is $C_{3-18}$alkynyl. In another embodiment is a compound of Formula (I) or (I'), or a pharmaceutically acceptable salt thereof, wherein $R^1$ is

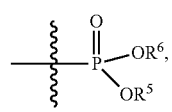

$R^5$ is $C_{3-15}$alkynyl, and $R^6$ is $C_{3-15}$alkynyl. In another embodiment is a compound of Formula (I) or (I'), or a pharmaceutically acceptable salt thereof, wherein $R^1$ is

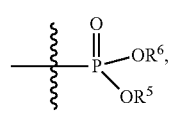

$R^5$ is $C_{6-15}$alkynyl, and $R^6$ is $C_{6-15}$alkynyl. In another embodiment is a compound of Formula (I) or (I'), or a pharmaceutically acceptable salt thereof, wherein $R^1$ is

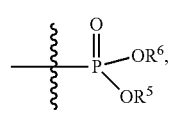

$R^5$ is $C_{6-12}$alkynyl, and $R^6$ is $C_{6-12}$alkynyl. In another embodiment is a compound of Formula (I) or (I'), or a pharmaceutically acceptable salt thereof, wherein $R^1$ is

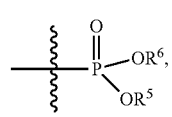

$R^5$ is $C_{6-10}$alkynyl, and $R^6$ is $C_{6-10}$alkynyl. In another embodiment is a compound of Formula (I) or (I'), or a pharmaceutically acceptable salt thereof, wherein $R^1$ is

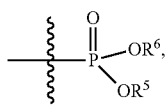

$R^5$ is $C_{3-18}$haloalkyl, and $R^6$ is $C_{3-18}$haloalkyl. In another embodiment is a compound of Formula (I) or (I'), or a pharmaceutically acceptable salt thereof, wherein $R^1$ is

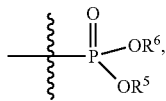

$R^5$ is $C_{3-15}$haloalkyl, and $R^6$ is $C_{3-15}$haloalkyl. In another embodiment is a compound of Formula (I) or (I'), or a pharmaceutically acceptable salt thereof, wherein $R^1$ is

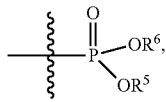

$R^5$ is $C_{6-15}$haloalkyl, and $R^6$ is $C_{6-15}$haloalkyl. In another embodiment is a compound of Formula (I) or (I'), or a pharmaceutically acceptable salt thereof, wherein $R^1$ is

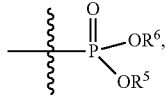

$R^5$ is $C_{6-12}$haloalkyl and $R^6$ is $C_{6-12}$haloalkyl. In another embodiment is a compound of Formula (I) or (I'), or a pharmaceutically acceptable salt thereof, wherein $R^1$ is

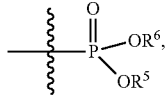

$R^5$ is $C_{6-10}$haloalkyl, and $R^6$ is $C_{6-10}$haloalkyl. In another embodiment is a compound of Formula (I), or a pharmaceutically acceptable salt thereof, wherein $R^1$ is

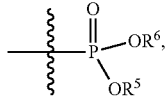

$R^5$ is —$C_{1-6}$alkyl-OC(O)$C_{1-22}$alkyl, and $R^6$ is —$C_{1-6}$alkyl-OC(O)$C_{1-22}$alkyl. In another embodiment is a compound of Formula (I), or a pharmaceutically acceptable salt thereof, wherein $R^1$ is

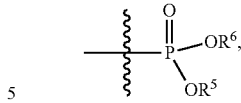

$R^5$ is —$C_{1-4}$alkyl-OC(O)$C_{1-16}$alkyl, and $R^6$ is —$C_{1-4}$alkyl-OC(O)$C_{1-16}$alkyl. In another embodiment is a compound of Formula (I), or a pharmaceutically acceptable salt thereof, wherein $R^1$ is

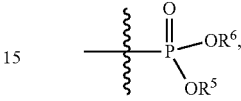

$R^5$ is —$C_{1-4}$alkyl-OC(O)$C_{1-12}$alkyl, and $R^6$ is —$C_{1-4}$alkyl-OC(O)$C_{1-12}$alkyl. In another embodiment is a compound of Formula (I) or (I'), or a pharmaceutically acceptable salt thereof, wherein $R^1$ is

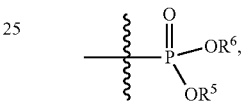

$R^5$ is —$C_{1-4}$alkyl-OC(O)$C_{1-8}$alkyl, and $R^6$ is —$C_{1-4}$alkyl-OC(O)$C_{1-8}$alkyl. In another embodiment is a compound of Formula (I) or (I'), or a pharmaceutically acceptable salt thereof, wherein $R^1$ is

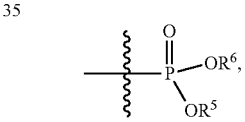

$R^5$ is —$C_{1-2}$alkyl-OC(O)$C_{1-8}$alkyl, and $R^6$ is —$C_{1-2}$alkyl-OC(O)$C_{1-8}$alkyl. In another embodiment is a compound of Formula (I) or (I'), or a pharmaceutically acceptable salt thereof, wherein $R^1$ is

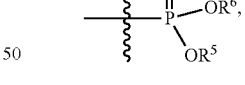

$R^5$ is —$CH_2$OC(O)$C_{1-8}$alkyl, and $R^6$ is —$CH_2$OC(O)$C_{1-8}$alkyl. In another embodiment is a compound of Formula (I) or (I'), or a pharmaceutically acceptable salt thereof, wherein $R^1$ is

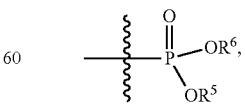

$R^5$ is —$C_{1-4}$alkyl-OC(O)$C_{1-6}$alkyl, and $R^6$ is —$C_{1-4}$alkyl-OC(O)$C_{1-6}$alkyl. In another embodiment is a compound of Formula (I) or (I'), or a pharmaceutically acceptable salt thereof, wherein $R^1$ is

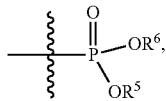

$R^5$ is —$C_{1-2}$alkyl-OC(O)$C_{1-6}$alkyl, and $R^6$ is —$C_{1-2}$alkyl-OC(O)$C_{1-6}$alkyl. In another embodiment is a compound of Formula (I) or (I'), or a pharmaceutically acceptable salt thereof, wherein $R^1$ is

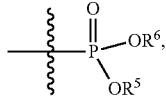

$R^5$ is —$CH_2OC(O)C_{1-6}$alkyl, and $R^6$ is —$CH_2OC(O)C_{1-6}$alkyl. In another embodiment is a compound of Formula (I) or (I'), or a pharmaceutically acceptable salt thereof, wherein $R^1$ is

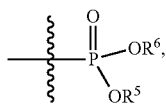

$R^5$ is —$C_{1-4}$alkyl-OC(O)$C_{1-4}$alkyl, and $R^6$ is —$C_{1-4}$alkyl-OC(O)$C_{1-4}$alkyl. In another embodiment is a compound of Formula (I) or (I'), or a pharmaceutically acceptable salt thereof, wherein $R^1$ is

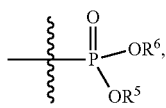

$R^5$ is —$C_{1-2}$alkyl-OC(O)$C_{1-4}$alkyl, and $R^6$ is —$C_{1-2}$alkyl-OC(O)$C_{1-4}$alkyl. In another embodiment is a compound of Formula (I) or (I'), or a pharmaceutically acceptable salt thereof, wherein $R^1$ is

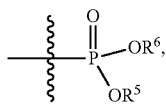

$R^5$ is —$CH_2OC(O)C_{1-4}$alkyl, and $R^6$ is —$CH_2OC(O)C_{1-4}$alkyl. In another embodiment is a compound of Formula (I) or (I'), or a pharmaceutically acceptable salt thereof, wherein $R^1$ is

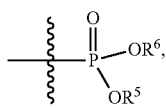

$R^5$ is —$C_{1-4}$alkyl-OC(O)C(CH$_3$)$_3$, and $R^6$ is —$C_{1-4}$alkyl-OC(O)C(CH$_3$)$_3$. In another embodiment is a compound of Formula (I) or (I'), or a pharmaceutically acceptable salt thereof, wherein $R^1$ is

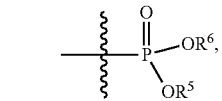

$R^5$ is —$C_{1-2}$alkyl-OC(O)C(CH$_3$)$_3$, and $R^6$ is —$C_{1-2}$alkyl-OC(O)C(CH$_3$)$_3$. In another embodiment is a compound of Formula (I) or (I'), or a pharmaceutically acceptable salt thereof, wherein $R^1$ is

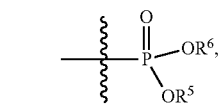

$R^5$ is —$CH_2OC(O)C(CH_3)_3$, and $R^6$ is —$CH_2OC(O)C(CH_3)_3$. In another embodiment is a compound of Formula (I) or (I'), or a pharmaceutically acceptable salt thereof, wherein $R^1$ is

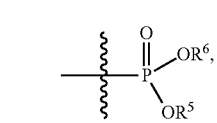

$R^5$ is $C_{3-8}$cycloalkyl, and $R^6$ is $C_{3-8}$cycloalkyl. In another embodiment is a compound of Formula (I) or (I'), or a pharmaceutically acceptable salt thereof, wherein $R^1$ is

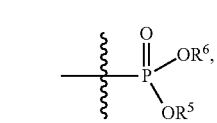

$R^5$ is $C_{3-6}$cycloalkyl, and $R^6$ is $C_{3-6}$cycloalkyl. In another embodiment is a compound of Formula (I) or (I'), or a pharmaceutically acceptable salt thereof, wherein $R^1$ is

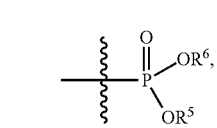

$R^5$ is unsubstituted $C_{6-10}$aryl, and $R^6$ is unsubstituted $C_{6-10}$aryl. In another embodiment is a compound of Formula (I) or (I'), or a pharmaceutically acceptable salt thereof, wherein $R^1$ is

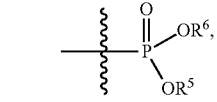

$R^5$ is $C_{6-10}$aryl substituted with 1 or 2 $R^{14}$, and $R^6$ is $C_{6-10}$aryl substituted with 1 or 2 $R^{14}$. In another embodiment is a compound of Formula (I) or (I'), or a pharmaceutically acceptable salt thereof, wherein $R^1$ is

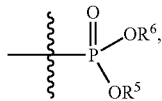

$R^5$ is unsubstituted phenyl, and $R^6$ is unsubstituted phenyl. In another embodiment is a compound of Formula (I) or (I'), or a pharmaceutically acceptable salt thereof, wherein $R^1$ is

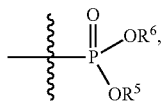

$R^5$ is phenyl substituted with 1 or 2 $R^{14}$ and $R^6$ is phenyl substituted with 1 or 2 $R^{14}$. In another embodiment is a compound of Formula (I) or (I'), or a pharmaceutically acceptable salt thereof, wherein $R^1$ is

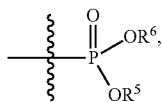

$R^5$ is unsubstituted —$C_{1-8}$alkyl-$C_{6-10}$aryl, and $R^6$ is unsubstituted —$C_{1-8}$alkyl-$C_{6-10}$aryl. In another embodiment is a compound of Formula (I) or (I'), or a pharmaceutically acceptable salt thereof, wherein $R^1$ is

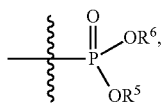

$R^5$ is —$C_{1-8}$alkyl-$C_{6-10}$aryl substituted with 1 or 2 $R^{14}$, and $R^6$ is —$C_{1-8}$alkyl-$C_{6-10}$aryl substituted with 1 or 2 $R^{14}$. In another embodiment is a compound of Formula (I) or (I'), or a pharmaceutically acceptable salt thereof, wherein $R^1$ is

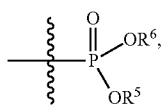

$R^5$ is unsubstituted —$CH_2$-phenyl, and $R^6$ is unsubstituted —$CH_2$-phenyl. In another embodiment is a compound of Formula (I) or (I'), or a pharmaceutically acceptable salt thereof, wherein $R^1$ is

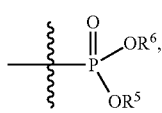

$R^5$ is —$CH_2$-phenyl substituted with 1 or 2 $R^{14}$, and $R^6$ is —$CH_2$-phenyl substituted with 1 or 2 $R^{14}$. In another embodiment is a compound of Formula (I) or (I'), or a pharmaceutically acceptable salt thereof, wherein $R^1$ is

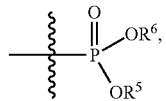

$R^5$ is unsubstituted $C_{2-9}$heteroaryl, and $R^6$ is unsubstituted $C_{2-9}$heteroaryl. In another embodiment is a compound of Formula (I) or (I'), or a pharmaceutically acceptable salt thereof, wherein $R^1$ is

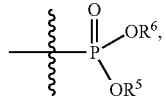

$R^5$ is $C_{2-9}$heteroaryl substituted with 1 or 2 $R^{14}$, and $R^6$ is $C_{2-9}$heteroaryl substituted with 1 or 2 $R^{14}$. In another embodiment is a compound of Formula (I) or (I'), or a pharmaceutically acceptable salt thereof, wherein $R^1$ is

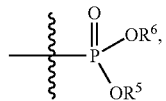

$R^5$ is unsubstituted —$C_{1-8}$alkyl-$C_{2-9}$heteroaryl, and $R^6$ is unsubstituted —$C_{1-8}$alkyl-$C_{2-9}$heteroaryl. In another embodiment is a compound of Formula (I) or (I'), or a pharmaceutically acceptable salt thereof, wherein $R^1$ is

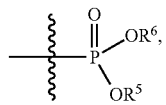

$R^5$ is —$C_{1-8}$alkyl-$C_{2-9}$heteroaryl substituted with 1 or 2 $R^{14}$, and $R^6$ is —$C_{1-8}$alkyl-$C_{2-9}$heteroaryl substituted with 1 or 2 $R^{14}$.

In another embodiment is a compound of Formula (I) or (I'), or a pharmaceutically acceptable salt thereof, wherein $R^1$ is

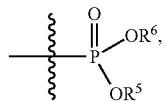

$R^5$ is H, and $R^6$ is $C_{3-18}$alkyl. In another embodiment is a compound of Formula (I) or (I'), or a pharmaceutically acceptable salt thereof, wherein $R^1$ is

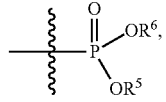

$R^5$ is H, and $R^6$ is $C_{6-15}$alkyl. In another embodiment is a compound of Formula (I) or (I'), or a pharmaceutically acceptable salt thereof, wherein $R^1$ is

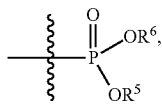

$R^5$ is H, and $R^6$ is $C_{6-10}$alkyl. In another embodiment is a compound of Formula (I) or (I'), or a pharmaceutically acceptable salt thereof, wherein $R^1$ is

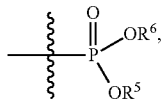

$R^5$ is H, and $R^6$ is $C_{3-18}$alkenyl. In another embodiment is a compound of Formula (I) or (I'), or a pharmaceutically acceptable salt thereof, wherein $R^1$ is

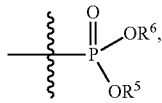

$R^5$ is H, and $R^6$ is $C_{6-15}$alkenyl. In another embodiment is a compound of Formula (I) or (I'), or a pharmaceutically acceptable salt thereof, wherein $R^1$ is

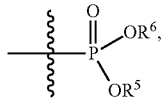

$R^5$ is H, and $R^6$ is $C_{6-10}$alkenyl. In another embodiment is a compound of Formula (I) or (I'), or a pharmaceutically acceptable salt thereof, wherein $R^1$ is

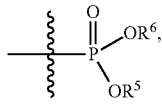

$R^5$ is H, and $R^6$ is $C_{3-18}$alkynyl. In another embodiment is a compound of Formula (I) or (I'), or a pharmaceutically acceptable salt thereof, wherein $R^1$ is

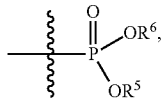

$R^5$ is H, and $R^6$ is $C_{6-15}$alkynyl. In another embodiment is a compound of Formula (I) or (I'), or a pharmaceutically acceptable salt thereof, wherein $R^1$ is

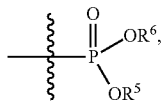

$R^5$ is H, and $R^6$ is $C_{6-10}$alkynyl. In another embodiment is a compound of Formula (I) or (I'), or a pharmaceutically acceptable salt thereof, wherein $R^1$ is

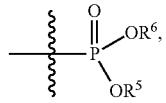

$R^5$ is H, and $R^6$ is $C_{3-18}$haloalkyl. In another embodiment is a compound of Formula (I) or (I'), or a pharmaceutically acceptable salt thereof, wherein $R^1$ is

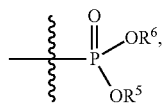

$R^5$ is H, and $R^6$ is $C_{6-15}$haloalkyl. In another embodiment is a compound of Formula (I) or (I'), or a pharmaceutically acceptable salt thereof, wherein $R^1$ is

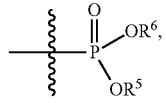

$R^5$ is H, and $R^6$ is $C_{6-10}$haloalkyl. In another embodiment is a compound of Formula (I) or (I'), or a pharmaceutically acceptable salt thereof, wherein $R^1$ is

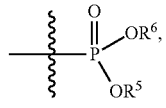

$R^5$ is H, and $R^6$ is —$C_{1-4}$alkyl-OC(O)$C_{1-8}$alkyl. In another embodiment is a compound of Formula (I) or (I'), or a pharmaceutically acceptable salt thereof, wherein $R^1$ is

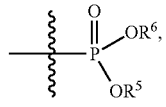

$R^5$ is H, and $R^6$ is —$C_{1-2}$alkyl-OC(O)$C_{1-8}$alkyl. In another embodiment is a compound of Formula (I) or (I'), or a pharmaceutically acceptable salt thereof, wherein $R^1$ is

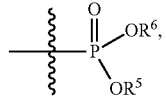

$R^5$ is H, and $R^6$ is -CH$_2$OC(O)$C_{1-8}$alkyl. In another embodiment is a compound of Formula (I) or (I'), or a pharmaceutically acceptable salt thereof, wherein $R^1$ is

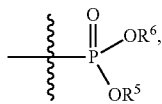

$R^5$ is H, and K is —$C_{1-4}$alkyl-OC(O)$C_{1-4}$alkyl. In another embodiment is a compound of Formula (I) or (I'), or a pharmaceutically acceptable salt thereof, wherein $R^1$ is

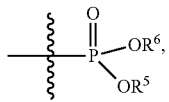

$R^5$ is H, and $R^6$ is —$C_{1-2}$alkyl-OC(O)$C_{1-4}$alkyl. In another embodiment is a compound of Formula (I) or (I'), or a pharmaceutically acceptable salt thereof, wherein $R^1$ is

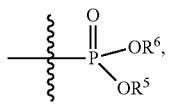

$R^5$ is H, and $R^6$ is —$CH_2OC(O)C_{1-4}$alkyl. In another embodiment is a compound of Formula (I) or (I'), or a pharmaceutically acceptable salt thereof, wherein $R^1$ is

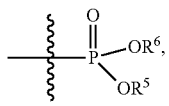

$R^5$ is H, and $R^6$ is —$C_{1-4}$alkyl-OC(O)C(CH$_3$)$_3$. In another embodiment is a compound of Formula (I) or (I'), or a pharmaceutically acceptable salt thereof, wherein $R^1$ is

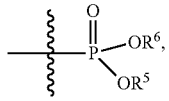

$R^5$ is H, and $R^6$ is —$C_{1-2}$alkyl-OC(O)C(CH$_3$)$_3$. In another embodiment is a compound of Formula (I) or (I'), or a pharmaceutically acceptable salt thereof, wherein $R^1$ is

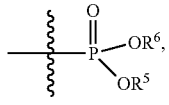

$R^5$ is H, and $R^6$ is —$CH_2OC(O)C(CH_3)_3$.

In another embodiment is a compound of Formula (I) or (I'), or a pharmaceutically acceptable salt thereof, wherein $R^1$ is

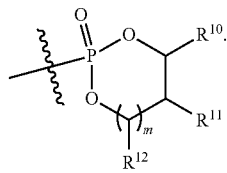

In another embodiment is a compound of Formula (I) or (I'), or a pharmaceutically acceptable salt thereof, wherein $R^1$ is

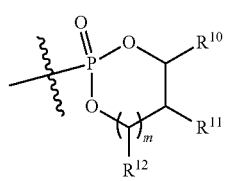

and m is 1. In another embodiment is a compound of Formula (I) or (I'), or a pharmaceutically acceptable salt thereof, wherein $R^1$ is

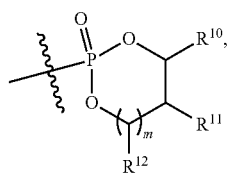

m is 1, and $R^{10}$, $R^{11}$ and $R^{12}$ are each H. In another embodiment is a compound of Formula (I) or (I'), or a pharmaceutically acceptable salt thereof, wherein $R^1$ is

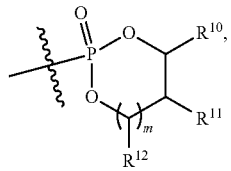

m is 1 and $R^{10}$, $R^{11}$ and $R^{12}$ are each $C_{1-12}$alkyl. In another embodiment is a compound of Formula (I) or (I'), or a pharmaceutically acceptable salt thereof, wherein $R^1$ is

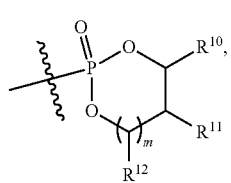

m is 1 and $R^{10}$, $R^{11}$ and $R^{12}$ are each $C_{1-4}$alkyl. In another embodiment is a compound of Formula (I) or (I'), or a pharmaceutically acceptable salt thereof, wherein $R^1$ is

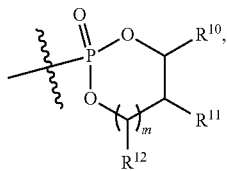

m is 1, and $R^{10}$, $R^{11}$ and $R^{12}$ are each —CH$_3$. In another embodiment is a compound of Formula (I) or (I'), or a pharmaceutically acceptable salt thereof, wherein $R^1$ is

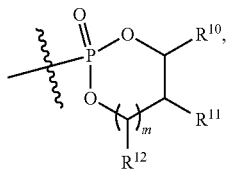

m is 1, $R^{10}$ is $C_{1-12}$alkyl, and $R^{11}$ and $R^{12}$ are each H. In another embodiment is a compound of Formula (I) or (I'), or a pharmaceutically acceptable salt thereof, wherein $R^1$ is

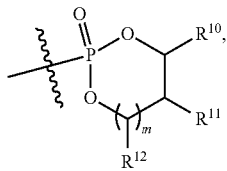

m is 1, $R^{10}$ is $C_{1-4}$alkyl, and $R^{11}$ and $R^{12}$ are each H. In another embodiment is a compound of Formula (I) or (I'), or a pharmaceutically acceptable salt thereof, wherein $R^1$ is

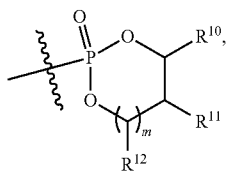

m is 1, $R^{10}$ is —CH$_3$, and $R^{11}$ and $R^{12}$ are each H. In another embodiment is a compound of Formula (I) or (I'), or a pharmaceutically acceptable salt thereof, wherein $R^1$ is

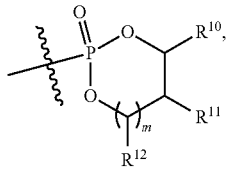

m is 1, $R^{10}$ is $C_{1-12}$alkyl, and $R^{10}$ and $R^{12}$ are each H. In another embodiment is a compound of Formula (I) or (I'), or a pharmaceutically acceptable salt thereof, wherein $R^1$ is

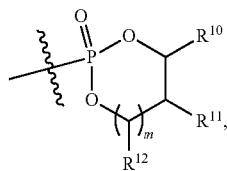

m is 1, $R^{11}$ is $C_{1-4}$alkyl, and $R^{10}$ and $R^{12}$ are each H. In another embodiment is a compound of Formula (I) or (I'), or a pharmaceutically acceptable salt thereof, wherein

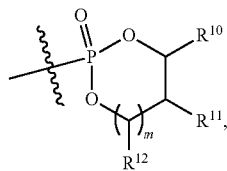

m is 1, $R^{11}$ is —CH$_3$, and $R^{10}$ and $R^{12}$ are each H. In another embodiment is a compound of Formula (I) or (I'), or a pharmaceutically acceptable salt thereof, wherein $R^1$ is

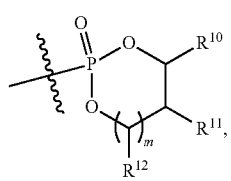

m is 1, $R^{10}$ is H, and $R^{11}$ and $R^{12}$ are each $C_{1-12}$alkyl. In another embodiment is a compound of Formula (I) or (I'), or a pharmaceutically acceptable salt thereof, wherein $R^1$ is

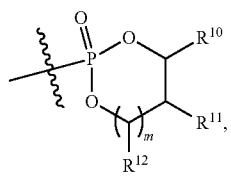

m is 1, $R^{10}$ is H, and $R^{11}$ and $R^{12}$ are each $C_{1-4}$alkyl. In another embodiment is a compound of Formula (I) or (I'), or a pharmaceutically acceptable salt thereof, wherein $R^1$ is

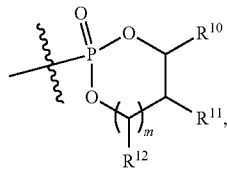

m is 1, $R^{10}$ is H, and $R^{11}$ and $R^{12}$ are each —CH$_3$. In another embodiment is a compound of Formula (I) or (I'), or a pharmaceutically acceptable salt thereof, wherein $R^1$ is

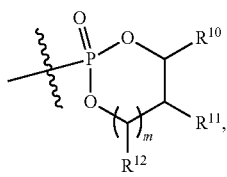

m is 1, $R^{11}$ is H, and $R^{10}$ and $R^{12}$ are each $C_{1-12}$alkyl. In another embodiment is a compound of Formula (I) or (I'), or a pharmaceutically acceptable salt thereof, wherein $R^1$ is

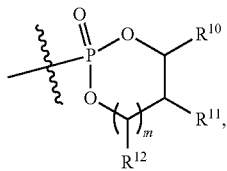

m is 1, $R^{11}$ is H, and $R^{10}$ and $R^{12}$ are each $C_{1-4}$alkyl. In another embodiment is a compound of Formula (I) or (I'), or a pharmaceutically acceptable salt thereof, wherein $R^1$ is

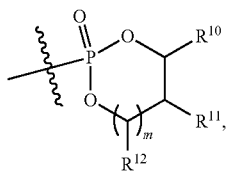

m is 1, $R^{11}$ is H, and $R^{10}$ and $R^{12}$ are each —$CH_3$. In another embodiment is a compound of Formula (I) or (I'), or a pharmaceutically acceptable salt thereof, wherein $R^1$ is

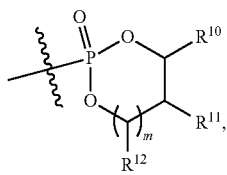

m is 1, R is H, and $R^{10}$ and $R^{11}$ form a 5- or 6-membered cycloalkyl ring or a 5- or 6-membered heterocycloalkyl ring, wherein the 5- or 6-membered cycloalkyl ring or the 5- or 6-membered heterocycloalkyl ring are optionally substituted with one or two $R^{13}$. In another embodiment is a compound of Formula (I) or (I'), or a pharmaceutically acceptable salt thereof, wherein $R^1$ is

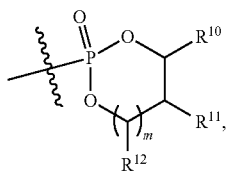

m is 1, $R^{12}$ is H, and $R^{10}$ and $R^{11}$ form a 5- or 6-membered cycloalkyl ring optionally substituted with one or two $R^{13}$. In another embodiment is a compound of Formula (I) or (I'), or a pharmaceutically acceptable salt thereof, wherein $R^1$ is

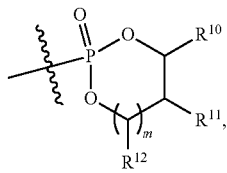

m is 1, $R^{12}$ is H, and $R^{10}$ and $R^{11}$ form a 5- or 6-membered heterocycloalkyl ring optionally substituted with one or two $R^{13}$. In another embodiment is a compound of Formula (I) or (I'), or a pharmaceutically acceptable salt thereof, wherein $R^1$ is

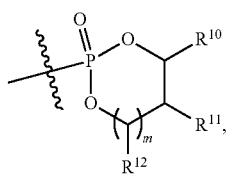

m is 1, $R^{12}$ is $C_{1-12}$alkyl, and $R^{10}$ and $R^{11}$ form a 5- or 6-membered cycloalkyl ring or a 5- or 6-membered heterocycloalkyl ring, wherein the 5- or 6-membered cycloalkyl ring or the 5- or 6-membered heterocycloalkyl ring are optionally substituted with one or two $R^{13}$. In another embodiment is a compound of Formula (I) or (I'), or a pharmaceutically acceptable salt thereof, wherein $R^1$ is

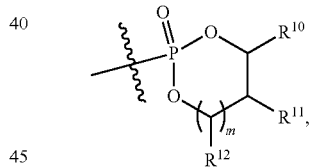

m is 1, $R^{12}$ is $C_{1-12}$alkyl, and $R^{10}$ and $R^{11}$ form a 5- or 6-membered cycloalkyl ring optionally substituted with one or two $R^{13}$. In another embodiment is a compound of Formula (I) or (I'), or a pharmaceutically acceptable salt thereof, wherein $R^1$ is

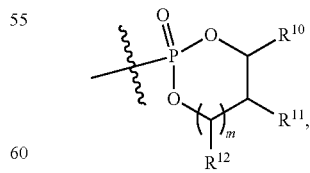

m is 1, $R^{12}$ is $C_{1-12}$alkyl, and $R^{10}$ and $R^{11}$ form a 5- or 6-membered heterocycloalkyl ring optionally substituted with one or two $R^{13}$. In another embodiment is a compound of Formula (I) or (I'), or a pharmaceutically acceptable salt thereof, wherein $R^1$ is

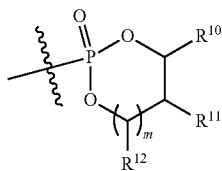

and m is 0. In another embodiment is a compound of Formula (I) or (I'), or a pharmaceutically acceptable salt thereof, wherein $R^1$ is

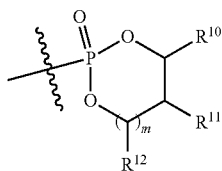

m is 0, and $R^{10}$ and $R^{11}$ are each H. In another embodiment is a compound of Formula (I) or (I'), or a pharmaceutically acceptable salt thereof, wherein $R^1$ is

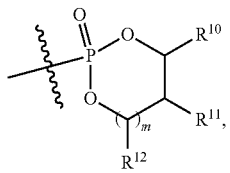

m is 0, and $R^{10}$ and $R^{11}$ are each $C_{1-12}$alkyl. In another embodiment is a compound of Formula (I) or (I'), or a pharmaceutically acceptable salt thereof, wherein $R^1$ is

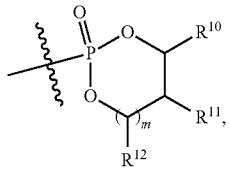

m is 0, and $R^{10}$ and $R^{11}$ are each $C_{1-4}$alkyl. In another embodiment is a compound of Formula (I) or (I'), or a pharmaceutically acceptable salt thereof, wherein $R^1$ is

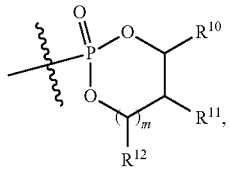

m is 0, and $R^{10}$ and $R^{11}$ are each —$CH_3$. In another embodiment is a compound of Formula (I) or (I'), or a pharmaceutically acceptable salt thereof, wherein $R^1$ is

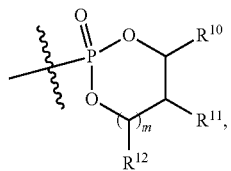

m is 0, $R^{10}$ is H, and $R^{11}$ is $C_{1-12}$alkyl. In another embodiment is a compound of Formula (I) or (I'), or a pharmaceutically acceptable salt thereof, wherein $R^1$ is

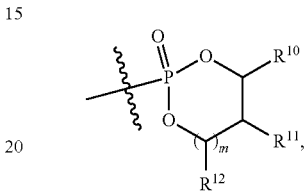

m is 0, $R^{10}$ is H, and $R^{11}$ is $C_{1-4}$alkyl. In another embodiment is a compound of Formula (I) or (I'), or a pharmaceutically acceptable salt thereof, wherein $R^1$ is

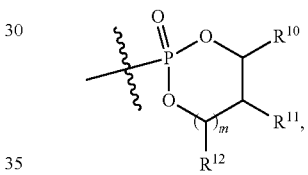

m is 0, $R^{10}$ is H, and $R^{11}$ is —$CH_3$. In another embodiment is a compound of Formula (I) or (I'), or a pharmaceutically acceptable salt thereof, wherein $R^1$ is

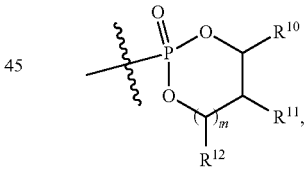

m is 0, $R^{10}$ is $C_{1-12}$alkyl, and $R^{11}$ is H. In another embodiment is a compound of Formula (I) or (I'), or a pharmaceutically acceptable salt thereof, wherein $R^1$ is

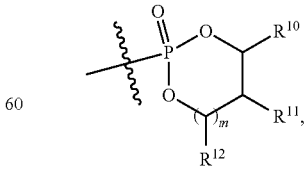

m is 0, $R^{10}$ is $C_{1-4}$alkyl, and $R^{11}$ is H. In another embodiment is a compound of Formula (I) or (I'), or a pharmaceutically acceptable salt thereof, wherein $R^1$ is

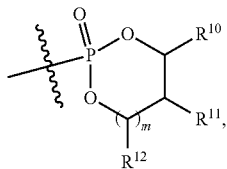

m is 0, $R^{10}$ is —$CH_3$, and $R^{11}$ is H. In another embodiment is a compound of Formula (I) or (I'), or a pharmaceutically acceptable salt thereof, wherein $R^1$ is

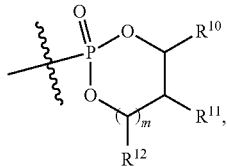

m is 0, and $R^{10}$ and $R^{11}$ form a 5- or 6-membered cycloalkyl ring or a 5- or 6-membered heterocycloalkyl ring, wherein the 5- or 6-membered cycloalkyl ring or the 5- or 6-membered heterocycloalkyl ring are optionally substituted with one or two $R^{13}$. In another embodiment is a compound of Formula (I) or (I'), or a pharmaceutically acceptable salt thereof, wherein $R^1$ is

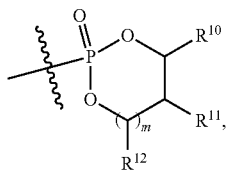

m is 0, and $R^{10}$ and $R^{11}$ form a 5- or 6-membered cycloalkyl ring optionally substituted with one or two $R^{13}$. In another embodiment is a compound of Formula (I) or (I'), or a pharmaceutically acceptable salt thereof, wherein $R^1$ is

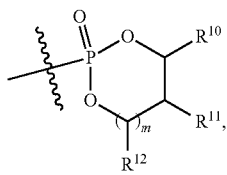

m is 0, and $R^{10}$ and $R^{11}$ form a 5- or 6-membered heterocycloalkyl ring optionally substituted with one or two $R^{13}$.

In another embodiment is a compound of Formula (I) or (I'), or a pharmaceutically acceptable salt thereof, wherein $R^1$ is

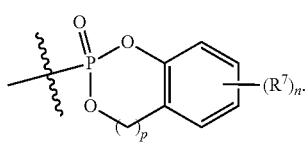

In another embodiment is a compound of Formula (I) or (I'), or a pharmaceutically acceptable salt thereof, wherein $R^1$ is

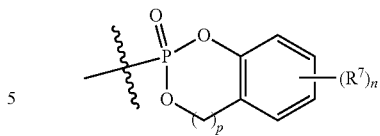

and p is 1. In another embodiment is a compound of Formula (I) or (I'), or a pharmaceutically acceptable salt thereof, wherein $R^1$ is

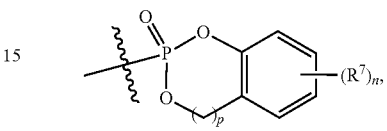

p is 1, and n is 0. In another embodiment is a compound of Formula (I) or (I'), or a pharmaceutically acceptable salt thereof, wherein $R^1$ is

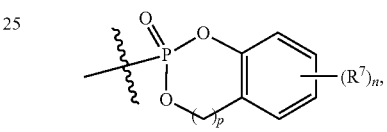

p is 1, and n is 1, 2, 3, or 4. In another embodiment is a compound of Formula (I) or (I'), or a pharmaceutically acceptable salt thereof, wherein $R^1$ is

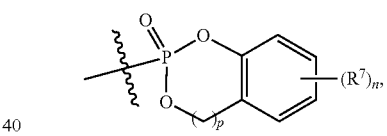

p is 1, and n is 1 or 2. In another embodiment is a compound of Formula (I) or (I'), or a pharmaceutically acceptable salt thereof, wherein $R^1$ is

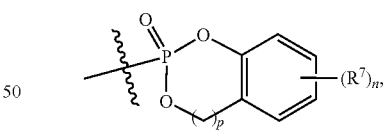

p is 1, and n is 1. In another embodiment is a compound of Formula (I) or (I'), or a pharmaceutically acceptable salt thereof, wherein $R^1$ is

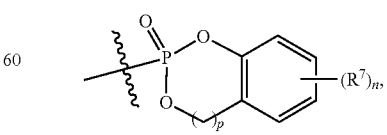

p is 1, n is 1, and $R^7$ is halogen. In another embodiment is a compound of Formula (I) or (I'), or a pharmaceutically acceptable salt thereof, wherein $R^1$ is

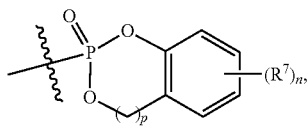

p is 1, n is 1, and R⁷ is $C_{1-8}$alkyl. In another embodiment is a compound of Formula (I) or (I'), or a pharmaceutically acceptable salt thereof, wherein R¹ is

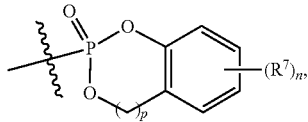

p is 1, n is 1, and R⁷ is $C_{1-8}$haloalkyl. In another embodiment is a compound of Formula (I) or (I'), or a pharmaceutically acceptable salt thereof, wherein R¹ is

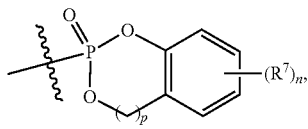

p is 1, n is 1, and R⁷ is $C_{1-8}$alkoxy. In another embodiment is a compound of Formula (I) or (I'), or a pharmaceutically acceptable salt thereof, wherein R¹ is

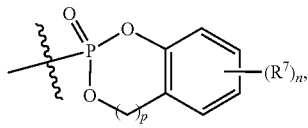

and p is 0. In another embodiment is a compound of Formula (I) or (I'), or a pharmaceutically acceptable salt thereof, wherein R¹ is

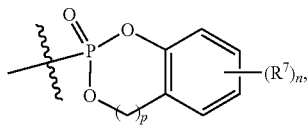

p is 0, and n is 0. In another embodiment is a compound of Formula (I) or (I'), or a pharmaceutically acceptable salt thereof, wherein R¹ is

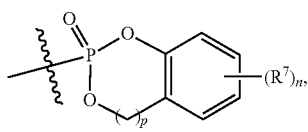

p is 0, and n is 1, 2, 3, or 4. In another embodiment is a compound of Formula (I) or (I'), or a pharmaceutically acceptable salt thereof, wherein R¹ is

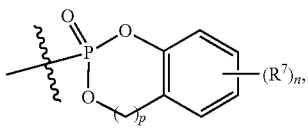

p is 0, and n is 1 or 2. In another embodiment is a compound of Formula (I) or (I'), or a pharmaceutically acceptable salt thereof, wherein R¹ is

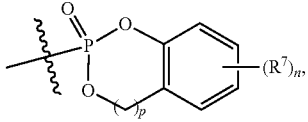

p is 0, and n is 1. In another embodiment is a compound of Formula (I) or (I'), or a pharmaceutically acceptable salt thereof, wherein R¹ is

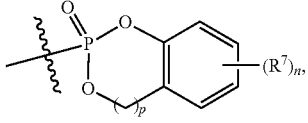

p is 0, n is 1, and R⁷ is halogen. In another embodiment is a compound of Formula (I) or (I'), or a pharmaceutically acceptable salt thereof, wherein R¹ is

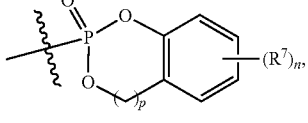

p is 0, n is 1, and R⁷ is $C_{1-8}$alkyl. In another embodiment is a compound of Formula (I) or (I'), or a pharmaceutically acceptable salt thereof, wherein R¹ is

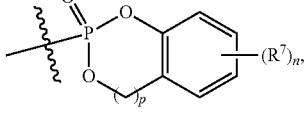

p is 0, n is 1, and R⁷ is $C_{1-8}$haloalkyl. In another embodiment is a compound of Formula (I) or (I'), or a pharmaceutically acceptable salt thereof, wherein R¹ is

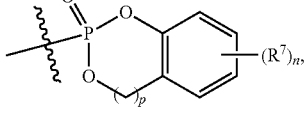

p is 0, n is 1, and R⁷ is $C_{1-8}$alkoxy.

In another embodiment is a compound of Formula (I) or (I'), or a pharmaceutically acceptable salt thereof, wherein R⁸ is $C_{3-18}$alkyl. In another embodiment is a compound of Formula (I) or (I'), or a pharmaceutically acceptable salt thereof, wherein $R^8$ is $C_{3-15}$alkyl. In another embodiment is a compound of Formula (I) or (I'), or a pharmaceutically acceptable salt thereof, wherein $R^8$ is $C_{3-12}$alkyl. In another embodiment is a compound of Formula (I) or (I'), or a pharmaceutically acceptable salt thereof, wherein $R^8$ is $C_{6-18}$alkyl. In another embodiment is a compound of Formula (I) or (I'), or a pharmaceutically acceptable salt thereof, wherein $R^8$ is $C_{6-12}$alkyl. In another embodiment is a compound of Formula (I) or (I'), or a pharmaceutically acceptable salt thereof, wherein $R^8$ is $C_{6-10}$alkyl. In another embodiment is a compound of Formula (I) or (I'), or a pharmaceutically acceptable salt thereof, wherein $R^8$ is $C_{8-10}$alkyl. In another embodiment is a compound of Formula (I) or (I'), or a pharmaceutically acceptable salt thereof, wherein $R^8$ is —$(CH_2)_2CH_3$. In another embodiment is a compound of Formula (I) or (I'), or a pharmaceutically acceptable salt thereof, wherein $R^8$ is —$(CH_2)_3CH_3$. In another embodiment is a compound of Formula (I) or (I'), or a pharmaceutically acceptable salt thereof, wherein $R^8$ is —$(CH_2)_4CH_3$. In another embodiment is a compound of Formula (I) or (I'), or a pharmaceutically acceptable salt thereof, wherein $R^8$ is —$(CH_2)_5CH_3$. In another embodiment is a compound of Formula (I) or (I'), or a pharmaceutically acceptable salt thereof, wherein $R^8$ is —$(CH_2)_6CH_3$. In another embodiment is a compound of Formula (I) or (I'), or a pharmaceutically acceptable salt thereof, wherein $R^8$ is —$(CH_2)_7CH_3$. In another embodiment is a compound of Formula (I) or (I'), or a pharmaceutically acceptable salt thereof, wherein $R^8$ is —$(CH_2)_8CH_3$. In another embodiment is a compound of Formula (I) or (I'), or a pharmaceutically acceptable salt thereof, wherein $R^8$ is —$(CH_2)_9CH_3$. In another embodiment is a compound of Formula (I) or (I'), or a pharmaceutically acceptable salt thereof, wherein $R^8$ is —$(CH_2)_{10}CH_3$. In another embodiment is a compound of Formula (I) or (I'), or a pharmaceutically acceptable salt thereof, wherein $R^8$ is —$(CH_2)_{11}CH_3$. In another embodiment is a compound of Formula (I) or (I'), or a pharmaceutically acceptable salt thereof, wherein $R^8$ is —$(CH_2)_{12}CH_3$. In another embodiment is a compound of Formula (I) or (I'), or a pharmaceutically acceptable salt thereof, wherein $R^8$ is —$(CH_2)_{13}CH_3$. In another embodiment is a compound of Formula (I) or (I'), or a pharmaceutically acceptable salt thereof, wherein $R^8$ is —$(CH_2)_{14}CH_3$. In another embodiment is a compound of Formula (I) or (I'), or a pharmaceutically acceptable salt thereof, wherein $R^8$ is —$(CH_2)_{15}CH_3$. In another embodiment is a compound of Formula (I) or (I'), or a pharmaceutically acceptable salt thereof, wherein $R^8$ is —$(CH_2)_{16}CH_3$. In another embodiment is a compound of Formula (I) or (I'), or a pharmaceutically acceptable salt thereof, wherein $R^8$ is —$(CH_2)_{17}CH_3$. In another embodiment is a compound of Formula (I) or (I'), or a pharmaceutically acceptable salt thereof, wherein $R^8$ is $C_{3-18}$alkenyl. In another embodiment is a compound of Formula (I) or (I'), or a pharmaceutically acceptable salt thereof, wherein $R^8$ is $C_{3-12}$alkenyl. In another embodiment is a compound of Formula (I) or (I'), or a pharmaceutically acceptable salt thereof, wherein $R^8$ is $C_{6-12}$alkenyl. In another embodiment is a compound of Formula (I) or (I'), or a pharmaceutically acceptable salt thereof, wherein $R^8$ is $C_{6-10}$alkenyl. In another embodiment is a compound of Formula (I) or (I'), or a pharmaceutically acceptable salt thereof, wherein $R^8$ is $C_{8-10}$alkenyl. In another embodiment is a compound of Formula (I) or (I'), or a pharmaceutically acceptable salt thereof, wherein $R^8$ is $C_{3-18}$alkynyl. In another embodiment is a compound of Formula (I) or (I'), or a pharmaceutically acceptable salt thereof, wherein $R^8$ is $C_{3-12}$alkynyl. In another embodiment is a compound of Formula (I) or (I'), or a pharmaceutically acceptable salt thereof, wherein $R^8$ is $C_{6-12}$alkynyl. In another embodiment is a compound of Formula (I) or (I'), or a pharmaceutically acceptable salt thereof, wherein $R^8$ is $C_{6-10}$alkynyl. In another embodiment is a compound of Formula (I) or (I'), or a pharmaceutically acceptable salt thereof, wherein $R^8$ is $C_{8-10}$alkynyl. In another embodiment is a compound of Formula (I) or (I'), or a pharmaceutically acceptable salt thereof, wherein $R^8$ is $C_{3-18}$haloalkyl. In another embodiment is a compound of Formula (I) or (I'), or a pharmaceutically acceptable salt thereof, wherein $R^8$ is $C_{3-12}$haloalkyl. In another embodiment is a compound of Formula (I) or (I'), or a pharmaceutically acceptable salt thereof, wherein $R^8$ is $C_{6-12}$haloalkyl. In another embodiment is a compound of Formula (I) or (I'), or a pharmaceutically acceptable salt thereof, wherein $R^8$ is $C_{6-10}$haloalkyl. In another embodiment is a compound of Formula (I) or (I'), or a pharmaceutically acceptable salt thereof, wherein $R^8$ is $C_{8-10}$haloalkyl. In another embodiment is a compound of Formula (I) or (I'), or a pharmaceutically acceptable salt thereof, wherein $R^8$ is $C_{3-8}$cycloalkyl. In another embodiment is a compound of Formula (I) or (I'), or a pharmaceutically acceptable salt thereof, wherein $R^8$ is $C_{3-6}$cycloalkyl. In another embodiment is a compound of Formula (I) or (I'), or a pharmaceutically acceptable salt thereof, wherein $R^8$ is $C_{6-10}$aryl optionally substituted with 1, 2, 3, or 4 $R^{14}$. In another embodiment is a compound of Formula (I) or (I'), or a pharmaceutically acceptable salt thereof, wherein $R^8$ is unsubstituted $C_{6-10}$aryl. In another embodiment is a compound of Formula (I) or (I'), or a pharmaceutically acceptable salt thereof, wherein $R^8$ is $C_{6-10}$aryl substituted with 1 or 2 $R^{14}$. In another embodiment is a compound of Formula (I) or (I'), or a pharmaceutically acceptable salt thereof, wherein $R^8$ is phenyl optionally substituted with 1, 2, 3, or 4 $R^{14}$. In another embodiment is a compound of Formula (I) or (I'), or a pharmaceutically acceptable salt thereof, wherein $R^8$ is unsubstituted phenyl. In another embodiment is a compound of Formula (I) or (I'), or a pharmaceutically acceptable salt thereof, wherein $R^8$ is phenyl substituted with 1 or 2 $R^{14}$. In another embodiment is a compound of Formula (I) or (I'), or a pharmaceutically acceptable salt thereof, wherein $R^8$ is —$C_{1-8}$alkyl-$C_{6-10}$aryl optionally substituted with 1, 2, 3, or 4 $R^{14}$. In another embodiment is a compound of Formula (I) or (I'), or a pharmaceutically acceptable salt thereof, wherein $R^8$ is unsubstituted —$C_{1-8}$alkyl-$C_{6-10}$aryl. In another embodiment is a compound of Formula (I) or (I'), or a pharmaceutically acceptable salt thereof, wherein $R^8$ is —$C_{1-8}$alkyl-$C_{6-10}$aryl substituted with 1 or 2 $R^{14}$. In another embodiment is a compound of Formula (I) or (I'), or a pharmaceutically acceptable salt thereof, wherein $R^8$ is —$CH_2$-phenyl optionally substituted with 1, 2, 3, or 4 $R^{14}$. In another embodiment is a compound of Formula (I) or (I'), or a pharmaceutically acceptable salt thereof, wherein $R^8$ is unsubstituted —$CH_2$-phenyl. In another embodiment is a compound of Formula (I) or (I'), or a pharmaceutically acceptable salt thereof, wherein $R^8$ is —$CH_2$-phenyl substituted with 1 or 2 $R^{14}$. In another embodiment is a compound of Formula (I) or (I'), or a pharmaceutically acceptable salt thereof, wherein $R^8$ is $C_{2-9}$heteroaryl optionally substituted with 1, 2, 3, or 4 $R^{14}$. In another embodiment is a compound of Formula (I) or (I'), or a pharmaceutically acceptable salt thereof, wherein $R^8$ is unsubstituted $C_{2-9}$heteroaryl. In another embodiment is a compound of Formula (I) or (I'), or a pharmaceutically acceptable salt thereof, wherein $R^8$ is $C_{2-9}$heteroaryl substituted with 1 or 2 $R^{14}$. In another embodiment is a compound of Formula (I) or (I'), or a pharmaceutically acceptable salt thereof, wherein $R^8$ is —$CH_2$—$C_{2-9}$heteroaryl optionally substituted with 1, 2, 3, or 4 $R^{14}$. In another embodiment is a compound of Formula (I) or (I'), or a pharmaceutically acceptable salt thereof, wherein $R^8$ is unsubstituted —$CH_2$—$C_{2-9}$heteroaryl. In another embodiment is a compound of Formula (I) or (I'), or a pharmaceutically acceptable salt thereof, wherein $R^8$ is —$CH_2$—$C_{2-9}$heteroaryl substituted with 1 or 2 $R^{14}$.

In another embodiment is a compound of Formula (I) or (I'), or a pharmaceutically acceptable salt thereof, wherein $R^3$ is H. In another embodiment is a compound of Formula (I) or (I'), or a pharmaceutically acceptable salt thereof, wherein $R^3$ is —C(O)$R^9$. In another embodiment is a compound of Formula (I) or (I'), or a pharmaceutically acceptable salt thereof, wherein $R^3$ is —C(O)$R^9$ and $R^9$ is $C_{1-10}$alkyl. In another embodiment is a compound of Formula (I) or (I'), or a pharmaceutically acceptable salt thereof, wherein $R^3$ is —C(O)$R^9$ and $R^9$ is $C_{1-6}$alkyl. In another embodiment is a compound of Formula (I) or (I'), or a pharmaceutically acceptable salt thereof, wherein $R^3$ is —C(O)$R^9$ and $R^9$ is $C_{1-4}$alkyl. In another embodiment is a compound of Formula (I) or (I'), or a pharmaceutically acceptable salt thereof, wherein $R^3$ is —C(O)$R^9$ and $R^9$ is —$CH_3$. In another embodiment is a compound of Formula (I) or (I'), or a pharmaceutically acceptable salt thereof, wherein $R^3$ is —C(O)$R^9$ and $R^9$ is —$CH_2CH_3$. In another embodiment is a compound of Formula (I) or (I'), or a pharmaceutically acceptable salt thereof, wherein $R^3$ is —C(O)O$R^9$. In another embodiment is a compound of Formula (I) or (I'), or a pharmaceutically acceptable salt thereof, wherein $R^3$ is —C(O)O$R^9$ and $R^9$ is $C_{1-10}$alkyl. In another embodiment is a compound of Formula (I) or (I'), or a pharmaceutically acceptable salt thereof, wherein $R^3$ is —C(O)O$R^9$ and $R^9$ is $C_{1-6}$alkyl. In another embodiment is a compound of Formula (I) or (I'), or a pharmaceutically acceptable salt thereof, wherein $R^3$ is —C(O)O$R^9$ and $R^9$ is $C_{1-4}$alkyl. In another embodiment is a compound of Formula (I) or (I'), or a pharmaceutically acceptable salt thereof, wherein $R^3$ is —C(O)O$R^9$ and $R^9$ is —$CH_3$. In another embodiment is a compound of Formula (I) or (I'), or a pharmaceutically acceptable salt thereof, wherein $R^3$ is —C(O)O$R^9$ and $R^9$ is —$CH_2CH_3$.

In some embodiments is a compound of Formula (I') having the structure of Formula (Ia):

Formula (Ia)

wherein:
$R^3$ is H, —C(O)$R^9$, or —C(O)O$R^9$;
$R^5$ is H, $C_{3-18}$alkyl, $C_{3-18}$alkenyl, $C_{3-18}$alkynyl, $C_{3-18}$haloalkyl, —$C_{1-4}$alkyl-OC(O)$C_{1-8}$alkyl, $C_{3-8}$cycloalkyl, $C_{6-10}$aryl, —$C_{1-8}$alkyl-$C_{6-10}$aryl, $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl, $C_{2-9}$heteroaryl, or —$C_{1-8}$alkyl-$C_{2-9}$heteroaryl are optionally substituted with 1, 2, 3, or 4 $R^{14}$;

$R^6$ is $C_{3-18}$alkyl, $C_{3-18}$alkenyl, $C_{3-18}$alkynyl, $C_{3-18}$haloalkyl, —$C_{1-4}$alkyl-OC(O)$C_{1-8}$alkyl, $C_{3-8}$cycloalkyl, $C_{6-10}$aryl, —$C_{1-8}$alkyl-$C_{6-10}$aryl $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl, $C_{2-9}$heteroaryl, or —$C_{1-8}$alkyl-$C_{2-9}$heteroaryl are optionally substituted with 1, 2, 3, or 4 $R^{14}$;

$R^8$ is $C_{3-18}$alkyl, $C_{3-18}$alkenyl, $C_{3-18}$alkynyl, $C_{3-18}$haloalkyl, $C_{3-8}$cycloalkyl, $C_{6-10}$aryl, —$C_{1-8}$alkyl-$C_{6-10}$aryl, $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl, $C_{2-9}$heteroaryl, or —$C_{1-8}$alkyl-$C_{2-9}$heteroaryl are optionally substituted with 1, 2, 3, or 4 $R^{14}$;

$R^9$ is $C_{1-12}$alkyl;
each $R^{13}$ is independently selected from $C_{1-12}$alkyl; and
each $R^{14}$ is independently selected from halogen, $C_{1-8}$alkyl, $C_{1-8}$haloalkyl, $C_{1-8}$alkoxy, and —C(O)$R^{13}$;
or a pharmaceutically acceptable salt thereof.

In another embodiment is a compound of Formula (Ia), or a pharmaceutically acceptable salt thereof, wherein $R^5$ is $C_{3-18}$alkyl and $R^6$ is $C_{3-18}$alkyl. In another embodiment is a compound of Formula (Ia), or a pharmaceutically acceptable salt thereof, wherein $R^5$ is $C_{3-15}$alkyl and $R^6$ is $C_{3-15}$alkyl. In another embodiment is a compound of Formula (Ia), or a pharmaceutically acceptable salt thereof, wherein $R^5$ is $C_{6-15}$alkyl and $R^6$ is $C_{6-15}$alkyl. In another embodiment is a compound of Formula (Ia), or a pharmaceutically acceptable salt thereof, wherein $R^5$ is $C_{6-12}$alkyl and $R^6$ is $C_{6-12}$alkyl. In another embodiment is a compound of Formula (Ia), or a pharmaceutically acceptable salt thereof, wherein $R^5$ is $C_{6-10}$alkyl and $R^6$ is $C_{6-10}$alkyl. In another embodiment is a compound of Formula (Ia), or a pharmaceutically acceptable salt thereof, wherein $R^5$ is $C_{3-18}$alkenyl and $R^6$ is $C_{3-18}$alkenyl. In another embodiment is a compound of Formula (Ia), or a pharmaceutically acceptable salt thereof, wherein $R^5$ is $C_{3-15}$alkenyl and $R^6$ is $C_{3-15}$alkenyl. In another embodiment is a compound of Formula (Ia), or a pharmaceutically acceptable salt thereof, wherein $R^5$ is $C_{6-15}$alkenyl and $R^6$ is $C_{6-15}$alkenyl. In another embodiment is a compound of Formula (Ia), or a pharmaceutically acceptable salt thereof, wherein $R^5$ is $C_{6-12}$alkenyl and $R^6$ is $C_{6-12}$alkenyl. In another embodiment is a compound of Formula (Ia), or a pharmaceutically acceptable salt thereof, wherein $R^5$ is $C_{6-10}$alkenyl and $R^6$ is $C_{6-10}$alkenyl. In another embodiment is a compound of Formula (Ia), or a pharmaceutically acceptable salt thereof, wherein $R^5$ is $C_{3-18}$alkynyl and $R^6$ is $C_{3-18}$alkynyl. In another embodiment is a compound of Formula (Ia), or a pharmaceutically acceptable salt thereof, wherein $R^5$ is $C_{3-15}$alkynyl and $R^6$ is $C_{3-15}$alkynyl. In another embodiment is a compound of Formula (Ia), or a pharmaceutically acceptable salt thereof, wherein $R^5$ is $C_{6-15}$alkynyl and $R^6$ is $C_{6-15}$alkynyl. In another embodiment is a compound of Formula (Ia), or a pharmaceutically acceptable salt thereof, wherein $R^5$ is $C_{6-12}$alkynyl and $R^6$ is $C_{6-12}$alkynyl. In another embodiment is a compound of Formula (Ia), or a pharmaceutically acceptable salt thereof, wherein $R^5$ is $C_{6-10}$alkynyl and $R^6$ is $C_{6-10}$alkynyl. In another embodiment is a compound of Formula (Ia), or a pharmaceutically acceptable salt thereof, wherein $R^5$ is $C_{3-18}$haloalkyl and $R^6$ is $C_{3-18}$haloalkyl. In another embodiment is a compound of Formula (Ia), or a pharmaceutically acceptable salt thereof, wherein $R^5$ is $C_{3-15}$haloalkyl and $R^6$ is $C_{3-15}$haloalkyl. In another embodiment is a compound of Formula (Ia), or a pharmaceutically acceptable salt thereof, wherein $R^5$ is $C_{6-15}$haloalkyl and $R^6$ is $C_{6-15}$haloalkyl. In another embodiment is a compound of Formula (Ia), or a pharmaceutically acceptable salt thereof, wherein $R^5$ is $C_{6-12}$haloalkyl and $R^6$ is $C_{6-12}$haloalkyl. In another embodiment is a compound of Formula (Ia), or a pharmaceutically acceptable salt thereof, wherein $R^5$ is $C_{6-10}$haloalkyl and $R^6$ is $C_{6-10}$haloalkyl. In another embodiment is a compound of Formula (Ia), or a pharmaceutically acceptable salt thereof, wherein $R^5$ is —$C_{1-4}$alkyl-OC(O)$C_{1-8}$alkyl and $R^6$ is —$C_{1-4}$alkyl-OC(O)$C_{1-8}$alkyl. In another embodiment is a compound of Formula (Ia), or a pharmaceutically acceptable salt thereof, wherein $R^5$ is —$C_{1-2}$alkyl-OC(O)$C_{1-8}$alkyl and $R^6$ is —$C_{1-2}$alkyl-OC(O)$C_{1-8}$alkyl. In another embodiment is a compound of Formula (Ia), or a pharmaceutically acceptable salt thereof, wherein $R^5$ is —$CH_2$OC(O)$C_{1-8}$alkyl and $R^6$ is —$CH_2$OC(O)$C_{1-8}$alkyl. In another embodiment is a compound of Formula (Ia), or a pharmaceutically acceptable salt thereof, wherein $R^5$ is —$C_{1-4}$alkyl-OC(O)$C_{1-6}$alkyl and $R^6$ is —$C_{1-4}$alkyl-OC(O)$C_{1-6}$alkyl. In another embodiment is a compound of Formula (Ia), or a pharmaceutically acceptable salt thereof, wherein $R^5$ is —$C_{1-2}$alkyl-OC(O)$C_{1-6}$alkyl and $R^6$ is —$C_{1-2}$alkyl-OC(O)$C_{1-6}$alkyl. In another embodiment is a compound of Formula (Ia), or a pharmaceutically acceptable salt thereof, wherein $R^5$ is —$CH_2$OC(O)$C_{1-6}$alkyl and $R^6$ is —$CH_2$OC(O)$C_{1-6}$alkyl. In another embodiment is a compound of Formula (Ia), or a pharmaceutically acceptable salt thereof, wherein $R^5$ is —$C_{1-4}$alkyl-OC(O)$C_{1-4}$alkyl and $R^6$ is —$C_{1-4}$alkyl-OC(O)$C_{1-4}$alkyl. In another embodiment is a compound of Formula (Ia), or a pharmaceutically acceptable salt thereof, wherein $R^5$ is —$C_{1-2}$alkyl-OC(O)$C_{1-4}$alkyl and $R^6$ is —$C_{1-2}$alkyl-OC(O)$C_{1-4}$alkyl. In another embodiment is a compound of Formula (Ia), or a pharmaceutically acceptable salt thereof, wherein $R^5$ is —$CH_2$OC(O)$C_{1-4}$alkyl and $R^6$ is —$CH_2$OC(O)$C_{1-4}$alkyl. In another embodiment is a compound of Formula (Ia), or a pharmaceutically acceptable salt thereof, wherein $R^5$ is —$C_{1-4}$alkyl-OC(O)C($CH_3$)$_3$ and $R^6$ is —$C_{1-4}$alkyl-OC(O)C($CH_3$)$_3$. In another embodiment is a compound of Formula (Ia), or a pharmaceutically acceptable salt thereof, wherein $R^5$ is —$C_{1-2}$alkyl-OC(O)C($CH_3$)$_3$ and $R^6$ is —$C_{1-2}$alkyl-OC(O)C($CH_3$)$_3$. In another embodiment is a compound of Formula (Ia), or a pharmaceutically acceptable salt thereof, wherein $R^5$ is —$CH_2$OC(O)C($CH_3$)$_3$, and $R^6$ is —$CH_2$OC(O)C($CH_3$)$_3$. In another embodiment is a compound of Formula (Ia), or a pharmaceutically acceptable salt thereof, wherein $R^5$ is $C_{3-8}$cycloalkyl and $R^6$ is $C_{3-8}$cycloalkyl. In another embodiment is a compound of Formula (Ia), or a pharmaceutically acceptable salt thereof, wherein $R^5$ is $C_{3-6}$cycloalkyl and $R^6$ is $C_{3-6}$cycloalkyl. In another embodiment is a compound of Formula (Ia), or a pharmaceutically acceptable salt thereof, wherein $R^5$ is unsubstituted $C_{6-10}$aryl and $R^6$ is unsubstituted $C_{6-10}$aryl. In another embodiment is a compound of Formula (Ia), or a pharmaceutically acceptable salt thereof, wherein $R^5$ is $C_{6-10}$aryl substituted with 1 or 2 $R^{14}$, and $R^6$ is $C_{6-10}$aryl substituted with 1 or 2 $R^{14}$. In another embodiment is a compound of Formula (Ia), or a pharmaceutically acceptable salt thereof, wherein $R^5$ is unsubstituted phenyl, and $R^6$ is unsubstituted phenyl. In another embodiment is a compound of Formula (Ia), or a pharmaceutically acceptable salt thereof, wherein $R^5$ is phenyl substituted with 1 or 2 $R^{14}$, and $R^6$ is phenyl substituted with 1 or 2 $R^{14}$. In another embodiment is a compound of Formula (Ia), or a pharmaceutically acceptable salt thereof, wherein $R^5$ is unsubstituted —$C_{1-8}$alkyl-$C_{6-10}$aryl, and $R^6$ is unsubstituted —$C_{1-8}$alkyl-$C_{6-10}$aryl. In another embodiment is a compound of Formula (Ia), or a pharmaceutically acceptable salt thereof, wherein $R^5$ is —$C_{1-8}$alkyl-$C_{6-10}$aryl substituted with 1 or 2 $R^{14}$, and $R^6$ is —$C_{1-8}$alkyl-$C_{6-10}$aryl substituted with 1 or 2 $R^{14}$. In another embodiment is a compound of Formula (Ia), or a pharmaceutically acceptable salt thereof, wherein $R^5$ is unsubstituted —$CH_2$— phenyl, and $R^6$ is unsubstituted —$CH_2$-phenyl. In another embodiment is a compound of Formula (Ia), or a pharmaceutically acceptable salt thereof, wherein $R^5$ is —$CH_2$-phenyl substituted with 1 or 2 $R^{14}$, and $R^6$ is —$CH_2$-phenyl substituted with 1 or 2 $R^{14}$. In another embodiment is a compound of Formula (Ia), or a pharmaceutically acceptable salt thereof, wherein $R^5$ is unsubstituted $C_{2-9}$heteroaryl, and $R^6$ is unsubstituted $C_{2-9}$heteroaryl. In another embodiment is a compound of Formula (Ia), or a pharmaceutically acceptable salt thereof, wherein $R^5$ is $C_{2-9}$heteroaryl substituted with 1 or 2 $R^{14}$, and $R^6$ is $C_{2-9}$heteroaryl substituted with 1 or 2 $R^{14}$. In another embodiment is a compound of Formula (Ia), or a pharmaceutically acceptable salt thereof, wherein $R^5$ is unsubstituted —$C_{1-8}$alkyl-$C_{2-9}$heteroaryl, and $R^6$ is unsubstituted —$C_{1-8}$alkyl-$C_{2-9}$heteroaryl. In another embodiment is a compound of Formula (Ia), or a pharmaceutically acceptable salt thereof, wherein $R^5$ is —$C_{1-8}$alkyl-$C_{2-9}$heteroaryl substituted with 1 or 2 $R^{10}$, and $R^6$ is —$C_{1-8}$alkyl-$C_{2-9}$heteroaryl substituted with 1 or 2 $R^{14}$.

In another embodiment is a compound of Formula (Ia), or a pharmaceutically acceptable salt thereof, wherein $R^5$ is H and $R^6$ is $C_{3-18}$alkyl. In another embodiment is a compound of Formula (Ia), or a pharmaceutically acceptable salt thereof, wherein $R^5$ is H and $R^6$ is $C_{6-15}$alkyl. In another embodiment is a compound of Formula (Ia), or a pharmaceutically acceptable salt thereof, wherein $R^5$ is H and $R^6$ is $C_{6-10}$alkyl. In another embodiment is a compound of Formula (Ia), or a pharmaceutically acceptable salt thereof, wherein $R^5$ is H and $R^6$ is $C_{3-18}$alkenyl. In another embodiment is a compound of Formula (Ia), or a pharmaceutically acceptable salt thereof, wherein $R^5$ is H and $R^6$ is $C_{6-15}$alkenyl. In another embodiment is a compound of Formula (Ia), or a pharmaceutically acceptable salt thereof, wherein $R^5$ is H and $R^6$ is $C_{6-10}$alkenyl. In another embodiment is a compound of Formula (Ia), or a pharmaceutically acceptable salt thereof, wherein $R^5$ is H and $R^6$ is $C_{3-18}$alkynyl. In another embodiment is a compound of Formula (Ia), or a pharmaceutically acceptable salt thereof, wherein $R^5$ is H and $R^6$ is $C_{6-15}$alkynyl. In another embodiment is a compound of Formula (Ia), or a pharmaceutically acceptable salt thereof, wherein $R^5$ is H and $R^6$ is $C_{6-10}$alkynyl. In another embodiment is a compound of Formula (Ia), or a pharmaceutically acceptable salt thereof, wherein $R^5$ is H and $R^6$ is $C_{3-18}$haloalkyl. In another embodiment is a compound of Formula (Ia), or a pharmaceutically acceptable salt thereof, wherein $R^5$ is H and $R^6$ is $C_{6-15}$haloalkyl. In another embodiment is a compound of Formula (Ia), or a pharmaceutically acceptable salt thereof, wherein $R^5$ is H and $R^6$ is $C_{6-10}$haloalkyl. In another embodiment is a compound of Formula (Ia), or a pharmaceutically acceptable salt thereof, wherein $R^5$ is H and $R^6$ is —$C_{1-4}$alkyl-OC(O)$C_{1-8}$alkyl. In another embodiment is a compound of Formula (Ia), or a pharmaceutically acceptable salt thereof, wherein $R^5$ is H and $R^6$ is —$C_{1-2}$alkyl-OC(O)$C_{1-8}$alkyl. In another embodiment is a compound of Formula (Ia), or a pharmaceutically acceptable salt thereof, wherein $R^5$ is H and $R^6$ is —$CH_2$OC(O)$C_{1-8}$alkyl. In another embodiment is a compound of Formula (Ia), or a pharmaceutically acceptable salt thereof, wherein $R^5$ is H and $R^6$ is —$C_{1-4}$alkyl-OC(O)$C_{1-4}$alkyl. In another embodiment is a compound of Formula (Ia), or a pharmaceutically acceptable salt thereof, wherein $R^5$ is H and $R^6$ is —$C_{1-2}$alkyl-OC(O)$C_{1-4}$alkyl. In another embodiment is a compound of Formula (Ia), or a pharmaceutically acceptable salt thereof, wherein $R^5$ is H and $R^6$ is —$CH_2$OC(O)$C_{1-4}$alkyl. In another embodiment is a compound of Formula (Ia), or a pharmaceutically acceptable salt thereof, wherein $R^5$ is H and $R^6$ is —$C_{1-4}$alkyl-OC(O)C(CH$_3$)$_3$. In another embodiment is a compound of Formula (Ia), or a pharmaceutically acceptable salt thereof, wherein $R^5$ is H and $R^6$ is —$C_{1-2}$alkyl-OC(O)C(CH$_3$)$_3$. In another embodiment is a compound of Formula (Ia), or a pharmaceutically acceptable salt thereof, wherein $R^5$ is H and $R^6$ is —CH$_2$OC(O)C(CH$_3$)$_3$.

In another embodiment is a compound of Formula (Ia), or a pharmaceutically acceptable salt thereof, wherein $R^8$ is $C_{3-18}$alkyl. In another embodiment is a compound of Formula (Ia), or a pharmaceutically acceptable salt thereof, wherein $R^8$ is $C_{3-12}$alkyl. In another embodiment is a compound of Formula (Ia), or a pharmaceutically acceptable salt thereof, wherein $R^8$ is $C_{6-12}$alkyl. In another embodiment is a compound of Formula (Ia), or a pharmaceutically acceptable salt thereof, wherein $R^8$ is $C_{6-10}$alkyl. In another embodiment is a compound of Formula (Ia), or a pharmaceutically acceptable salt thereof, wherein $R^8$ is $C_{8-10}$alkyl. In another embodiment is a compound of Formula (Ia), or a pharmaceutically acceptable salt thereof, wherein $R^8$ is —(CH$_2$)$_2$CH$_3$. In another embodiment is a compound of Formula (Ia), or a pharmaceutically acceptable salt thereof, wherein $R^8$ is —(CH$_2$)$_3$CH$_3$. In another embodiment is a compound of Formula (Ia), or a pharmaceutically acceptable salt thereof, wherein $R^8$ is —(CH$_2$)$_4$CH$_3$. In another embodiment is a compound of Formula (Ia), or a pharmaceutically acceptable salt thereof, wherein $R^8$ is —(CH$_2$)$_5$CH$_3$. In another embodiment is a compound of Formula (Ia), or a pharmaceutically acceptable salt thereof, wherein $R^8$ is —(CH$_2$)$_6$CH$_3$. In another embodiment is a compound of Formula (Ia), or a pharmaceutically acceptable salt thereof, wherein $R^8$ is —(CH$_2$)$_7$CH$_3$. In another embodiment is a compound of Formula (Ia), or a pharmaceutically acceptable salt thereof, wherein $R^8$ is —(CH$_2$)$_8$CH$_3$. In another embodiment is a compound of Formula (Ia), or a pharmaceutically acceptable salt thereof, wherein $R^8$ is —(CH$_2$)$_9$CH$_3$. In another embodiment is a compound of Formula (Ia), or a pharmaceutically acceptable salt thereof, wherein $R^8$ is —(CH$_2$)$_{10}$CH$_3$. In another embodiment is a compound of Formula (Ia), or a pharmaceutically acceptable salt thereof, wherein $R^8$ is —(CH$_2$)$_{11}$CH$_3$. In another embodiment is a compound of Formula (Ia), or a pharmaceutically acceptable salt thereof, wherein $R^8$ is —(CH$_2$)$_{12}$CH$_3$. In another embodiment is a compound of Formula (Ia), or a pharmaceutically acceptable salt thereof, wherein $R^8$ is —(CH$_2$)$_{13}$CH$_3$. In another embodiment is a compound of Formula (Ia), or a pharmaceutically acceptable salt thereof, wherein $R^8$ is —(CH$_2$)$_{14}$CH$_3$. In another embodiment is a compound of Formula (Ia), or a pharmaceutically acceptable salt thereof, wherein $R^8$ is —(CH$_2$)$_{15}$CH$_3$. In another embodiment is a compound of Formula (Ia), or a pharmaceutically acceptable salt thereof, wherein $R^8$ is —(CH$_2$)$_{16}$CH$_3$. In another embodiment is a compound of Formula (Ia), or a pharmaceutically acceptable salt thereof, wherein $R^8$ is —(CH$_2$)$_{17}$CH$_3$. In another embodiment is a compound of Formula (Ia), or a pharmaceutically acceptable salt thereof, wherein $R^8$ is $C_{3-18}$alkenyl. In another embodiment is a compound of Formula (Ia), or a pharmaceutically acceptable salt thereof, wherein $R^8$ is $C_{3-12}$alkenyl. In another embodiment is a compound of Formula (Ia), or a pharmaceutically acceptable salt thereof, wherein $R^8$ is $C_{6-12}$alkenyl. In another embodiment is a compound of Formula (Ia), or a pharmaceutically acceptable salt thereof, wherein $R^8$ is $C_{6-10}$alkenyl. In another embodiment is a compound of Formula (Ia), or a pharmaceutically acceptable salt thereof, wherein $R^8$ is $C_{8-10}$alkenyl. In another embodiment is a compound of Formula (Ia), or a pharmaceutically acceptable salt thereof, wherein $R^8$ is $C_{3-18}$alkynyl. In another embodiment is a compound of Formula (Ia), or a pharmaceutically acceptable salt thereof, wherein $R^8$ is $C_{3-12}$alkynyl. In another embodiment is a compound of Formula (Ia), or a pharmaceutically acceptable salt thereof, wherein $R^8$ is $C_{6-12}$alkynyl. In another embodiment is a compound of Formula (Ia), or a pharmaceutically acceptable salt thereof, wherein $R^8$ is $C_{6-10}$alkynyl. In another embodiment is a compound of Formula (Ia), or a pharmaceutically acceptable salt thereof, wherein $R^8$ is $C_{8-10}$alkynyl. In another embodiment is a compound of Formula (Ia), or a pharmaceutically acceptable salt thereof, wherein $R^8$ is $C_{3-18}$haloalkyl. In another embodiment is a compound of Formula (Ia), or a pharmaceutically acceptable salt thereof, wherein $R^8$ is $C_{3-12}$haloalkyl. In another embodiment is a compound of Formula (Ia), or a pharmaceutically acceptable salt thereof, wherein $R^8$ is $C_{6-12}$haloalkyl. In another embodiment is a compound of Formula (Ia), or a pharmaceutically acceptable salt thereof, wherein $R^8$ is $C_{6-10}$haloalkyl. In another embodiment is a compound of Formula (Ia), or a pharmaceutically acceptable salt thereof, wherein $R^8$ is $C_{8-10}$haloalkyl. In another embodiment is a compound of Formula (Ia), or a pharmaceutically acceptable salt thereof, wherein $R^8$ is $C_{3-8}$cycloalkyl. In another embodiment is a compound of Formula (Ia), or a pharmaceutically acceptable salt thereof, wherein $R^8$ is $C_{3-6}$cycloalkyl. In another embodiment is a compound of Formula (Ia), or a pharmaceutically acceptable salt thereof, wherein $R^8$ is $C_{6-10}$aryl optionally substituted with 1, 2, 3, or 4 $R^{14}$. In another embodiment is a compound of Formula (Ia), or a pharmaceutically acceptable salt thereof, wherein $R^8$ is unsubstituted $C_{6-10}$aryl. In another embodiment is a compound of Formula (Ia), or a pharmaceutically acceptable salt thereof, wherein $R^8$ is $C_{6-10}$aryl substituted with 1 or 2 $R^{14}$. In another embodiment is a compound of Formula (Ia), or a pharmaceutically acceptable salt thereof, wherein $R^8$ is phenyl optionally substituted with 1, 2, 3, or 4 $R^{14}$. In another embodiment is a compound of Formula (Ia), or a pharmaceutically acceptable salt thereof, wherein $R^8$ is unsubstituted phenyl. In another embodiment is a compound of Formula (Ia), or a pharmaceutically acceptable salt thereof, wherein $R^8$ is phenyl substituted with 1 or 2 $R^{14}$. In another embodiment is a compound of Formula (Ia), or a pharmaceutically acceptable salt thereof, wherein $R^8$ is —$C_{1-8}$alkyl-$C_{6-10}$aryl optionally substituted with 1, 2, 3, or 4 $R^{14}$. In another embodiment is a compound of Formula (Ia), or a pharmaceutically acceptable salt thereof, wherein $R^8$ is unsubstituted —$C_{1-8}$alkyl-$C_{6-10}$aryl. In another embodiment is a compound of Formula (Ia), or a pharmaceutically acceptable salt thereof, wherein $R^8$ is —$C_{1-8}$alkyl-$C_{6-10}$aryl substituted with 1 or 2 $R^{14}$. In another embodiment is a compound of Formula (Ia), or a pharmaceutically acceptable salt thereof, wherein $R^8$ is —CH$_2$-phenyl optionally substituted with 1, 2, 3, or 4 $R^{14}$. In another embodiment is a compound of Formula (Ia), or a pharmaceutically acceptable salt thereof, wherein $R^8$ is unsubstituted —CH$_2$-phenyl. In another embodiment is a compound of Formula (Ia), or a pharmaceutically acceptable salt thereof, wherein $R^8$ is —CH$_2$-phenyl substituted with 1 or 2 $R^{14}$. In another embodiment is a compound of Formula (Ia), or a pharmaceutically acceptable salt thereof, wherein $R^8$ is $C_{2-9}$heteroaryl optionally substituted with 1, 2, 3, or 4 $R^{14}$. In another embodiment is a compound of Formula (Ia), or a pharmaceutically acceptable salt thereof, wherein $R^8$ is unsubstituted $C_{2-9}$heteroaryl. In another embodiment is a compound of Formula (Ia), or a pharmaceutically acceptable salt thereof, wherein $R^8$ is $C_{2-9}$heteroaryl substituted with 1 or 2 $R^{14}$. In another embodiment is a compound of Formula (Ia), or a pharmaceutically acceptable salt thereof, wherein $R^8$ is —$CH_2$—$C_{2-9}$heteroaryl optionally substituted with 1, 2, 3, or 4 $R^{14}$. In another embodiment is a compound of Formula (Ia), or a pharmaceutically acceptable salt thereof, wherein $R^8$ is unsubstituted —$CH_2$—$C_{2-9}$heteroaryl. In another embodiment is a compound of Formula (Ia), or a pharmaceutically acceptable salt thereof, wherein $R^8$ is —$CH_2$—$C_{2-9}$heteroaryl substituted with 1 or 2 $R^{14}$.

In another embodiment is a compound of Formula (Ia), or a pharmaceutically acceptable salt thereof, wherein $R^3$ is H, —$C(O)R^9$, or —$C(O)OR^9$. In another embodiment is a compound of Formula (Ia), or a pharmaceutically acceptable salt thereof, wherein $R^3$ is —$C(O)R^9$. In another embodiment is a compound of Formula (Ia), or a pharmaceutically acceptable salt thereof, wherein $R^3$ is —$C(O)R^9$ and $R^9$ is $C_{1-10}$alkyl. In another embodiment is a compound of Formula (Ia), or a pharmaceutically acceptable salt thereof, wherein $R^3$ is —$C(O)R^9$ and $R^9$ is $C_{1-6}$alkyl. In another embodiment is a compound of Formula (Ia), or a pharmaceutically acceptable salt thereof, wherein $R^3$ is —$C(O)R^9$ and $R^9$ is $C_{1-4}$alkyl. In another embodiment is a compound of Formula (Ia), or a pharmaceutically acceptable salt thereof, wherein $R^3$ is —$C(O)R^9$ and $R^9$ is —$CH_3$. In another embodiment is a compound of Formula (Ia), or a pharmaceutically acceptable salt thereof, wherein $R^3$ is —$C(O)R^9$ and $R^9$ is —$CH_2CH_3$. In another embodiment is a compound of Formula (Ia), or a pharmaceutically acceptable salt thereof, wherein $R^3$ is —$C(O)OR^9$. In another embodiment is a compound of Formula (Ia), or a pharmaceutically acceptable salt thereof, wherein $R^3$ is —$C(O)OR^9$ and $R^9$ is $C_{1-10}$alkyl. In another embodiment is a compound of Formula (Ia), or a pharmaceutically acceptable salt thereof, wherein $R^3$ is —$C(O)OR^9$ and $R^9$ is $C_{1-6}$alkyl. In another embodiment is a compound of Formula (Ia), or a pharmaceutically acceptable salt thereof, wherein $R^3$ is —$C(O)OR^9$ and $R^9$ is $C_{1-4}$alkyl. In another embodiment is a compound of Formula (Ia), or a pharmaceutically acceptable salt thereof, wherein $R^3$ is —$C(O)OR^9$ and $R^9$ is —$CH_3$. In another embodiment is a compound of Formula (Ia), or a pharmaceutically acceptable salt thereof, wherein $R^3$ is —$C(O)OR^9$ and $R^9$ is —$CH_2CH_3$.

In some embodiments is a compound of Formula (I') having the structure of Formula (Ib):

Formula (Ib)

wherein:
$R^3$ is H, —$C(O)R^9$, or —$C(O)OR^9$;
$R^8$ is $C_{3-18}$alkyl, $C_{3-18}$alkenyl, $C_{3-18}$alkynyl, $C_{3-18}$haloalkyl, $C_{3-8}$cycloalkyl, $C_{6-10}$aryl, —$C_{1-8}$alkyl-$C_{6-10}$aryl $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl $C_{2-9}$heteroaryl, or —$C_{1-8}$alkyl-$C_{2-9}$heteroaryl are optionally substituted with 1, 2, 3, or 4 $R^{14}$;
$R^9$ is $C_{1-12}$alkyl;
$R^{10}$ and $R^{11}$ are each independently H or $C_{1-12}$alkyl; or $R^{10}$ and $R^{11}$ form a 5- or 6-membered cycloalkyl ring or a 5- or 6-membered heterocycloalkyl ring, wherein the 5- or 6-membered cycloalkyl ring or the 5- or 6-membered heterocycloalkyl ring are optionally substituted with one or two $R^{13}$;
$R^{12}$ is H or $C_{1-12}$alkyl;
each $R^{13}$ is independently selected from $C_{1-12}$alkyl;
each $R^{14}$ is independently selected from halogen, $C_{1-8}$alkyl, $C_{1-8}$haloalkyl, $C_{1-8}$alkoxy, and —$C(O)R^{13}$; and
m is 0 or 1;
or a pharmaceutically acceptable salt thereof.

In another embodiment is a compound of Formula (Ib), or a pharmaceutically acceptable salt thereof, wherein m is 1. In another embodiment is a compound of Formula (Ib), or a pharmaceutically acceptable salt thereof, wherein m is 1 and $R^{10}$, $R^{11}$ and $R^{12}$ are each H. In another embodiment is a compound of Formula (Ib), or a pharmaceutically acceptable salt thereof, wherein m is 1 and $R^{10}$, $R^{11}$ and $R^{12}$ are each $C_{1-12}$alkyl. In another embodiment is a compound of Formula (Ib), or a pharmaceutically acceptable salt thereof, wherein m is 1 and $R^{10}$, $R^{11}$ and $R^{12}$ are each $C_{1-4}$alkyl. In another embodiment is a compound of Formula (Ib), or a pharmaceutically acceptable salt thereof, wherein m is 1 and $R^{10}$, $R^{11}$ and $R^{12}$ are each —$CH_3$. In another embodiment is a compound of Formula (Ib), or a pharmaceutically acceptable salt thereof, wherein m is 1, $R^{10}$ is $C_{1-12}$alkyl, and $R^{11}$ and $R^{12}$ are each H. In another embodiment is a compound of Formula (Ib), or a pharmaceutically acceptable salt thereof, wherein m is 1, $R^{10}$ is $C_{1-4}$alkyl, and $R^{11}$ and $R^{12}$ are each H. In another embodiment is a compound of Formula (Ib), or a pharmaceutically acceptable salt thereof, wherein m is 1, $R^{10}$ is —$CH_3$, and $R^{11}$ and $R^{12}$ are each H. In another embodiment is a compound of Formula (Ib), or a pharmaceutically acceptable salt thereof, wherein m is 1, $R^{11}$ is $C_{1-12}$alkyl, and $R^{10}$ and $R^{12}$ are each H. In another embodiment is a compound of Formula (Ib), or a pharmaceutically acceptable salt thereof, wherein m is 1, $R^{11}$ is $C_{1-4}$alkyl, and $R^{10}$ and $R^{12}$ are each H. In another embodiment is a compound of Formula (Ib), or a pharmaceutically acceptable salt thereof, wherein m is 1, $R^{11}$ is —$CH_3$, and $R^{10}$ and $R^{12}$ are each H. In another embodiment is a compound of Formula (Ib), or a pharmaceutically acceptable salt thereof, wherein m is 1, $R^{10}$ is H, and $R^{11}$ and $R^{12}$ are each $C_{1-12}$alkyl. In another embodiment is a compound of Formula (Ib), or a pharmaceutically acceptable salt thereof, wherein m is 1, $R^{10}$ is H, and $R^{11}$ and $R^{12}$ are each $C_{1-4}$alkyl. In another embodiment is a compound of Formula (Ib), or a pharmaceutically acceptable salt thereof, wherein m is 1, $R^{10}$ is H, and $R^{11}$ and $R^{12}$ are each —$CH_3$. In another embodiment is a compound of Formula (Ib), or a pharmaceutically acceptable salt thereof, wherein m is 1, $R^{11}$ is H, and $R^{10}$ and $R^{12}$ are each $C_{1-12}$alkyl. In another embodiment is a compound of Formula (Ib), or a pharmaceutically acceptable salt thereof, wherein m is 1, $R^{11}$ is H, and $R^{10}$ and $R^{12}$ are each $C_{1-4}$alkyl. In another embodiment is a compound of Formula (Ib), or a pharmaceutically acceptable salt thereof, wherein m is 1, $R^{11}$ is H, and $R^{10}$ and $R^{12}$ are each —$CH_3$. In another embodiment is a compound of Formula (Ib), or a pharmaceutically acceptable salt thereof, wherein m is 1, $R^{12}$ is H, and $R^{10}$ and $R^{11}$ form a 5- or 6-membered cycloalkyl ring or a 5- or 6-membered heterocycloalkyl ring, wherein the 5- or 6-membered cycloalkyl ring or the 5- or 6-membered heterocycloalkyl ring are optionally substituted with one or two $R^{13}$. In another embodiment is a compound of Formula (Ib), or a pharmaceutically acceptable salt thereof, wherein m is 1, $R^{12}$ is H, and $R^{10}$ and $R^{11}$ form a 5- or 6-membered cycloalkyl ring optionally substituted with one or two $R^{13}$. In another embodiment is a compound of Formula (Ib), or a pharmaceutically acceptable salt thereof, wherein m is 1, $R^{12}$ is H, and $R^{10}$ and $R^{11}$ form a 5- or 6-membered heterocycloalkyl ring optionally substituted with one or two $R^{13}$. In another embodiment is a compound of Formula (Ib), or a pharmaceutically acceptable salt thereof, wherein m is 1, $R^{12}$ is $C_{1-12}$alkyl, and $R^{10}$ and $R^{11}$ form a 5- or 6-membered cycloalkyl ring or a 5- or 6-membered heterocycloalkyl ring, wherein the 5- or 6-membered cycloalkyl ring or the 5- or 6-membered heterocycloalkyl ring are optionally substituted with one or two $R^{13}$. In another embodiment is a compound of Formula (Ib), or a pharmaceutically acceptable salt thereof, wherein m is 1, $R^{12}$ is $C_{1-12}$alkyl, and $R^{10}$ and $R^{11}$ form a 5- or 6-membered cycloalkyl ring optionally substituted with one or two $R^{13}$. In another embodiment is a compound of Formula (Ib), or a pharmaceutically acceptable salt thereof, wherein m is 1, $R^{12}$ is $C_{1-12}$alkyl, and $R^{10}$ and $R^{11}$ form a 5- or 6-membered heterocycloalkyl ring optionally substituted with one or two $R^{13}$. In another embodiment is a compound of Formula (Ib), or a pharmaceutically acceptable salt thereof, wherein m is 0. In another embodiment is a compound of Formula (Ib), or a pharmaceutically acceptable salt thereof, wherein m is 0 and $R^{10}$ and $R^{11}$ are each H. In another embodiment is a compound of Formula (Ib), or a pharmaceutically acceptable salt thereof, wherein m is 0 and $R^{10}$ and $R^{11}$ are each $C_{1-12}$alkyl. In another embodiment is a compound of Formula (Ib), or a pharmaceutically acceptable salt thereof, wherein m is 0 and $R^{10}$ and $R^{11}$ are each $C_{1-4}$alkyl. In another embodiment is a compound of Formula (Ib), or a pharmaceutically acceptable salt thereof, wherein m is 0 and $R^{10}$ and $R^{11}$ are each $-CH_3$. In another embodiment is a compound of Formula (Ib), or a pharmaceutically acceptable salt thereof, wherein m is 0, $R^{10}$ is H, and $R^{11}$ is $C_{1-12}$alkyl. In another embodiment is a compound of Formula (Ib), or a pharmaceutically acceptable salt thereof, wherein m is 0, $R^{10}$ is H, and $R^{11}$ is $C_{1-4}$alkyl. In another embodiment is a compound of Formula (Ib), or a pharmaceutically acceptable salt thereof, wherein m is 0, $R^{10}$ is H, and $R^{11}$ is $-CH_3$. In another embodiment is a compound of Formula (Ib), or a pharmaceutically acceptable salt thereof, wherein m is 0, $R^{10}$ is $C_{1-12}$alkyl, and $R^{11}$ is H. In another embodiment is a compound of Formula (Ib), or a pharmaceutically acceptable salt thereof, wherein m is 0, $R^{10}$ is $C_{1-4}$alkyl, and $R^{11}$ is H. In another embodiment is a compound of Formula (Ib), or a pharmaceutically acceptable salt thereof, wherein m is 0, $R^{10}$ is $-CH_3$, and $R^{11}$ is H. In another embodiment is a compound of Formula (Ib), or a pharmaceutically acceptable salt thereof, wherein m is 0, and $R^{10}$ and $R^{11}$ form a 5- or 6-membered cycloalkyl ring or a 5- or 6-membered heterocycloalkyl ring, wherein the 5- or 6-membered cycloalkyl ring or the 5- or 6-membered heterocycloalkyl ring are optionally substituted with one or two $R^{13}$. In another embodiment is a compound of Formula (Ib), or a pharmaceutically acceptable salt thereof, wherein m is 0, and $R^{10}$ and $R^{11}$ form a 5- or 6-membered cycloalkyl ring optionally substituted with one or two $R^{13}$. In another embodiment is a compound of Formula (Ib), or a pharmaceutically acceptable salt thereof, wherein m is 0, and $R^{10}$ and $R^{11}$ form a 5- or 6-membered heterocycloalkyl ring optionally substituted with one or two $R^{13}$.

In another embodiment is a compound of Formula (Ib), or a pharmaceutically acceptable salt thereof, wherein $R^8$ is $C_{3-18}$alkyl. In another embodiment is a compound of Formula (Ib), or a pharmaceutically acceptable salt thereof, wherein $R^8$ is $C_{3-12}$alkyl. In another embodiment is a compound of Formula (Ib), or a pharmaceutically acceptable salt thereof, wherein $R^8$ is $C_{6-12}$alkyl. In another embodiment is a compound of Formula (Ib), or a pharmaceutically acceptable salt thereof, wherein $R^8$ is $C_{6-10}$alkyl. In another embodiment is a compound of Formula (Ib), or a pharmaceutically acceptable salt thereof, wherein $R^8$ is $C_{8-10}$alkyl. In another embodiment is a compound of Formula (Ib), or a pharmaceutically acceptable salt thereof, wherein $R^8$ is $-(CH_2)_2CH_3$. In another embodiment is a compound of Formula (Ib), or a pharmaceutically acceptable salt thereof, wherein $R^8$ is $-(CH_2)_3CH_3$. In another embodiment is a compound of Formula (Ib), or a pharmaceutically acceptable salt thereof, wherein $R^8$ is $-(CH_2)_4CH_3$. In another embodiment is a compound of Formula (Ib), or a pharmaceutically acceptable salt thereof, wherein $R^8$ is $-(CH_2)_5CH_3$. In another embodiment is a compound of Formula (Ib), or a pharmaceutically acceptable salt thereof, wherein $R^8$ is $-(CH_2)_6CH_3$. In another embodiment is a compound of Formula (Ib), or a pharmaceutically acceptable salt thereof, wherein $R^8$ is $-(CH_2)_7CH_3$. In another embodiment is a compound of Formula (Ib), or a pharmaceutically acceptable salt thereof, wherein $R^8$ is $-(CH_2)_8CH_3$. In another embodiment is a compound of Formula (Ib), or a pharmaceutically acceptable salt thereof, wherein $R^8$ is $-(CH_2)_9CH_3$. In another embodiment is a compound of Formula (Ib), or a pharmaceutically acceptable salt thereof, wherein $R^8$ is $-(CH_2)_{10}CH_3$. In another embodiment is a compound of Formula (Ib), or a pharmaceutically acceptable salt thereof, wherein $R^8$ is $-(CH_2)_{11}CH_3$. In another embodiment is a compound of Formula (Ib), or a pharmaceutically acceptable salt thereof, wherein $R^8$ is $-(CH_2)_{12}CH_3$. In another embodiment is a compound of Formula (Ib), or a pharmaceutically acceptable salt thereof, wherein $R^8$ is $-(CH_2)_{13}CH_3$. In another embodiment is a compound of Formula (Ib), or a pharmaceutically acceptable salt thereof, wherein $R^8$ is $-(CH_2)_{14}CH_3$. In another embodiment is a compound of Formula (Ib), or a pharmaceutically acceptable salt thereof, wherein $R^8$ is $-(CH_2)_{15}CH_3$. In another embodiment is a compound of Formula (Ib), or a pharmaceutically acceptable salt thereof, wherein $R^8$ is $-(CH_2)_{16}CH_3$. In another embodiment is a compound of Formula (Ib), or a pharmaceutically acceptable salt thereof, wherein $R^8$ is $-(CH_2)_{17}CH_3$. In another embodiment is a compound of Formula (Ib), or a pharmaceutically acceptable salt thereof, wherein $R^8$ is $C_{3-18}$alkenyl. In another embodiment is a compound of Formula (Ib), or a pharmaceutically acceptable salt thereof, wherein $R^8$ is $C_{3-12}$alkenyl. In another embodiment is a compound of Formula (Ib), or a pharmaceutically acceptable salt thereof, wherein $R^8$ is $C_{6-12}$alkenyl. In another embodiment is a compound of Formula (Ib), or a pharmaceutically acceptable salt thereof, wherein $R^8$ is $C_{6-10}$alkenyl. In another embodiment is a compound of Formula (Ib), or a pharmaceutically acceptable salt thereof, wherein $R^8$ is $C_{8-10}$alkenyl. In another embodiment is a compound of Formula (Ib), or a pharmaceutically acceptable salt thereof, wherein $R^8$ is $C_{3-18}$alkynyl. In another embodiment is a compound of Formula (Ib), or a pharmaceutically acceptable salt thereof, wherein $R^8$ is $C_{3-12}$alkynyl. In another embodiment is a compound of Formula (Ib), or a pharmaceutically acceptable salt thereof, wherein $R^8$ is $C_{6-12}$alkynyl. In another embodiment is a compound of Formula (Ib), or a pharmaceutically acceptable salt thereof, wherein $R^8$ is $C_{6-10}$alkynyl. In another embodiment is a compound of Formula (Ib), or a pharmaceutically acceptable salt thereof, wherein $R^8$ is $C_{8-10}$alkynyl. In another embodiment is a compound of Formula (Ib), or a pharmaceutically acceptable salt thereof, wherein $R^8$ is $C_{3-18}$haloalkyl. In another embodiment is a compound of Formula (Ib), or a pharmaceutically acceptable salt thereof, wherein $R^8$ is $C_{3-12}$haloalkyl. In another embodiment is a compound of Formula (Ib), or a pharmaceutically acceptable salt thereof, wherein $R^8$ is $C_{6-12}$haloalkyl. In another embodiment is a compound of Formula (Ib), or a pharmaceutically acceptable salt thereof, wherein $R^8$ is $C_{6-10}$haloalkyl. In another embodiment is a compound of Formula (Ib), or a pharmaceutically acceptable salt thereof, wherein $R^8$ is $C_{8-10}$haloalkyl. In another embodiment is a compound of Formula (Ib), or a pharmaceutically acceptable salt thereof, wherein $R^8$ is $C_{3-8}$cycloalkyl. In another embodiment is a compound of Formula (Ib), or a pharmaceutically acceptable salt thereof, wherein $R^8$ is $C_{3-6}$cycloalkyl. In another embodiment is a compound of Formula (Ib), or a pharmaceutically acceptable salt thereof, wherein $R^8$ is $C_{6-10}$aryl optionally substituted with 1, 2, 3, or 4 $R^{14}$. In another embodiment is a compound of Formula (Ib), or a pharmaceutically acceptable salt thereof, wherein $R^8$ is unsubstituted $C_{6-10}$aryl. In another embodiment is a compound of Formula (Ib), or a pharmaceutically acceptable salt thereof, wherein $R^8$ is $C_{6-10}$aryl substituted with 1 or 2 $R^{14}$. In another embodiment is a compound of Formula (Ib), or a pharmaceutically acceptable salt thereof, wherein $R^8$ is phenyl optionally substituted with 1, 2, 3, or 4 $R^{14}$. In another embodiment is a compound of Formula (Ib), or a pharmaceutically acceptable salt thereof, wherein $R^8$ is unsubstituted phenyl. In another embodiment is a compound of Formula (Ib), or a pharmaceutically acceptable salt thereof, wherein $R^8$ is phenyl substituted with 1 or 2 $R^{14}$. In another embodiment is a compound of Formula (Ib), or a pharmaceutically acceptable salt thereof, wherein $R^8$ is —$C_{1-8}$alkyl-$C_{6-10}$aryl optionally substituted with 1, 2, 3, or 4 $R^{14}$. In another embodiment is a compound of Formula (Ib), or a pharmaceutically acceptable salt thereof, wherein $R^8$ is unsubstituted —$C_{1-8}$alkyl-$C_{6-10}$aryl. In another embodiment is a compound of Formula (Ib), or a pharmaceutically acceptable salt thereof, wherein $R^8$ is —$C_{1-8}$alkyl-$C_{6-10}$aryl substituted with 1 or 2 $R^{14}$. In another embodiment is a compound of Formula (Ib), or a pharmaceutically acceptable salt thereof, wherein $R^8$ is —$CH_2$-phenyl optionally substituted with 1, 2, 3, or 4 $R^{14}$. In another embodiment is a compound of Formula (Ib), or a pharmaceutically acceptable salt thereof, wherein $R^8$ is unsubstituted —$CH_2$-phenyl. In another embodiment is a compound of Formula (Ib), or a pharmaceutically acceptable salt thereof, wherein $R^8$ is —$CH_2$-phenyl substituted with 1 or 2 $R^{14}$. In another embodiment is a compound of Formula (Ib), or a pharmaceutically acceptable salt thereof, wherein $R^8$ is $C_{2-9}$heteroaryl optionally substituted with 1, 2, 3, or 4 $R^{14}$. In another embodiment is a compound of Formula (Ib), or a pharmaceutically acceptable salt thereof, wherein $R^8$ is unsubstituted $C_{2-9}$heteroaryl. In another embodiment is a compound of Formula (Ib), or a pharmaceutically acceptable salt thereof, wherein $R^8$ is $C_{2-9}$heteroaryl substituted with 1 or 2 $R^{14}$. In another embodiment is a compound of Formula (Ib), or a pharmaceutically acceptable salt thereof, wherein $R^8$ is —$CH_2$—$C_{2-9}$heteroaryl optionally substituted with 1, 2, 3, or 4 $R^{14}$. In another embodiment is a compound of Formula (Ib), or a pharmaceutically acceptable salt thereof, wherein $R^8$ is unsubstituted —$CH_2$—$C_{2-9}$heteroaryl. In another embodiment is a compound of Formula (Ib), or a pharmaceutically acceptable salt thereof, wherein $R^8$ is —$CH_2$—$C_{2-9}$heteroaryl substituted with 1 or 2 $R^{14}$.

In another embodiment is a compound of Formula (Ib), or a pharmaceutically acceptable salt thereof, wherein $R^3$ is H. In another embodiment is a compound of Formula (Ib), or a pharmaceutically acceptable salt thereof, wherein $R^3$ is —C(O)$R^9$. In another embodiment is a compound of Formula (Ib), or a pharmaceutically acceptable salt thereof, wherein $R^3$ is —C(O)$R^9$ and $R^9$ is $C_{1-10}$alkyl. In another embodiment is a compound of Formula (Ib), or a pharmaceutically acceptable salt thereof, wherein $R^3$ is —C(O)$R^9$ and $R^9$ is $C_{1-6}$alkyl. In another embodiment is a compound of Formula (Ib), or a pharmaceutically acceptable salt thereof, wherein $R^3$ is —C(O)$R^9$ and $R^9$ is $C_{1-4}$alkyl. In another embodiment is a compound of Formula (Ib), or a pharmaceutically acceptable salt thereof, wherein $R^3$ is —C(O)$R^9$ and $R^9$ is —$CH_3$. In another embodiment is a compound of Formula (Ib), or a pharmaceutically acceptable salt thereof, wherein $R^3$ is —C(O)$R^9$ and $R^9$ is —$CH_2CH_3$. In another embodiment is a compound of Formula (Ib), or a pharmaceutically acceptable salt thereof, wherein $R^3$ is —C(O)O$R^9$. In another embodiment is a compound of Formula (Ib), or a pharmaceutically acceptable salt thereof, wherein $R^3$ is —C(O)O$R^9$ and $R^9$ is $C_{1-10}$alkyl. In another embodiment is a compound of Formula (Ib), or a pharmaceutically acceptable salt thereof, wherein $R^3$ is —C(O)O$R^9$ and $R^9$ is $C_{1-6}$alkyl. In another embodiment is a compound of Formula (Ib), or a pharmaceutically acceptable salt thereof, wherein $R^3$ is —C(O)O$R^9$ and $R^9$ is $C_{1-4}$alkyl. In another embodiment is a compound of Formula (Ib), or a pharmaceutically acceptable salt thereof, wherein $R^3$ is —C(O)O$R^9$ and $R^9$ is —$CH_3$. In another embodiment is a compound of Formula (Ib), or a pharmaceutically acceptable salt thereof, wherein $R^3$ is —C(O)O$R^9$ and $R^9$ is —$CH_2CH_3$.

In some embodiments is a compound of Formula (I') having the structure of Formula (Ic):

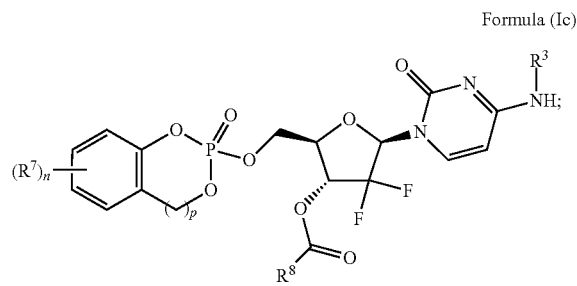

Formula (Ic)

wherein:
$R^3$ is H, —C(O)$R^9$, or —C(O)O$R^9$;
each $R^7$ is independently selected from halogen, $C_{1-8}$alkyl, $C_{1-8}$haloalkyl, and $C_{1-8}$alkoxy;
$R^8$ is $C_{3-18}$alkyl, $C_{3-18}$alkenyl, $C_{3-18}$alkynyl, $C_{3-18}$haloalkyl, $C_{3-8}$cycloalkyl, $C_{6-10}$aryl, —$C_{1-8}$alkyl-$C_{6-10}$aryl, $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl, $C_{2-9}$heteroaryl, or —$C_{1-8}$alkyl-$C_{2-9}$heteroaryl are optionally substituted with 1, 2, 3, or 4 $R^{14}$;
$R^9$ is $C_{1-12}$alkyl;
each $R^{13}$ is independently selected from $C_{1-12}$alkyl;
each $R^{14}$ is independently selected from halogen, $C_{1-8}$alkyl, $C_{1-8}$haloalkyl, $C_{1-8}$alkoxy, and —C(O)$R^{13}$;
n is 0, 1, 2, 3, or 4; and
p is 0 or 1;
or a pharmaceutically acceptable salt thereof.

In another embodiment is a compound of Formula (Ic), or a pharmaceutically acceptable salt thereof, wherein p is 1. In another embodiment is a compound of Formula (Ic), or a pharmaceutically acceptable salt thereof, wherein p is 1 and n is 0. In another embodiment is a compound of Formula (Ic), or a pharmaceutically acceptable salt thereof, wherein p is 1 and n is 1, 2, 3, or 4. In another embodiment is a compound of Formula (Ic), or a pharmaceutically acceptable salt thereof, wherein p is 1, n is 1, 2, 3, or 4, and each $R^7$ is independently selected from $C_{1-8}$alkyl, $C_{1-8}$haloalkyl, and $C_{1-8}$alkoxy. In another embodiment is a compound of Formula (Ic), or a pharmaceutically acceptable salt thereof, wherein p is 1 and n is 1 or 2. In another embodiment is a compound of Formula (Ic), or a pharmaceutically acceptable salt thereof, wherein p is 1, n is 1 or 2, and each $R^7$ is independently selected from $C_{1-8}$alkyl, $C_{1-8}$haloalkyl, and $C_{1-8}$alkoxy. In another embodiment is a compound of Formula (Ic), or a pharmaceutically acceptable salt thereof, wherein p is 1, n is 2. In another embodiment is a compound of Formula (Ic), or a pharmaceutically acceptable salt thereof, wherein p is 1, n is 2, and each $R^7$ is independently selected from $C_{1-8}$alkyl, $C_{1-8}$haloalkyl, and $C_{1-8}$alkoxy. In another embodiment is a compound of Formula (Ic), or a pharmaceutically acceptable salt thereof, wherein p is 1 and n is 1. In another embodiment is a compound of Formula (Ic), or a pharmaceutically acceptable salt thereof, wherein p is 1, n is 1, and $R^7$ is selected from $C_{1-8}$alkyl, $C_{1-8}$haloalkyl, and $C_{1-8}$alkoxy. In another embodiment is a compound of Formula (Ic), or a pharmaceutically acceptable salt thereof, wherein p is 1, n is 1, and $R^7$ is halogen. In another embodiment is a compound of Formula (Ic), or a pharmaceutically acceptable salt thereof, wherein p is 1, n is 1, and $R^7$ is $C_{1-8}$alkyl. In another embodiment is a compound of Formula (Ic), or a pharmaceutically acceptable salt thereof, wherein p is 1, n is 1, and $R^7$ is $C_{1-8}$haloalkyl. In another embodiment is a compound of Formula (Ic), or a pharmaceutically acceptable salt thereof, wherein p is 1, n is 1, and $R^7$ is $C_{1-8}$alkoxy. In another embodiment is a compound of Formula (Ic), or a pharmaceutically acceptable salt thereof, wherein p is 0. In another embodiment is a compound of Formula (Ic), or a pharmaceutically acceptable salt thereof, wherein p is 0 and n is 0. In another embodiment is a compound of Formula (Ic), or a pharmaceutically acceptable salt thereof, wherein p is 0 and n is 1, 2, 3, or 4. In another embodiment is a compound of Formula (Ic), or a pharmaceutically acceptable salt thereof, wherein p is 0, n is 1, 2, 3, or 4, and each $R^7$ is independently selected from $C_{1-8}$alkyl, $C_{1-8}$haloalkyl, and $C_{1-8}$alkoxy. In another embodiment is a compound of Formula (Ic), or a pharmaceutically acceptable salt thereof, wherein p is 0 and n is 1 or 2. In another embodiment is a compound of Formula (Ic), or a pharmaceutically acceptable salt thereof, wherein p is 0, n is 1 or 2, and each $R^7$ is independently selected from $C_{1-8}$alkyl, $C_{1-8}$haloalkyl, and $C_{1-8}$alkoxy. In another embodiment is a compound of Formula (Ic), or a pharmaceutically acceptable salt thereof, wherein p is 0, n is 2. In another embodiment is a compound of Formula (Ic), or a pharmaceutically acceptable salt thereof, wherein p is 0, n is 2, and each $R^7$ is independently selected from $C_{1-8}$alkyl, $C_{1-8}$haloalkyl, and $C_{1-8}$alkoxy. In another embodiment is a compound of Formula (Ic), or a pharmaceutically acceptable salt thereof, wherein p is 0 and n is 1. In another embodiment is a compound of Formula (Ic), or a pharmaceutically acceptable salt thereof, wherein p is 0, n is 1, and $R^7$ is selected from $C_{1-8}$alkyl, $C_{1-8}$haloalkyl, and $C_{1-8}$alkoxy. In another embodiment is a compound of Formula (Ic), or a pharmaceutically acceptable salt thereof, wherein p is 0, n is 1, and $R^7$ is halogen. In another embodiment is a compound of Formula (Ic), or a pharmaceutically acceptable salt thereof, wherein p is 0, n is 1, and $R^7$ is $C_{1-8}$alkyl. In another embodiment is a compound of Formula (Ic), or a pharmaceutically acceptable salt thereof, wherein p is 0, n is 1, and $R^7$ is $C_{1-8}$haloalkyl. In another embodiment is a compound of Formula (Ic), or a pharmaceutically acceptable salt thereof, wherein p is 0, n is 1, and $R^7$ is $C_{1-8}$alkoxy.

In another embodiment is a compound of Formula (Ic), or a pharmaceutically acceptable salt thereof, wherein $R^8$ is $C_{3-18}$alkyl. In another embodiment is a compound of Formula (Ic), or a pharmaceutically acceptable salt thereof, wherein $R^8$ is $C_{3-12}$alkyl. In another embodiment is a compound of Formula (Ic), or a pharmaceutically acceptable salt thereof, wherein $R^8$ is $C_{6-12}$alkyl. In another embodiment is a compound of Formula (Ic), or a pharmaceutically acceptable salt thereof, wherein $R^8$ is $C_{6-10}$alkyl. In another embodiment is a compound of Formula (Ic), or a pharmaceutically acceptable salt thereof, wherein $R^8$ is $C_{8-10}$alkyl. In another embodiment is a compound of Formula (Ic), or a pharmaceutically acceptable salt thereof, wherein $R^8$ is —$(CH_2)_2CH_3$. In another embodiment is a compound of Formula (Ic), or a pharmaceutically acceptable salt thereof, wherein $R^8$ is —$(CH_2)_3CH_3$. In another embodiment is a compound of Formula (Ic), or a pharmaceutically acceptable salt thereof, wherein $R^8$ is —$(CH_2)_4CH_3$. In another embodiment is a compound of Formula (Ic), or a pharmaceutically acceptable salt thereof, wherein $R^8$ is —$(CH_2)_5CH_3$. In another embodiment is a compound of Formula (Ic), or a pharmaceutically acceptable salt thereof, wherein $R^8$ is —$(CH_2)_6CH_3$. In another embodiment is a compound of Formula (Ic), or a pharmaceutically acceptable salt thereof, wherein $R^8$ is —$(CH_2)_7CH_3$. In another embodiment is a compound of Formula (Ic), or a pharmaceutically acceptable salt thereof, wherein $R^8$ is —$(CH_2)_8CH_3$. In another embodiment is a compound of Formula (Ic), or a pharmaceutically acceptable salt thereof, wherein $R^8$ is —$(CH_2)_9CH_3$. In another embodiment is a compound of Formula (Ic), or a pharmaceutically acceptable salt thereof, wherein $R^8$ is —$(CH_2)_{10}CH_3$. In another embodiment is a compound of Formula (Ic), or a pharmaceutically acceptable salt thereof, wherein $R^8$ is —$(CH_2)_{11}CH_3$. In another embodiment is a compound of Formula (Ic), or a pharmaceutically acceptable salt thereof, wherein $R^8$ is —$(CH_2)_{12}CH_3$. In another embodiment is a compound of Formula (Ic), or a pharmaceutically acceptable salt thereof, wherein $R^8$ is —$(CH_2)_{13}CH_3$. In another embodiment is a compound of Formula (Ic), or a pharmaceutically acceptable salt thereof, wherein $R^8$ is —$(CH_2)_{14}CH_3$. In another embodiment is a compound of Formula (Ic), or a pharmaceutically acceptable salt thereof, wherein $R^8$ is —$(CH_2)_{15}CH_3$. In another embodiment is a compound of Formula (Ic), or a pharmaceutically acceptable salt thereof, wherein $R^8$ is —$(CH_2)_{16}CH_3$. In another embodiment is a compound of Formula (Ic), or a pharmaceutically acceptable salt thereof, wherein $R^8$ is —$(CH_2)_{17}CH_3$. In another embodiment is a compound of Formula (Ic), or a pharmaceutically acceptable salt thereof, wherein $R^8$ is $C_{3-18}$alkenyl. In another embodiment is a compound of Formula (Ic), or a pharmaceutically acceptable salt thereof, wherein $R^8$ is $C_{3-12}$alkenyl. In another embodiment is a compound of Formula (Ic), or a pharmaceutically acceptable salt thereof, wherein $R^8$ is $C_{6-12}$alkenyl. In another embodiment is a compound of Formula (Ic), or a pharmaceutically acceptable salt thereof, wherein $R^8$ is $C_{6-10}$alkenyl. In another embodiment is a compound of Formula (Ic), or a pharmaceutically acceptable salt thereof, wherein $R^8$ is $C_{8-10}$alkenyl. In another embodiment is a compound of Formula (Ic), or a pharmaceutically acceptable salt thereof, wherein $R^8$ is $C_{3-18}$alkynyl. In another embodiment is a compound of Formula (Ic), or a pharmaceutically acceptable salt thereof, wherein $R^8$ is $C_{3-12}$alkynyl. In another embodiment is a compound of Formula (Ic), or a pharmaceutically acceptable salt thereof, wherein $R^8$ is $C_{6-12}$alkynyl. In another embodiment is a compound of Formula (Ic), or a pharmaceutically acceptable salt thereof, wherein $R^8$ is $C_{6-10}$alkynyl. In another embodiment is a compound of Formula (Ic), or a pharmaceutically acceptable salt thereof, wherein $R^8$ is $C_{8-10}$alkynyl. In another embodiment is a compound of Formula (Ic), or a pharmaceutically acceptable salt thereof, wherein $R^8$ is $C_{3-18}$haloalkyl. In another embodiment is a compound of Formula (Ic), or a pharmaceutically acceptable salt thereof, wherein $R^8$ is $C_{3-12}$haloalkyl. In another embodiment is a compound of Formula (Ic), or a pharmaceutically acceptable salt thereof, wherein $R^8$ is $C_{6-12}$haloalkyl. In another embodiment is a compound of Formula (Ic), or a pharmaceutically acceptable salt thereof, wherein $R^8$ is $C_{6-10}$haloalkyl. In another embodiment is a compound of Formula (Ic), or a pharmaceutically acceptable salt thereof, wherein $R^8$ is $C_{8-10}$haloalkyl. In another embodiment is a compound of Formula (Ic), or a pharmaceutically acceptable salt thereof, wherein $R^8$ is $C_{3-8}$cycloalkyl. In another embodiment is a compound of Formula (Ic), or a pharmaceutically acceptable salt thereof, wherein $R^8$ is $C_{3-6}$cycloalkyl. In another embodiment is a compound of Formula (Ic), or a pharmaceutically acceptable salt thereof, wherein $R^8$ is $C_{6-10}$aryl optionally substituted with 1, 2, 3, or 4 $R^{14}$. In another embodiment is a compound of Formula (Ic), or a pharmaceutically acceptable salt thereof, wherein $R^8$ is unsubstituted $C_{6-10}$aryl. In another embodiment is a compound of Formula (Ic), or a pharmaceutically acceptable salt thereof, wherein $R^8$ is $C_{6-10}$aryl substituted with 1 or 2 $R^{14}$. In another embodiment is a compound of Formula (Ic), or a pharmaceutically acceptable salt thereof, wherein $R^8$ is phenyl optionally substituted with 1, 2, 3, or 4 $R^{14}$. In another embodiment is a compound of Formula (Ic), or a pharmaceutically acceptable salt thereof, wherein $R^8$ is unsubstituted phenyl. In another embodiment is a compound of Formula (Ic), or a pharmaceutically acceptable salt thereof, wherein $R^8$ is phenyl substituted with 1 or 2 $R^{14}$. In another embodiment is a compound of Formula (Ic), or a pharmaceutically acceptable salt thereof, wherein $R^8$ is —$C_{1-8}$alkyl-$C_{6-10}$aryl optionally substituted with 1, 2, 3, or 4 $R^{14}$. In another embodiment is a compound of Formula (Ic), or a pharmaceutically acceptable salt thereof, wherein $R^8$ is unsubstituted —$C_{1-8}$alkyl-$C_{6-10}$aryl. In another embodiment is a compound of Formula (Ic), or a pharmaceutically acceptable salt thereof, wherein $R^8$ is —$C_{1-8}$alkyl-$C_{6-10}$aryl substituted with 1 or 2 $R^{14}$. In another embodiment is a compound of Formula (Ic), or a pharmaceutically acceptable salt thereof, wherein $R^8$ is —$CH_2$-phenyl optionally substituted with 1, 2, 3, or 4 $R^{14}$. In another embodiment is a compound of Formula (Ic), or a pharmaceutically acceptable salt thereof, wherein $R^8$ is unsubstituted —$CH_2$— phenyl. In another embodiment is a compound of Formula (Ic), or a pharmaceutically acceptable salt thereof, wherein $R^8$ is —$CH_2$-phenyl substituted with 1 or 2 $R^{14}$. In another embodiment is a compound of Formula (Ic), or a pharmaceutically acceptable salt thereof, wherein $R^8$ is $C_{2-9}$heteroaryl optionally substituted with 1, 2, 3, or 4 $R^{14}$. In another embodiment is a compound of Formula (Ic), or a pharmaceutically acceptable salt thereof, wherein $R^8$ is unsubstituted $C_{2-9}$heteroaryl. In another embodiment is a compound of Formula (Ic), or a pharmaceutically acceptable salt thereof, wherein $R^8$ is $C_{2-9}$heteroaryl substituted with 1 or 2 $R^{14}$. In another embodiment is a compound of Formula (Ic), or a pharmaceutically acceptable salt thereof, wherein $R^8$ is —$CH_2$—$C_{2-9}$heteroaryl optionally substituted with 1, 2, 3, or 4 $R^{14}$. In another embodiment is a compound of Formula (Ic), or a pharmaceutically acceptable salt thereof, wherein $R^8$ is unsubstituted —$CH_2$—$C_{2-9}$heteroaryl. In another embodiment is a compound of Formula (Ic), or a pharmaceutically acceptable salt thereof, wherein $R^8$ is —$CH_2$—$C_{2-9}$heteroaryl substituted with 1 or 2 $R^{14}$.

In another embodiment is a compound of Formula (Ic), or a pharmaceutically acceptable salt thereof, wherein $R^3$ is H. In another embodiment is a compound of Formula (Ic), or a pharmaceutically acceptable salt thereof, wherein $R^3$ is —$C(O)R^9$. In another embodiment is a compound of Formula (Ic), or a pharmaceutically acceptable salt thereof, wherein $R^3$ is —$C(O)R^9$ and $R^9$ is $C_{1-10}$alkyl. In another embodiment is a compound of Formula (Ic), or a pharmaceutically acceptable salt thereof, wherein $R^3$ is —$C(O)R^9$ and $R^9$ is $C_{1-6}$alkyl. In another embodiment is a compound of Formula (Ic), or a pharmaceutically acceptable salt thereof, wherein $R^3$ is —$C(O)R^9$ and $R^9$ is $C_{1-4}$alkyl. In another embodiment is a compound of Formula (Ic), or a pharmaceutically acceptable salt thereof, wherein $R^3$ is —$C(O)R^9$ and $R^9$ is —$CH_3$. In another embodiment is a compound of Formula (Ic), or a pharmaceutically acceptable salt thereof, wherein $R^3$ is —$C(O)R^9$ and $R^9$ is —$CH_2CH_3$. In another embodiment is a compound of Formula (Ic), or a pharmaceutically acceptable salt thereof, wherein $R^3$ is —$C(O)OR^9$. In another embodiment is a compound of Formula (Ic), or a pharmaceutically acceptable salt thereof, wherein $R^3$ is —$C(O)OR^9$ and $R^9$ is $C_{1-10}$alkyl. In another embodiment is a compound of Formula (Ic), or a pharmaceutically acceptable salt thereof, wherein $R^3$ is —$C(O)OR^9$ and $R^9$ is $C_{1-6}$alkyl. In another embodiment is a compound of Formula (Ic), or a pharmaceutically acceptable salt thereof, wherein $R^3$ is —$C(O)OR^9$ and $R^9$ is $C_{1-4}$alkyl. In another embodiment is a compound of Formula (Ic), or a pharmaceutically acceptable salt thereof, wherein $R^3$ is —$C(O)OR^9$ and $R^9$ is —$CH_3$. In another embodiment is a compound of Formula (Ic), or a pharmaceutically acceptable salt thereof, wherein $R^3$ is —$C(O)OR^9$ and $R^9$ is —$CH_2CH_3$.

In another embodiment is a compound of Formula (II):

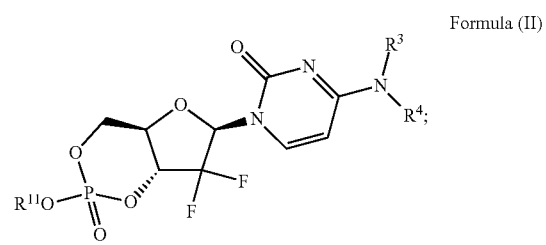

Formula (II)

wherein:
$R^3$ is H, —$C(O)R^9$, or —$C(O)OR^9$;
$R^4$ is H;
$R^9$ is $C_{1-8}$alkyl;
$R^{11}$ is $C_{3-18}$alkyl, $C_{3-18}$alkenyl, $C_{3-18}$alkynyl, $C_{3-18}$haloalkyl, —$C_{1-4}$alkyl-OC(O)$C_{1-8}$alkyl, $C_{6-10}$aryl, —$C_{1-8}$alkyl-$C_{6-10}$aryl, $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl, $C_{2-9}$heteroaryl, or —$C_{1-8}$alkyl-$C_{2-9}$heteroaryl are optionally substituted with 1, 2, 3, or 4 $R^{12}$;
each $R^{12}$ is independently selected from halogen, $C_{1-8}$alkyl, $C_{1-8}$haloalkyl, $C_{1-8}$alkoxy, and —$C(O)R^{13}$; and
each $R^{13}$ is independently selected from $C_{1-12}$alkyl;
or a pharmaceutically acceptable salt thereof.

In another embodiment is a compound of Formula (II), or a pharmaceutically acceptable salt thereof, wherein $R^{11}$ is $C_{3-18}$alkyl. In another embodiment is a compound of Formula (II), or a pharmaceutically acceptable salt thereof, wherein $R^{11}$ is $C_{3-12}$alkyl. In another embodiment is a compound of Formula (II), or a pharmaceutically acceptable salt thereof, wherein $R^{11}$ is $C_{6-12}$alkyl. In another embodiment is a compound of Formula (II), or a pharmaceutically acceptable salt thereof, wherein $R^{11}$ is $C_{6-10}$alkyl. In another embodiment is a compound of Formula (II), or a pharmaceutically acceptable salt thereof, wherein $R^{11}$ is $C_{8-10}$alkyl. In another embodiment is a compound of Formula (II), or a pharmaceutically acceptable salt thereof, wherein $R^{11}$ is —$(CH_2)_2CH_3$. In another embodiment is a compound of Formula (II), or a pharmaceutically acceptable salt thereof, wherein $R^{11}$ is —$(CH_2)_3CH_3$. In another embodiment is a compound of Formula (II), or a pharmaceutically acceptable salt thereof, wherein $R^{11}$ is —$(CH_2)_4CH_3$. In another embodiment is a compound of Formula (II), or a pharmaceutically acceptable salt thereof, wherein $R^{11}$ is —$(CH_2)_5CH_3$. In another embodiment is a compound of Formula (II), or a pharmaceutically acceptable salt thereof, wherein $R^{11}$ is —$(CH_2)_6CH_3$. In another embodiment is a compound of Formula (II), or a pharmaceutically acceptable salt thereof, wherein $R^{11}$ is —$(CH_2)_7CH_3$. In another embodiment is a compound of Formula (II), or a pharmaceutically acceptable salt thereof, wherein $R^{11}$ is —$(CH_2)_8CH_3$. In another embodiment is a compound of Formula (II), or a pharmaceutically acceptable salt thereof, wherein $R^{11}$ is —$(CH_2)_9CH_3$. In another embodiment is a compound of Formula (II), or a pharmaceutically acceptable salt thereof, wherein $R^{11}$ is —$(CH_2)_{10}CH_3$. In another embodiment is a compound of Formula (II), or a pharmaceutically acceptable salt thereof, wherein $R^{11}$ is —$(CH_2)_{11}CH_3$. In another embodiment is a compound of Formula (II), or a pharmaceutically acceptable salt thereof, wherein $R^{11}$ is —$(CH_2)_{12}CH_3$. In another embodiment is a compound of Formula (II), or a pharmaceutically acceptable salt thereof, wherein $R^{11}$ is —$(CH_2)_{13}CH_3$. In another embodiment is a compound of Formula (II), or a pharmaceutically acceptable salt thereof, wherein $R^{11}$ is —$(CH_2)_{14}CH_3$. In another embodiment is a compound of Formula (II), or a pharmaceutically acceptable salt thereof, wherein $R^{11}$ is —$(CH_2)_{15}CH_3$. In another embodiment is a compound of Formula (II), or a pharmaceutically acceptable salt thereof, wherein $R^{11}$ is —$(CH_2)_{16}CH_3$. In another embodiment is a compound of Formula (II), or a pharmaceutically acceptable salt thereof, wherein $R^{11}$ is —$(CH_2)_{17}CH_3$. In another embodiment is a compound of Formula (II), or a pharmaceutically acceptable salt thereof, wherein $R^{11}$ is $C_{3-18}$alkenyl. In another embodiment is a compound of Formula (II), or a pharmaceutically acceptable salt thereof, wherein $R^{11}$ is $C_{3-12}$alkenyl. In another embodiment is a compound of Formula (II), or a pharmaceutically acceptable salt thereof, wherein $R^{11}$ is $C_{6-12}$alkenyl. In another embodiment is a compound of Formula (II), or a pharmaceutically acceptable salt thereof, wherein $R^{11}$ is $C_{6-10}$alkenyl. In another embodiment is a compound of Formula (II), or a pharmaceutically acceptable salt thereof, wherein $R^{11}$ is $C_{8-10}$alkenyl. In another embodiment is a compound of Formula (II), or a pharmaceutically acceptable salt thereof, wherein $R^{11}$ is $C_{3-18}$alkynyl. In another embodiment is a compound of Formula (II), or a pharmaceutically acceptable salt thereof, wherein $R^{11}$ is $C_{3-12}$alkynyl. In another embodiment is a compound of Formula (II), or a pharmaceutically acceptable salt thereof, wherein $R^{11}$ is $C_{6-12}$alkynyl. In another embodiment is a compound of Formula (II), or a pharmaceutically acceptable salt thereof, wherein $R^{11}$ is $C_{6-10}$alkynyl. In another embodiment is a compound of Formula (II), or a pharmaceutically acceptable salt thereof, wherein $R^{11}$ is $C_{8-10}$alkynyl. In another embodiment is a compound of Formula (II), or a pharmaceutically acceptable salt thereof, wherein $R^{11}$ is $C_{3-18}$haloalkyl. In another embodiment is a compound of Formula (II), or a pharmaceutically acceptable salt thereof, wherein $R^{11}$ is $C_{3-12}$haloalkyl. In another embodiment is a compound of Formula (II), or a pharmaceutically acceptable salt thereof, wherein $R^{11}$ is $C_{6-12}$haloalkyl. In another embodiment is a compound of Formula (II), or a pharmaceutically acceptable salt thereof, wherein $R^{11}$ is $C_{6-10}$haloalkyl. In another embodiment is a compound of Formula (II), or a pharmaceutically acceptable salt thereof, wherein $R^{11}$ is $C_{8-10}$haloalkyl. In another embodiment is a compound of Formula (II), or a pharmaceutically acceptable salt thereof, wherein $R^{11}$ is —$C_{1-4}$alkyl-OC(O)$C_{1-8}$alkyl. In another embodiment is a compound of Formula (II), or a pharmaceutically acceptable salt thereof, wherein $R^{11}$ is —$C_{1-2}$alkyl-OC(O)$C_{1-8}$alkyl. In another embodiment is a compound of Formula (II), or a pharmaceutically acceptable salt thereof, wherein $R^{11}$ is —$CH_2OC(O)C_{1-8}$alkyl. In another embodiment is a compound of Formula (II), or a pharmaceutically acceptable salt thereof, wherein $R^{11}$ is —$C_{1-4}$alkyl-OC(O)$C_{1-6}$alkyl. In another embodiment is a compound of Formula (II), or a pharmaceutically acceptable salt thereof, wherein $R^{11}$ is —$C_{1-2}$alkyl-OC(O)$C_{1-6}$alkyl. In another embodiment is a compound of Formula (II), or a pharmaceutically acceptable salt thereof, wherein $R^{11}$ is —$CH_2OC(O)C_{1-6}$alkyl. In another embodiment is a compound of Formula (II), or a pharmaceutically acceptable salt thereof, wherein $R^{11}$ is —$C_{1-4}$alkyl-OC(O)$C_{1-4}$alkyl. In another embodiment is a compound of Formula (II), or a pharmaceutically acceptable salt thereof, wherein $R^{11}$ is —$C_{1-2}$alkyl-OC(O)$C_{1-4}$alkyl. In another embodiment is a compound of Formula (II), or a pharmaceutically acceptable salt thereof, wherein $R^{11}$ is —$CH_2OC(O)C_{1-4}$alkyl. In another embodiment is a compound of Formula (II), or a pharmaceutically acceptable salt thereof, wherein $R^{11}$ is —$C_{1-4}$alkyl-OC(O)C($CH_3$)$_3$. In another embodiment is a compound of Formula (II), or a pharmaceutically acceptable salt thereof, wherein $R^{11}$ is —$C_{1-2}$alkyl-OC(O)C($CH_3$)$_3$. In another embodiment is a compound of Formula (II), or a pharmaceutically acceptable salt thereof, wherein $R^{11}$ is —$CH_2OC(O)C(CH_3)_3$. In another embodiment is a compound of Formula (II), or a pharmaceutically acceptable salt thereof, wherein $R^{11}$ is $C_{6-10}$aryl optionally substituted with 1, 2, 3, or 4 $R^{12}$. In another embodiment is a compound of Formula (II), or a pharmaceutically acceptable salt thereof, wherein $R^{11}$ is unsubstituted $C_{6-10}$aryl. In another embodiment is a compound of Formula (II), or a pharmaceutically acceptable salt thereof, wherein $R^{11}$ is $C_{6-10}$aryl substituted with 1, 2, 3, or 4 $R^{12}$. In another embodiment is a compound of Formula (II), or a pharmaceutically acceptable salt thereof, wherein $R^{11}$ is $C_{6-10}$aryl substituted with 1, 2, or 3 $R^{12}$. In another embodiment is a compound of Formula (II), or a pharmaceutically acceptable salt thereof, wherein $R^{11}$ is $C_{6-10}$aryl substituted with 1 or 2 In another embodiment is a compound of Formula (II), or a pharmaceutically acceptable salt thereof, wherein $R^{11}$ is $C_{6-10}$aryl substituted with 1 or 2 $R^{12}$ and each $R^{12}$ is independently selected from halogen, $C_{1-8}$alkyl, $C_{1-8}$haloalkyl, and $C_{1-8}$alkoxy. In another embodiment is a compound of Formula (II), or a pharmaceutically acceptable salt thereof, wherein $R^{11}$ is $C_{6-10}$aryl substituted with 1 or 2 $R^{12}$ and each $R^{12}$ is independently selected from $C_{1-8}$alkyl, $C_{1-8}$alkoxy, and —C(O)$R^{13}$. In another embodiment is a compound of Formula (II), or a pharmaceutically acceptable salt thereof, wherein $R^{11}$ is $C_{6-10}$aryl substituted with 1 or 2 $R^{12}$ and each $R^{12}$ is independently selected from $C_{1-8}$alkyl, $C_{1-8}$haloalkyl, and $C_{1-8}$alkoxy. In another embodiment is a compound of Formula (II), or a pharmaceutically acceptable salt thereof, wherein $R^{11}$ is $C_{6-10}$aryl substituted with 1 or 2 $R^{12}$ and each $R^{12}$ is independently selected from $C_{1-8}$alkyl and $C_{1-8}$alkoxy. In another embodiment is a compound of Formula (II), or a pharmaceutically acceptable salt thereof, wherein $R^{11}$ is $C_{6-10}$aryl substituted with 1 In another embodiment is a compound of Formula (II), or a pharmaceutically acceptable salt thereof, wherein $R^{11}$ is $C_{6-10}$aryl substituted with 1 $R^{12}$ and $R^{12}$ is selected from halogen, $C_{1-8}$alkyl, $C_{1-8}$haloalkyl, and $C_{1-8}$alkoxy. In another embodiment is a compound of Formula (II), or a pharmaceutically acceptable salt thereof, wherein $R^{11}$ is $C_{6-10}$aryl substituted with 1 $R^{12}$ and $R^{12}$ is selected from $C_{1-8}$alkyl, $C_{1-8}$alkoxy, and —C(O)$R^{13}$. In another embodiment is a compound of Formula (II), or a pharmaceutically acceptable salt thereof, wherein $R^{11}$ is $C_{6-10}$aryl substituted with 1 $R^{12}$ and $R^{12}$ is selected from $C_{1-8}$alkyl and $C_{1-8}$alkoxy. In another embodiment is a compound of Formula (II), or a pharmaceutically acceptable salt thereof, wherein $R^{11}$ is $C_{6-10}$aryl substituted with 1 $R^{12}$ and $R^{12}$ is halogen. In another embodiment is a compound of Formula (II), or a pharmaceutically acceptable salt thereof, wherein $R^{11}$ is $C_{6-10}$aryl substituted with 1 $R^{12}$ and $R^{12}$ is —F. In another embodiment is a compound of Formula (II), or a pharmaceutically acceptable salt thereof, wherein $R^{11}$ is $C_{6-10}$aryl substituted with 1 $R^{12}$ and $R^{12}$ is —Cl. In another embodiment is a compound of Formula (II), or a pharmaceutically acceptable salt thereof, wherein $R^{11}$ is $C_{6-10}$aryl substituted with 1 $R^{12}$ and $R^{12}$ is $C_{1-8}$alkyl. In another embodiment is a compound of Formula (II), or a pharmaceutically acceptable salt thereof, wherein $R^{11}$ is $C_{6-10}$aryl substituted with 1 $R^{12}$ and $R^{12}$ is —CH$_3$. In another embodiment is a compound of Formula (II), or a pharmaceutically acceptable salt thereof, wherein $R^{11}$ is $C_{6-10}$aryl substituted with 1 $R^{12}$ and $R^{12}$ is $C_{1-8}$haloalkyl. In another embodiment is a compound of Formula (II), or a pharmaceutically acceptable salt thereof, wherein $R^{11}$ is $C_{6-10}$aryl substituted with 1 $R^{12}$ and $R^{12}$ is —CF$_3$. In another embodiment is a compound of Formula (II), or a pharmaceutically acceptable salt thereof, wherein $R^{11}$ is $C_{6-10}$aryl substituted with 1 $R^{12}$ and $R^{12}$ is $C_{1-8}$alkoxy. In another embodiment is a compound of Formula (II), or a pharmaceutically acceptable salt thereof, wherein $R^{11}$ is $C_{6-10}$aryl substituted with 1 $R^{12}$ and $R^{12}$ is —OCH$_3$. In another embodiment is a compound of Formula (II), or a pharmaceutically acceptable salt thereof, wherein $R^{11}$ is $C_{6-10}$aryl substituted with 1 $R^{12}$ and $R^{12}$ is —C(O)$R^{13}$. In another embodiment is a compound of Formula (II), or a pharmaceutically acceptable salt thereof, wherein $R^{11}$ is phenyl optionally substituted with 1, 2, 3, or 4 $R^{12}$. In another embodiment is a compound of Formula (II), or a pharmaceutically acceptable salt thereof, wherein $R^{11}$ is unsubstituted phenyl. In another embodiment is a compound of Formula (II), or a pharmaceutically acceptable salt thereof, wherein $R^{11}$ is phenyl substituted with 1, 2, 3, or 4 $R^{12}$. In another embodiment is a compound of Formula (II), or a pharmaceutically acceptable salt thereof, wherein $R^{11}$ is phenyl substituted with 1, 2, or 3 $R^{12}$. In another embodiment is a compound of Formula (II), or a pharmaceutically acceptable salt thereof, wherein $R^{11}$ is phenyl substituted with 1 or 2 $R^{12}$. In another embodiment is a compound of Formula (II), or a pharmaceutically acceptable salt thereof, wherein $R^{11}$ is phenyl substituted with 1 or 2 $R^{12}$ and each $R^{12}$ is independently selected from halogen, $C_{1-8}$alkyl, $C_{1-8}$haloalkyl, and $C_{1-8}$alkoxy. In another embodiment is a compound of Formula (II), or a pharmaceutically acceptable salt thereof, wherein $R^{11}$ is phenyl substituted with 1 or 2 $R^{12}$ and each $R^{12}$ is independently selected from $C_{1-8}$alkyl, $C_{1-8}$alkoxy, and —C(O)$R^{13}$. In another embodiment is a compound of Formula (II), or a pharmaceutically acceptable salt thereof, wherein $R^{11}$ is phenyl substituted with 1 or 2 $R^{12}$ and each $R^{12}$ is independently selected from $C_{1-8}$alkyl, $C_{1-8}$haloalkyl, and $C_{1-8}$alkoxy. In another embodiment is a compound of Formula (II), or a pharmaceutically acceptable salt thereof, wherein $R^{11}$ is phenyl substituted with 1 or 2 $R^{12}$ and each $R^{12}$ is independently selected from $C_{1-8}$alkyl and $C_{1-8}$alkoxy. In another embodiment is a compound of Formula (II), or a pharmaceutically acceptable salt thereof, wherein $R^{11}$ is phenyl substituted with 1 $R^{12}$. In another embodiment is a compound of Formula (II), or a pharmaceutically acceptable salt thereof, wherein $R^{11}$ is phenyl substituted with 1 $R^{12}$ and $R^{12}$ is selected from halogen, $C_{1-8}$alkyl, $C_{1-8}$haloalkyl, and $C_{1-8}$alkoxy. In another embodiment is a compound of Formula (II), or a pharmaceutically acceptable salt thereof, wherein $R^{11}$ is phenyl substituted with 1 $R^{12}$ and $R^{12}$ is selected from $C_{1-8}$alkyl, $C_{1-8}$alkoxy, and —C(O)$R^{13}$. In another embodiment is a compound of Formula (II), or a pharmaceutically acceptable salt thereof, wherein $R^{11}$ is phenyl substituted with 1 $R^{12}$ and $R^{12}$ is selected from $C_{1-8}$alkyl and $C_{1-8}$alkoxy. In another embodiment is a compound of Formula (II), or a pharmaceutically acceptable salt thereof, wherein $R^{11}$ is phenyl substituted with 1 $R^{12}$ and $R^{12}$ is halogen. In another embodiment is a compound of Formula (II), or a pharmaceutically acceptable salt thereof, wherein $R^{11}$ is phenyl substituted with 1 $R^{12}$ and $R^{12}$ is —F. In another embodiment is a compound of Formula (II), or a pharmaceutically acceptable salt thereof, wherein $R^{11}$ is phenyl substituted with 1 $R^{12}$ and $R^{12}$ is —Cl. In another embodiment is a compound of Formula (II), or a pharmaceutically acceptable salt thereof, wherein $R^{11}$ is phenyl substituted with 1 $R^{12}$ and $R^{12}$ is $C_{1-8}$alkyl. In another embodiment is a compound of Formula (II), or a pharmaceutically acceptable salt thereof, wherein $R^{11}$ is phenyl substituted with 1 $R^{12}$ and $R^{12}$ is —CH$_3$. In another embodiment is a compound of Formula (II), or a pharmaceutically acceptable salt thereof, wherein $R^{11}$ is phenyl substituted with 1 $R^{12}$ and $R^{12}$ is $C_{1-8}$haloalkyl. In another embodiment is a compound of Formula (II), or a pharmaceutically acceptable salt thereof, wherein $R^{11}$ is phenyl substituted with 1 $R^{12}$ and $R^{12}$ is —CF$_3$. In another embodiment is a compound of Formula (II), or a pharmaceutically acceptable salt thereof, wherein $R^{11}$ is phenyl substituted with 1 $R^{12}$ and $R^{12}$ is $C_{1-8}$alkoxy. In another embodiment is a compound of Formula (II), or a pharmaceutically acceptable salt thereof, wherein $R^{11}$ is phenyl substituted with 1 $R^{12}$ and $R^{12}$ is —OCH$_3$. In another embodiment is a compound of Formula (II), or a pharmaceutically acceptable salt thereof, wherein $R^{11}$ is phenyl substituted with 1 $R^{12}$ and $R^{12}$ is —C(O)$R^{13}$. In another embodiment is a compound of Formula (II), or a pharmaceutically acceptable salt thereof, wherein $R^{11}$ is —$C_{1-8}$alkyl-$C_{6-10}$aryl optionally substituted with 1, 2, 3, or 4 $R^{12}$. In another embodiment is a compound of Formula (II), or a pharmaceutically acceptable salt thereof, wherein $R^{11}$ is unsubstituted —$C_{1-8}$alkyl-$C_{6-10}$aryl. In another embodiment is a compound of Formula (II), or a pharmaceutically acceptable salt thereof, wherein $R^{11}$ is —$C_{1-8}$alkyl-$C_{6-10}$aryl substituted with 1, 2, 3, or 4 $R^{12}$. In another embodiment is a compound of Formula (II), or a pharmaceutically acceptable salt thereof, wherein $R^{11}$ is —$C_{1-8}$alkyl-$C_{6-10}$aryl substituted with 1, 2, or 3 $R^{12}$. In another embodiment is a compound of Formula (II), or a pharmaceutically acceptable salt thereof, wherein $R^{11}$ is —$C_{1-8}$alkyl-$C_{6-10}$aryl substituted with 1 or 2 $R^{12}$. In another embodiment is a compound of Formula (II), or a pharmaceutically acceptable salt thereof, wherein $R^{11}$ is —$C_{1-8}$alkyl-$C_{6-10}$aryl substituted with 1 or 2 $R^{12}$ and each $R^{12}$ is independently selected from halogen, $C_{1-8}$alkyl, $C_{1-8}$haloalkyl, and $C_{1-8}$alkoxy. In another embodiment is a compound of Formula (II), or a pharmaceutically acceptable salt thereof, wherein $R^{11}$ is —$C_{1-8}$alkyl-$C_{6-10}$aryl substituted with 1 or 2 $R^{12}$ and each $R^{12}$ is independently selected from $C_{1-8}$alkyl, $C_{1-8}$alkoxy, and —$C(O)R^{13}$. In another embodiment is a compound of Formula (II), or a pharmaceutically acceptable salt thereof, wherein $R^{11}$ is —$C_{1-8}$alkyl-$C_{6-10}$aryl substituted with 1 or 2 $R^{12}$ and each $R^{12}$ is independently selected from $C_{1-8}$alkyl, $C_{1-8}$haloalkyl, and $C_{1-8}$alkoxy. In another embodiment is a compound of Formula (II), or a pharmaceutically acceptable salt thereof, wherein $R^{11}$ is —$C_{1-8}$alkyl-$C_{6-10}$aryl substituted with 1 or 2 $R^{12}$ and each $R^{12}$ is independently selected from $C_{1-8}$alkyl and $C_{1-8}$alkoxy. In another embodiment is a compound of Formula (II), or a pharmaceutically acceptable salt thereof, wherein $R^{11}$ is —$C_{1-8}$alkyl-$C_{6-10}$aryl substituted with 1 $R^{12}$. In another embodiment is a compound of Formula (II), or a pharmaceutically acceptable salt thereof, wherein $R^{11}$ is —$C_{1-8}$alkyl-$C_{6-10}$aryl substituted with 1 $R^{12}$ and $R^{12}$ is selected from halogen, $C_{1-8}$alkyl, $C_{1-8}$haloalkyl, and $C_{1-8}$alkoxy. In another embodiment is a compound of Formula (II), or a pharmaceutically acceptable salt thereof, wherein $R^{11}$ is —$C_{1-8}$alkyl-$C_{6-10}$aryl substituted with 1 $R^{12}$ and $R^{12}$ is selected from $C_{1-8}$alkyl, $C_{1-8}$alkoxy, and —$C(O)R^{13}$. In another embodiment is a compound of Formula (II), or a pharmaceutically acceptable salt thereof, wherein $R^{11}$ is —$C_{1-8}$alkyl-$C_{6-10}$aryl substituted with 1 $R^{12}$ and $R^{12}$ is selected from $C_{1-8}$alkyl and $C_{1-8}$alkoxy. In another embodiment is a compound of Formula (II), or a pharmaceutically acceptable salt thereof, wherein $R^{11}$ is —$C_{1-8}$alkyl-$C_{6-10}$aryl substituted with 1 $R^{12}$ and $R^{12}$ is halogen. In another embodiment is a compound of Formula (II), or a pharmaceutically acceptable salt thereof, wherein $R^{11}$ is —$C_{1-8}$alkyl-$C_{6-10}$aryl substituted with 1 $R^{12}$ and $R^{12}$ is —F. In another embodiment is a compound of Formula (II), or a pharmaceutically acceptable salt thereof, wherein $R^{11}$ is —$C_{1-8}$alkyl-$C_{6-10}$aryl substituted with 1 $R^{12}$ and $R^{12}$ is —Cl. In another embodiment is a compound of Formula (II), or a pharmaceutically acceptable salt thereof, wherein $R^{11}$ is —$C_{1-8}$alkyl-$C_{6-10}$aryl substituted with 1 $R^{12}$ and $R^{12}$ is $C_{1-8}$alkyl. In another embodiment is a compound of Formula (II), or a pharmaceutically acceptable salt thereof, wherein $R^{11}$ is —$C_{1-8}$alkyl-$C_{6-10}$aryl substituted with 1 $R^{12}$ and $R^{12}$ is —$CH_3$. In another embodiment is a compound of Formula (II), or a pharmaceutically acceptable salt thereof, wherein $R^{11}$ is —$C_{1-8}$alkyl-$C_{6-10}$aryl substituted with 1 $R^{12}$ and $R^{12}$ is $C_{1-8}$haloalkyl. In another embodiment is a compound of Formula (II), or a pharmaceutically acceptable salt thereof, wherein $R^{11}$ is —$C_{1-8}$alkyl-$C_{6-10}$aryl substituted with 1 $R^{12}$ and $R^{12}$ is —$CF_3$. In another embodiment is a compound of Formula (II), or a pharmaceutically acceptable salt thereof, wherein $R^{11}$ is —$C_{1-8}$alkyl-$C_{6-10}$aryl substituted with 1 $R^{12}$ and $R^{12}$ is $C_{1-8}$alkoxy. In another embodiment is a compound of Formula (II), or a pharmaceutically acceptable salt thereof, wherein $R^{11}$ is —$C_{1-8}$alkyl-$C_{6-10}$aryl substituted with 1 $R^{12}$ and $R^{12}$ is —$OCH_3$. In another embodiment is a compound of Formula (II), or a pharmaceutically acceptable salt thereof, wherein $R^{11}$ is —$C_{1-8}$alkyl-$C_{6-10}$aryl substituted with 1 $R^{12}$ and $R^{12}$ is —$C(O)R^{13}$. In another embodiment is a compound of Formula (II), or a pharmaceutically acceptable salt thereof, wherein $R^{11}$ is —$CH_2$-phenyl optionally substituted with 1, 2, 3, or 4 $R^{12}$. In another embodiment is a compound of Formula (II), or a pharmaceutically acceptable salt thereof, wherein $R^{11}$ is unsubstituted —$CH_2$-phenyl. In another embodiment is a compound of Formula (II), or a pharmaceutically acceptable salt thereof, wherein $R^{11}$ is —$CH_2$-phenyl substituted with 1, 2, 3, or 4 $R^{12}$. In another embodiment is a compound of Formula (II), or a pharmaceutically acceptable salt thereof, wherein $R^{11}$ is —$CH_2$-phenyl substituted with 1, 2, or 3 $R^{12}$. In another embodiment is a compound of Formula (II), or a pharmaceutically acceptable salt thereof, wherein $R^{11}$ is —$CH_2$-phenyl substituted with 1 or 2 $R^{12}$. In another embodiment is a compound of Formula (II), or a pharmaceutically acceptable salt thereof, wherein $R^{11}$ is —$CH_2$-phenyl substituted with 1 or 2 $R^{12}$ and each $R^{12}$ is independently selected from halogen, $C_{1-8}$alkyl, $C_{1-8}$haloalkyl, and $C_{1-8}$alkoxy. In another embodiment is a compound of Formula (II), or a pharmaceutically acceptable salt thereof, wherein $R^{11}$ is —$CH_2$-phenyl substituted with 1 or 2 $R^{12}$ and each $R^{12}$ is independently selected from $C_{1-8}$alkyl, $C_{1-8}$alkoxy, and —$C(O)R^{13}$. In another embodiment is a compound of Formula (II), or a pharmaceutically acceptable salt thereof, wherein $R^{11}$ is —$CH_2$-phenyl substituted with 1 or 2 $R^{12}$ and each $R^{12}$ is independently selected from $C_{1-8}$alkyl, $C_{1-8}$haloalkyl, and $C_{1-8}$alkoxy. In another embodiment is a compound of Formula (II), or a pharmaceutically acceptable salt thereof, wherein $R^{11}$ is —$CH_2$-phenyl substituted with 1 or 2 $R^{12}$ and each $R^{12}$ is independently selected from $C_{1-8}$alkyl and $C_{1-8}$alkoxy. In another embodiment is a compound of Formula (II), or a pharmaceutically acceptable salt thereof, wherein $R^{11}$ is —$CH_2$-phenyl substituted with 1 $R^{12}$. In another embodiment is a compound of Formula (II), or a pharmaceutically acceptable salt thereof, wherein $R^{11}$ is —$CH_2$-phenyl substituted with 1 $R^{12}$ and $R^{12}$ is selected from halogen, $C_{1-8}$alkyl, $C_{1-8}$haloalkyl, and $C_{1-8}$alkoxy. In another embodiment is a compound of Formula (II), or a pharmaceutically acceptable salt thereof, wherein $R^{11}$ is —$CH_2$-phenyl substituted with 1 $R^{12}$ and $R^{12}$ is selected from $C_{1-8}$alkyl, $C_{1-8}$alkoxy, and —$C(O)R^{13}$. In another embodiment is a compound of Formula (II), or a pharmaceutically acceptable salt thereof, wherein $R^{11}$ is —$CH_2$-phenyl substituted with 1 $R^{12}$ and $R^{12}$ is selected from $C_{1-8}$alkyl and $C_{1-8}$alkoxy. In another embodiment is a compound of Formula (II), or a pharmaceutically acceptable salt thereof, wherein $R^{11}$ is —$CH_2$-phenyl substituted with 1 $R^{12}$ and $R^{12}$ is halogen. In another embodiment is a compound of Formula (II), or a pharmaceutically acceptable salt thereof, wherein $R^{11}$ is —$CH_2$-phenyl with 1 $R^{12}$ and $R^{12}$ is —F. In another embodiment is a compound of Formula (II), or a pharmaceutically acceptable salt thereof, wherein $R^{11}$ is —$CH_2$-phenyl substituted with 1 $R^{12}$ and $R^{12}$ is —Cl. In another embodiment is a compound of Formula (II), or a pharmaceutically acceptable salt thereof, wherein $R^{11}$ is —$CH_2$-phenyl substituted with 1 $R^{12}$ and $R^{12}$ is $C_{1-8}$alkyl. In another embodiment is a compound of Formula (II), or a pharmaceutically acceptable salt thereof, wherein $R^{11}$ is —$CH_2$-phenyl substituted with 1 $R^{12}$ and $R^{12}$ is —$CH_3$. In another embodiment is a compound of Formula (II), or a pharmaceutically acceptable salt thereof, wherein $R^{11}$ is —$CH_2$-phenyl substituted with 1 $R^{12}$ and $R^{12}$ is $C_{1-8}$haloalkyl. In another embodiment is a compound of Formula (II), or a pharmaceutically acceptable salt thereof, wherein $R^{11}$ is —$CH_2$-phenyl substituted with 1 $R^{12}$ and $R^{12}$ is —$CF_3$. In another embodiment is a compound of Formula (II), or a pharmaceutically acceptable salt thereof, wherein $R^{11}$ is —$CH_2$-phenyl substituted with 1 $R^{12}$ and $R^{12}$ is $C_{1-8}$alkoxy. In another embodiment is a compound of Formula (II), or a pharmaceutically acceptable salt thereof, wherein $R^{11}$ is —CH$_2$-phenyl substituted with 1 $R^{12}$ and $R^{12}$ is —OCH$_3$. In another embodiment is a compound of Formula (II), or a pharmaceutically acceptable salt thereof, wherein $R^{11}$ is —CH$_2$-phenyl substituted with 1 $R^{12}$ and $R^{12}$ is —C(O)R$^{13}$. In another embodiment is a compound of Formula (II), or a pharmaceutically acceptable salt thereof, wherein $R^{11}$ is C$_{2-9}$heteroaryl optionally substituted with 1, 2, 3, or 4 $R^{12}$. In another embodiment is a compound of Formula (II), or a pharmaceutically acceptable salt thereof, wherein $R^{11}$ is unsubstituted C$_{2-9}$heteroaryl. In another embodiment is a compound of Formula (II), or a pharmaceutically acceptable salt thereof, wherein $R^{11}$ is C$_{2-9}$heteroaryl substituted with 1, 2, 3, or 4 $R^{12}$. In another embodiment is a compound of Formula (II), or a pharmaceutically acceptable salt thereof, wherein $R^{11}$ is C$_{2-9}$heteroaryl substituted with 1, 2, or 3 $R^{12}$. In another embodiment is a compound of Formula (II), or a pharmaceutically acceptable salt thereof, wherein $R^{11}$ is C$_{2-9}$heteroaryl substituted with 1 or 2 $R^{12}$. In another embodiment is a compound of Formula (II), or a pharmaceutically acceptable salt thereof, wherein $R^{11}$ is C$_{2-9}$heteroaryl substituted with 1 or 2 $R^{12}$ and each $R^{12}$ is independently selected from halogen, C$_{1-8}$alkyl, C$_{1-8}$haloalkyl, and C$_{1-8}$alkoxy. In another embodiment is a compound of Formula (II), or a pharmaceutically acceptable salt thereof, wherein $R^{11}$ is C$_{2-9}$heteroaryl substituted with 1 or 2 $R^{12}$ and each $R^{12}$ is independently selected from C$_{1-8}$alkyl, C$_{1-8}$alkoxy, and —C(O)R$^{13}$. In another embodiment is a compound of Formula (II), or a pharmaceutically acceptable salt thereof, wherein $R^{11}$ is C$_{2-9}$heteroaryl substituted with 1 or 2 $R^{12}$ and each $R^{12}$ is independently selected from C$_{1-8}$alkyl, C$_{1-8}$haloalkyl, and C$_{1-8}$alkoxy. In another embodiment is a compound of Formula (II), or a pharmaceutically acceptable salt thereof, wherein $R^{11}$ is C$_{2-9}$heteroaryl substituted with 1 or 2 $R^{12}$ and each $R^{12}$ is independently selected from C$_{1-8}$alkyl and C$_{1-8}$alkoxy. In another embodiment is a compound of Formula (II), or a pharmaceutically acceptable salt thereof, wherein $R^{11}$ is C$_{2-9}$heteroaryl substituted with 1 $R^{12}$. In another embodiment is a compound of Formula (II), or a pharmaceutically acceptable salt thereof, wherein $R^{11}$ is C$_{2-9}$heteroaryl substituted with 1 $R^{12}$ and $R^{12}$ is selected from halogen, C$_{1-8}$alkyl, C$_{1-8}$haloalkyl, and C$_{1-8}$alkoxy. In another embodiment is a compound of Formula (II), or a pharmaceutically acceptable salt thereof, wherein $R^{11}$ is C$_{2-9}$heteroaryl substituted with 1 $R^{12}$ and $R^{12}$ is selected from C$_{1-8}$alkyl, C$_{1-8}$alkoxy, and —C(O)R$^{13}$. In another embodiment is a compound of Formula (II), or a pharmaceutically acceptable salt thereof, wherein $R^{11}$ is C$_{2-9}$heteroaryl substituted with 1 $R^{12}$ and $R^{12}$ is selected from C$_{1-8}$alkyl and C$_{1-8}$alkoxy. In another embodiment is a compound of Formula (II), or a pharmaceutically acceptable salt thereof, wherein $R^{11}$ is C$_{2-9}$heteroaryl substituted with 1 $R^{12}$ and $R^{12}$ is halogen. In another embodiment is a compound of Formula (II), or a pharmaceutically acceptable salt thereof, wherein $R^{11}$ is C$_{2-9}$heteroaryl substituted with 1 $R^{12}$ and $R^{12}$ is —F. In another embodiment is a compound of Formula (II), or a pharmaceutically acceptable salt thereof, wherein $R^{11}$ is C$_{2-9}$heteroaryl substituted with 1 $R^{12}$ and $R^{12}$ is —Cl. In another embodiment is a compound of Formula (II), or a pharmaceutically acceptable salt thereof, wherein $R^{11}$ is C$_{2-9}$heteroaryl substituted with 1 $R^{12}$ and $R^{12}$ is C$_{1-8}$alkyl. In another embodiment is a compound of Formula (II), or a pharmaceutically acceptable salt thereof, wherein $R^{11}$ is C$_{2-9}$heteroaryl substituted with 1 $R^{12}$ and $R^{12}$ is —CH$_3$. In another embodiment is a compound of Formula (II), or a pharmaceutically acceptable salt thereof, wherein $R^{11}$ is C$_{2-9}$heteroaryl substituted with 1 $R^{12}$ and $R^{12}$ is C$_{1-8}$haloalkyl. In another embodiment is a compound of Formula (II), or a pharmaceutically acceptable salt thereof, wherein $R^{11}$ is C$_{2-9}$heteroaryl substituted with 1 $R^{12}$ and $R^{12}$ is —CF$_3$. In another embodiment is a compound of Formula (II), or a pharmaceutically acceptable salt thereof, wherein $R^{11}$ is C$_{2-9}$heteroaryl substituted with 1 $R^{12}$ and $R^{12}$ is C$_{1-8}$alkoxy. In another embodiment is a compound of Formula (II), or a pharmaceutically acceptable salt thereof, wherein $R^{11}$ is C$_{2-9}$heteroaryl substituted with 1 $R^{12}$ and $R^{12}$ is —OCH$_3$. In another embodiment is a compound of Formula (II), or a pharmaceutically acceptable salt thereof, wherein $R^{11}$ is C$_{2-9}$heteroaryl substituted with 1 $R^{12}$ and $R^{12}$ is —C(O)R$^{13}$. In another embodiment is a compound of Formula (II), or a pharmaceutically acceptable salt thereof, wherein $R^{11}$ is —C$_{1-8}$alkyl-C$_{2-9}$heteroaryl optionally substituted with 1, 2, 3, or 4 $R^{12}$. In another embodiment is a compound of Formula (II), or a pharmaceutically acceptable salt thereof, wherein $R^{11}$ is unsubstituted —C$_{1-8}$alkyl-C$_{2-9}$heteroaryl. In another embodiment is a compound of Formula (II), or a pharmaceutically acceptable salt thereof, wherein $R^{11}$ is —C$_{1-8}$alkyl-C$_{2-9}$heteroaryl substituted with 1, 2, 3, or 4 $R^{12}$. In another embodiment is a compound of Formula (II), or a pharmaceutically acceptable salt thereof, wherein $R^{11}$ is —C$_{1-8}$alkyl-C$_{2-9}$heteroaryl substituted with 1, 2, or 3 $R^{12}$. In another embodiment is a compound of Formula (II), or a pharmaceutically acceptable salt thereof, wherein $R^{11}$ is —C$_{1-8}$alkyl-C$_{2-9}$heteroaryl substituted with 1 or 2 $R^{12}$. In another embodiment is a compound of Formula (II), or a pharmaceutically acceptable salt thereof, wherein $R^{11}$ is —C$_{1-8}$alkyl-C$_{2-9}$heteroaryl substituted with 1 or 2 $R^{12}$ and each $R^{12}$ is independently selected from halogen, C$_{1-8}$alkyl, C$_{1-8}$haloalkyl, and C$_{1-8}$alkoxy. In another embodiment is a compound of Formula (II), or a pharmaceutically acceptable salt thereof, wherein $R^{11}$ is —C$_{1-8}$alkyl-C$_{2-9}$heteroaryl substituted with 1 or 2 $R^{12}$ and each $R^{12}$ is independently selected from C$_{1-8}$alkyl, C$_{1-8}$alkoxy, and —C(O)R$^{13}$. In another embodiment is a compound of Formula (II), or a pharmaceutically acceptable salt thereof, wherein $R^{11}$ is —C$_{1-8}$alkyl-C$_{2-9}$heteroaryl substituted with 1 or 2 $R^{12}$ and each $R^{12}$ is independently selected from C$_{1-8}$alkyl, C$_{1-8}$haloalkyl, and C$_{1-8}$alkoxy. In another embodiment is a compound of Formula (II), or a pharmaceutically acceptable salt thereof, wherein $R^{11}$ is —C$_{1-8}$alkyl-C$_{2-9}$heteroaryl substituted with 1 or 2 $R^{12}$ and each $R^{12}$ is independently selected from C$_{1-8}$alkyl and C$_{1-8}$alkoxy. In another embodiment is a compound of Formula (II), or a pharmaceutically acceptable salt thereof, wherein $R^{11}$ is —C$_{1-8}$alkyl-C$_{2-9}$heteroaryl substituted with 1 $R^{12}$. In another embodiment is a compound of Formula (II), or a pharmaceutically acceptable salt thereof, wherein $R^{11}$ is —C$_{1-8}$alkyl-C$_{2-9}$heteroaryl substituted with 1 $R^{12}$ and $R^{12}$ is selected from halogen, C$_{1-8}$alkyl, C$_{1-8}$haloalkyl, and C$_{1-8}$alkoxy. In another embodiment is a compound of Formula (II), or a pharmaceutically acceptable salt thereof, wherein $R^{11}$ is —C$_{1-8}$alkyl-C$_{2-9}$heteroaryl substituted with 1 $R^{12}$ and $R^{12}$ is selected from C$_{1-8}$alkyl, C$_{1-8}$alkoxy, and —C(O)R$^{13}$. In another embodiment is a compound of Formula (II), or a pharmaceutically acceptable salt thereof, wherein $R^{11}$ is —C$_{1-8}$alkyl-C$_{2-9}$heteroaryl substituted with 1 $R^{12}$ and $R^{12}$ is selected from C$_{1-8}$alkyl and C$_{1-8}$alkoxy. In another embodiment is a compound of Formula (II), or a pharmaceutically acceptable salt thereof, wherein $R^{11}$ is —C$_{1-8}$alkyl-C$_{2-9}$heteroaryl substituted with 1 $R^{12}$ and $R^{12}$ is halogen. In another embodiment is a compound of Formula (II), or a pharmaceutically acceptable salt thereof, wherein $R^{11}$ is —C$_{1-8}$alkyl-C$_{2-9}$heteroaryl substituted with 1 $R^{12}$ and $R^{12}$ is —F. In another embodiment is a compound of Formula (II), or a pharmaceutically acceptable salt thereof, wherein $R^{11}$ is $-C_{1-8}$alkyl-$C_{2-9}$heteroaryl substituted with 1 $R^{12}$ and $R^{12}$ is —Cl. In another embodiment is a compound of Formula (II), or a pharmaceutically acceptable salt thereof, wherein $R^{11}$ is $-C_{1-8}$alkyl-$C_{2-9}$heteroaryl substituted with 1 $R^{12}$ and $R^{12}$ is $C_{1-8}$alkyl. In another embodiment is a compound of Formula (II), or a pharmaceutically acceptable salt thereof, wherein $R^{11}$ is $-C_{1-8}$alkyl-$C_{2-9}$heteroaryl substituted with 1 $R^{12}$ and $R^{12}$ is —$CH_3$. In another embodiment is a compound of Formula (II), or a pharmaceutically acceptable salt thereof, wherein $R^{11}$ is $-C_{1-8}$alkyl-$C_{2-9}$heteroaryl substituted with 1 $R^{12}$ and $R^{12}$ is $C_{1-8}$haloalkyl. In another embodiment is a compound of Formula (II), or a pharmaceutically acceptable salt thereof, wherein $R^{11}$ is $-C_{1-8}$alkyl-$C_{2-9}$heteroaryl substituted with 1 $R^{12}$ and $R^{12}$ is —$CF_3$. In another embodiment is a compound of Formula (II), or a pharmaceutically acceptable salt thereof, wherein $R^{11}$ is $-C_{1-8}$alkyl-$C_{2-9}$heteroaryl substituted with 1 $R^{12}$ and $R^{12}$ is $C_{1-8}$alkoxy. In another embodiment is a compound of Formula (II), or a pharmaceutically acceptable salt thereof, wherein $R^{11}$ is $-C_{1-8}$alkyl-$C_{2-9}$heteroaryl substituted with 1 $R^{12}$ and $R^{12}$ is —$OCH_3$. In another embodiment is a compound of Formula (II), or a pharmaceutically acceptable salt thereof, wherein $R^{11}$ is $-C_{1-8}$alkyl-$C_{2-9}$heteroaryl substituted with 1 $R^{12}$ and $R^{12}$ is —$C(O)R^{13}$.

In another embodiment is a compound of Formula (II), or a pharmaceutically acceptable salt thereof, wherein $R^3$ is H, —$C(O)R^9$, or —$C(O)OR^9$. In another embodiment is a compound of Formula (II), or a pharmaceutically acceptable salt thereof, wherein $R^3$ is —$C(O)R^9$. In another embodiment is a compound of Formula (II), or a pharmaceutically acceptable salt thereof, wherein $R^3$ is —$C(O)R^9$ and $R^9$ is $C_{1-10}$alkyl. In another embodiment is a compound of Formula (II), or a pharmaceutically acceptable salt thereof, wherein $R^3$ is —$C(O)R^9$ and $R^9$ is $C_{1-6}$alkyl. In another embodiment is a compound of Formula (II), or a pharmaceutically acceptable salt thereof, wherein $R^3$ is —$C(O)R^9$ and $R^9$ is $C_{1-4}$alkyl. In another embodiment is a compound of Formula (II), or a pharmaceutically acceptable salt thereof, wherein $R^3$ is —$C(O)R^9$ and $R^9$ is —$CH_3$. In another embodiment is a compound of Formula (II), or a pharmaceutically acceptable salt thereof, wherein $R^3$ is —$C(O)R^9$ and $R^9$ is —$CH_2CH_3$. In another embodiment is a compound of Formula (II), or a pharmaceutically acceptable salt thereof, wherein $R^3$ is —$C(O)OR^9$. In another embodiment is a compound of Formula (II), or a pharmaceutically acceptable salt thereof, wherein $R^3$ is —$C(O)OR^9$ and $R^9$ is $C_{1-10}$alkyl. In another embodiment is a compound of Formula (II), or a pharmaceutically acceptable salt thereof, wherein $R^3$ is —$C(O)OR^9$ and $R^9$ is $C_{1-6}$alkyl. In another embodiment is a compound of Formula (II), or a pharmaceutically acceptable salt thereof, wherein $R^3$ is —$C(O)OR^9$ and $R^9$ is $C_{1-4}$alkyl. In another embodiment is a compound of Formula (II), or a pharmaceutically acceptable salt thereof, wherein $R^3$ is —$C(O)OR^9$ and $R^9$ is —$CH_3$. In another embodiment is a compound of Formula (II), or a pharmaceutically acceptable salt thereof, wherein $R^3$ is —$C(O)OR^9$ and $R^9$ is —$CH_2CH_3$.

Further embodiments provided herein include combinations of one or more of the particular embodiments set forth above.

In some embodiments is a compound selected from:

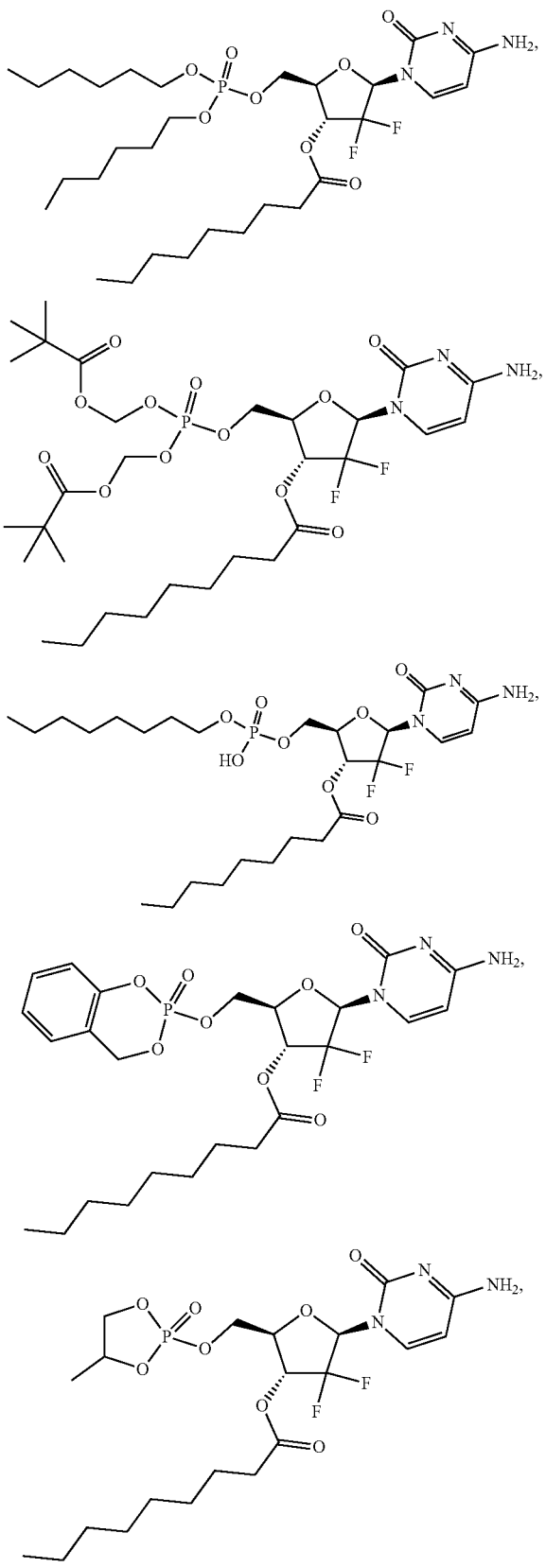

or a pharmaceutically acceptable salt thereof.

In some embodiments is a compound selected from:

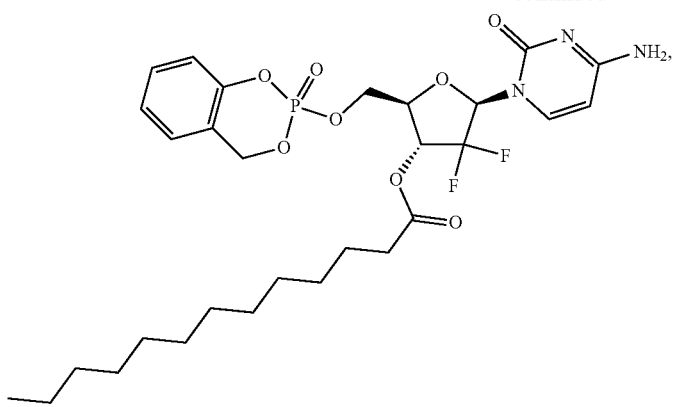
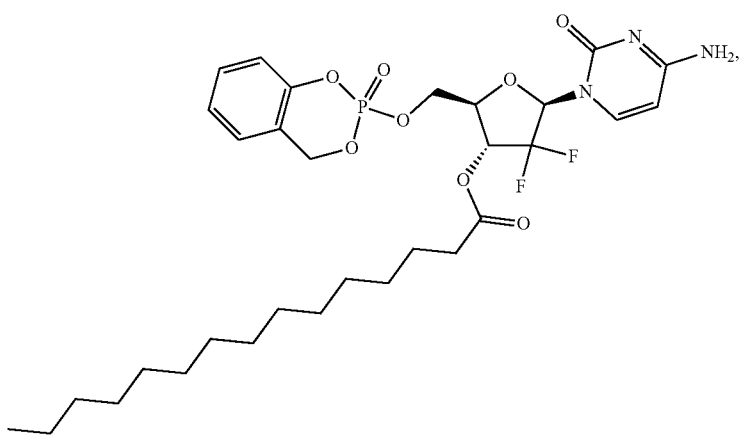
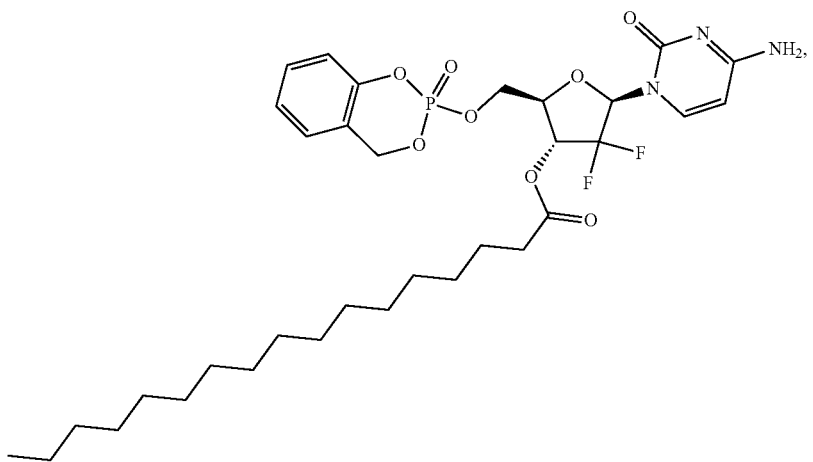

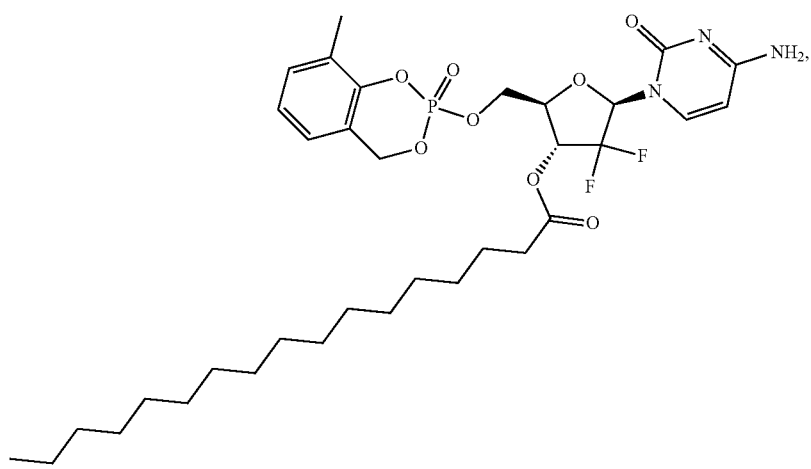
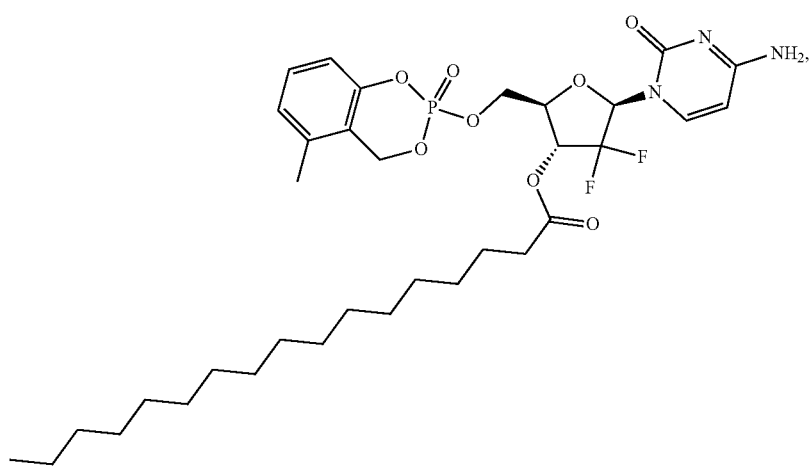
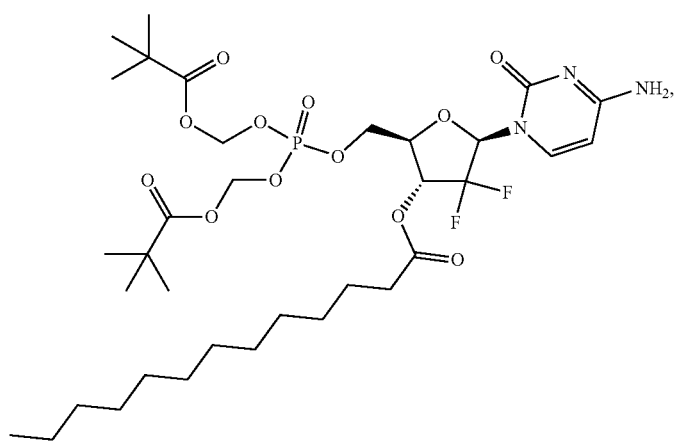

-continued
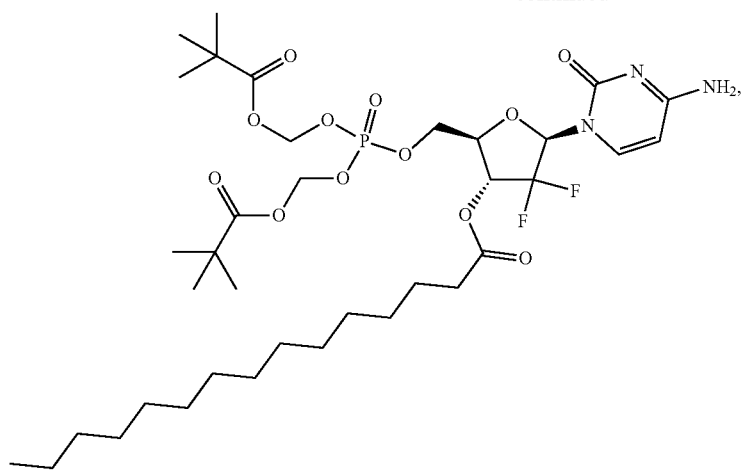
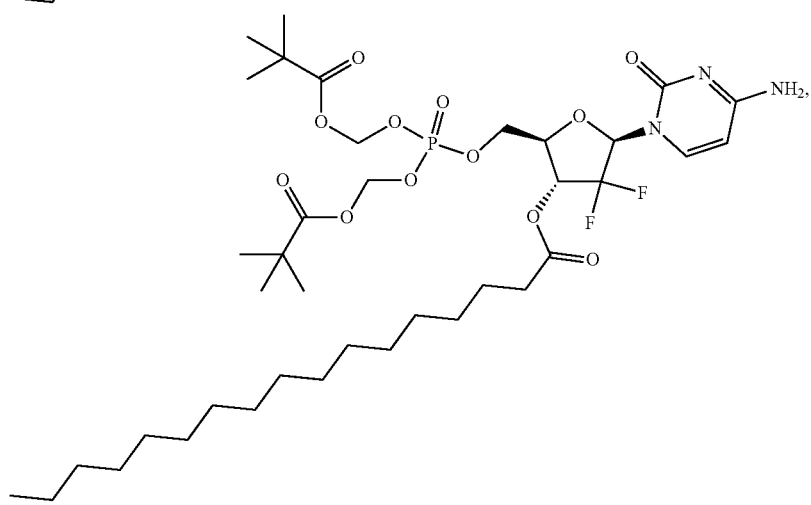
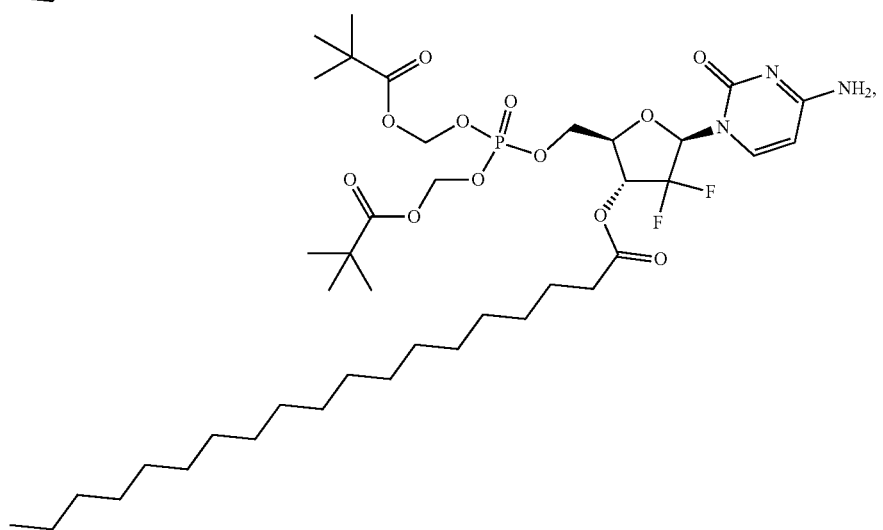
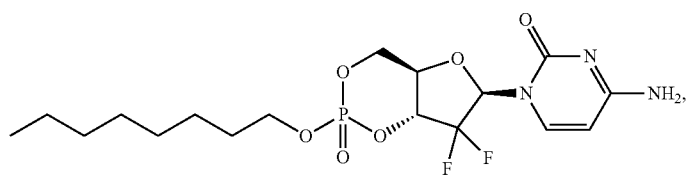

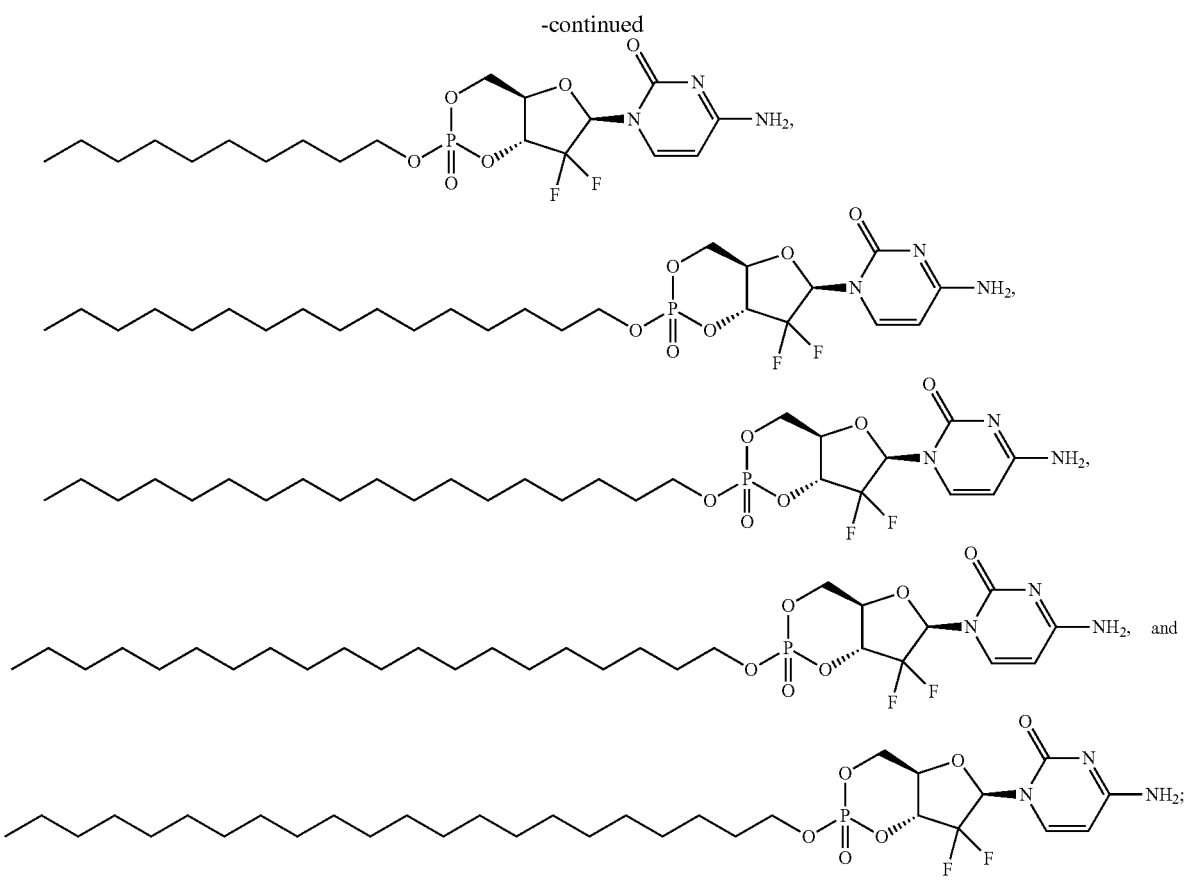
or a pharmaceutically acceptable salt thereof.
In some embodiments is a compound selected from:
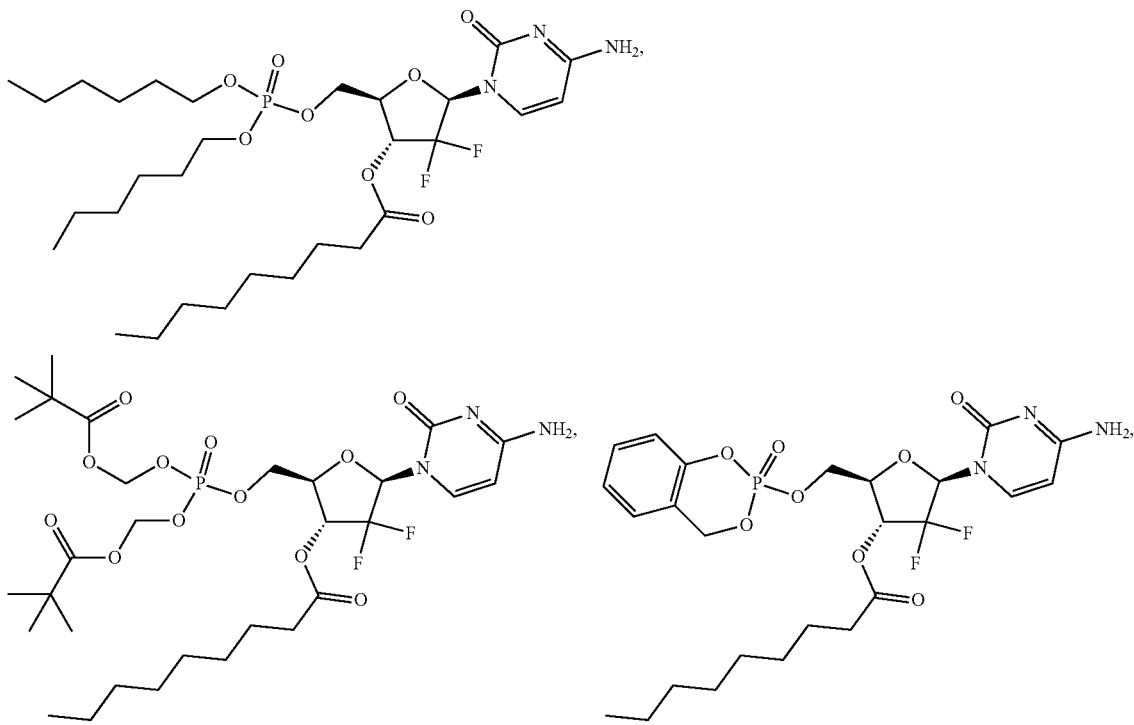

-continued
79
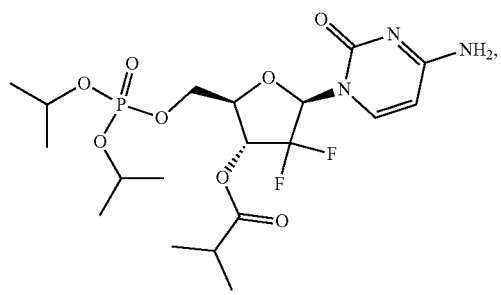
80
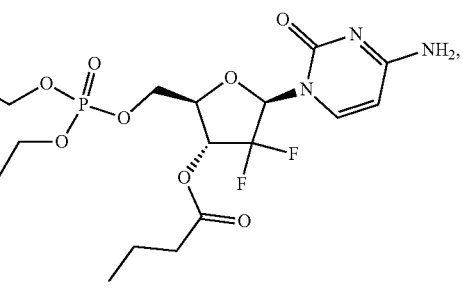
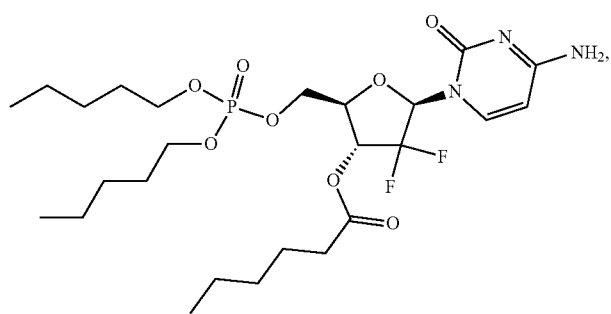
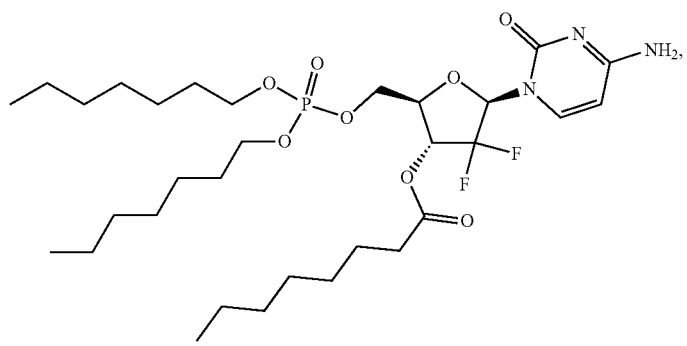
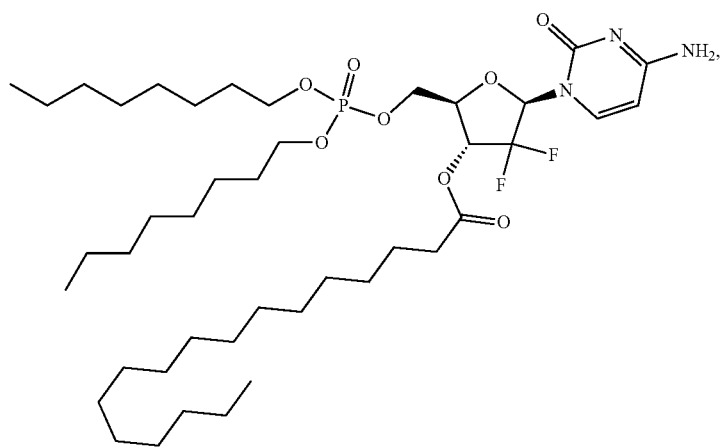

-continued
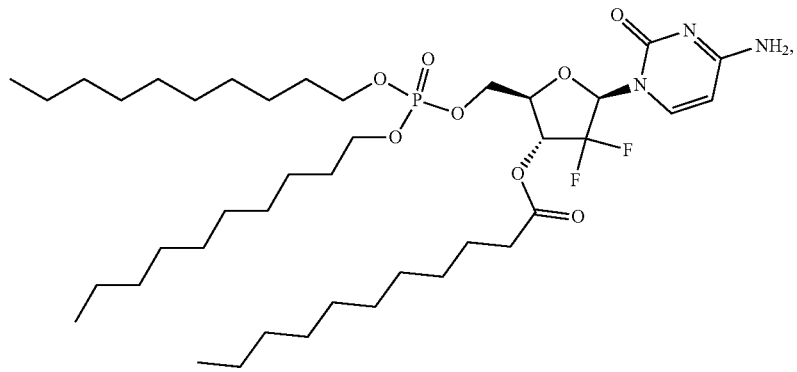
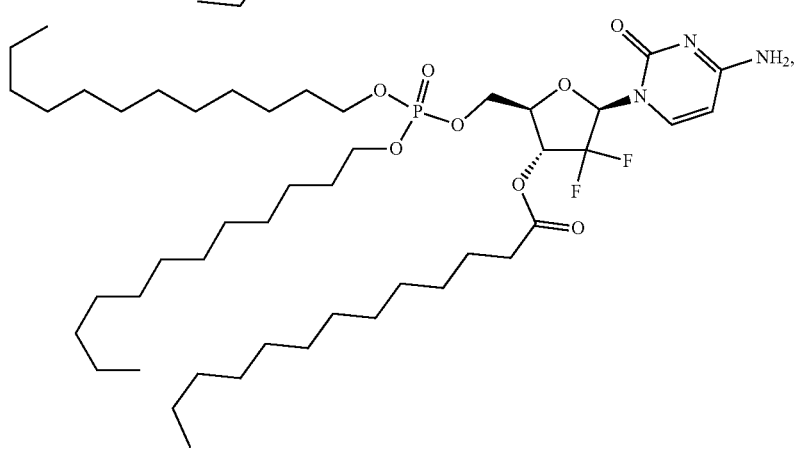
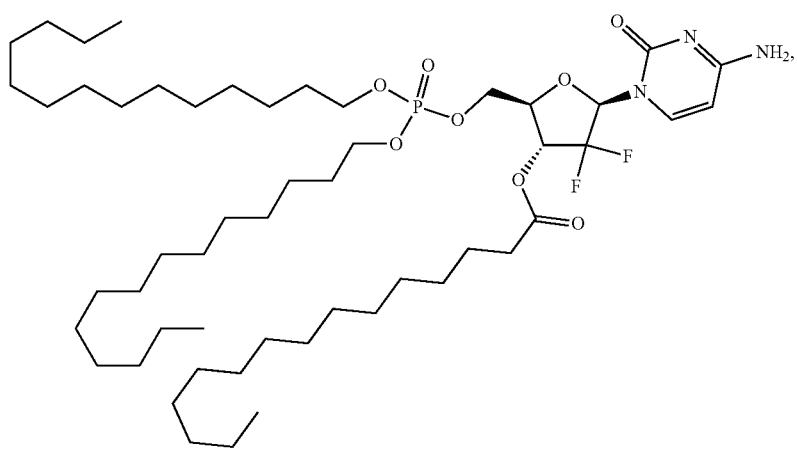
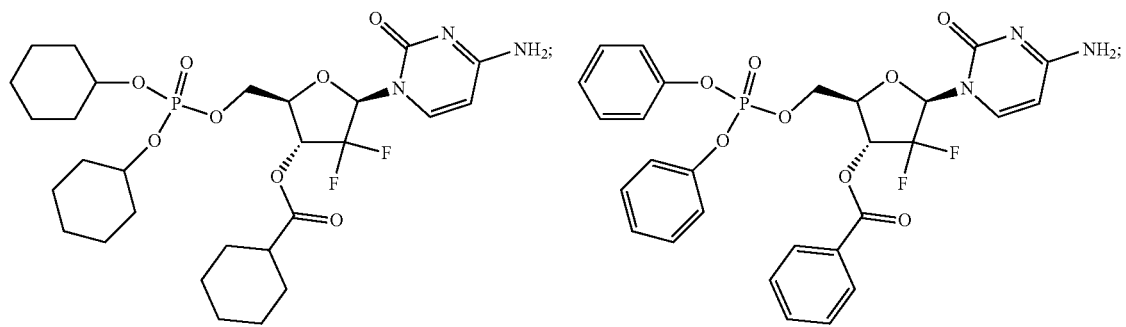

-continued
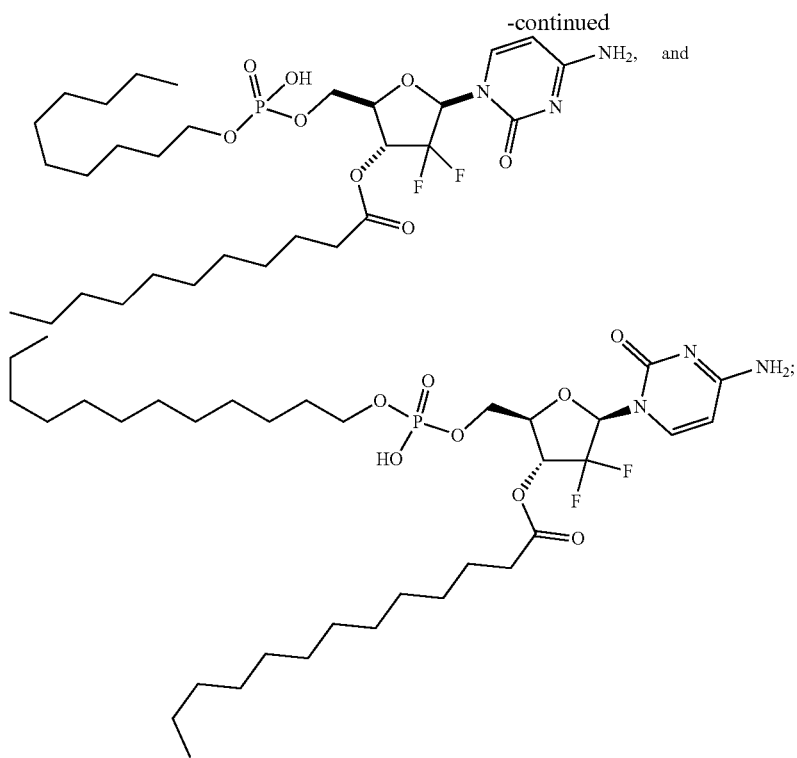
or a pharmaceutically acceptable salt thereof.
In some embodiments is a compound selected from:
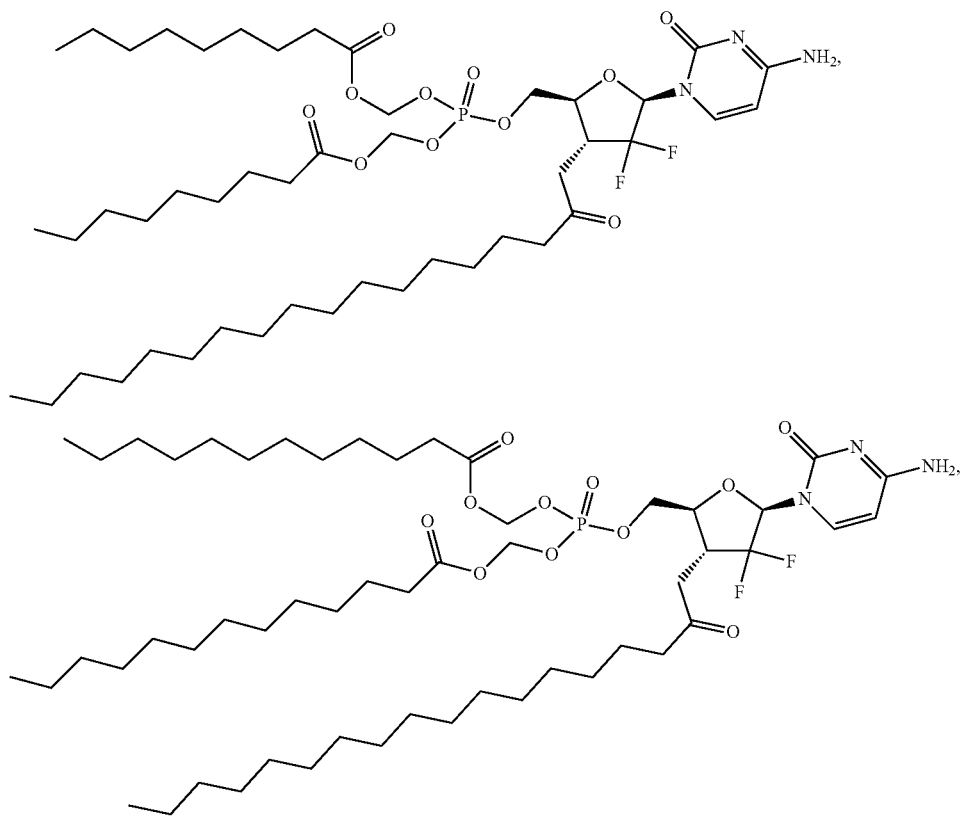

-continued

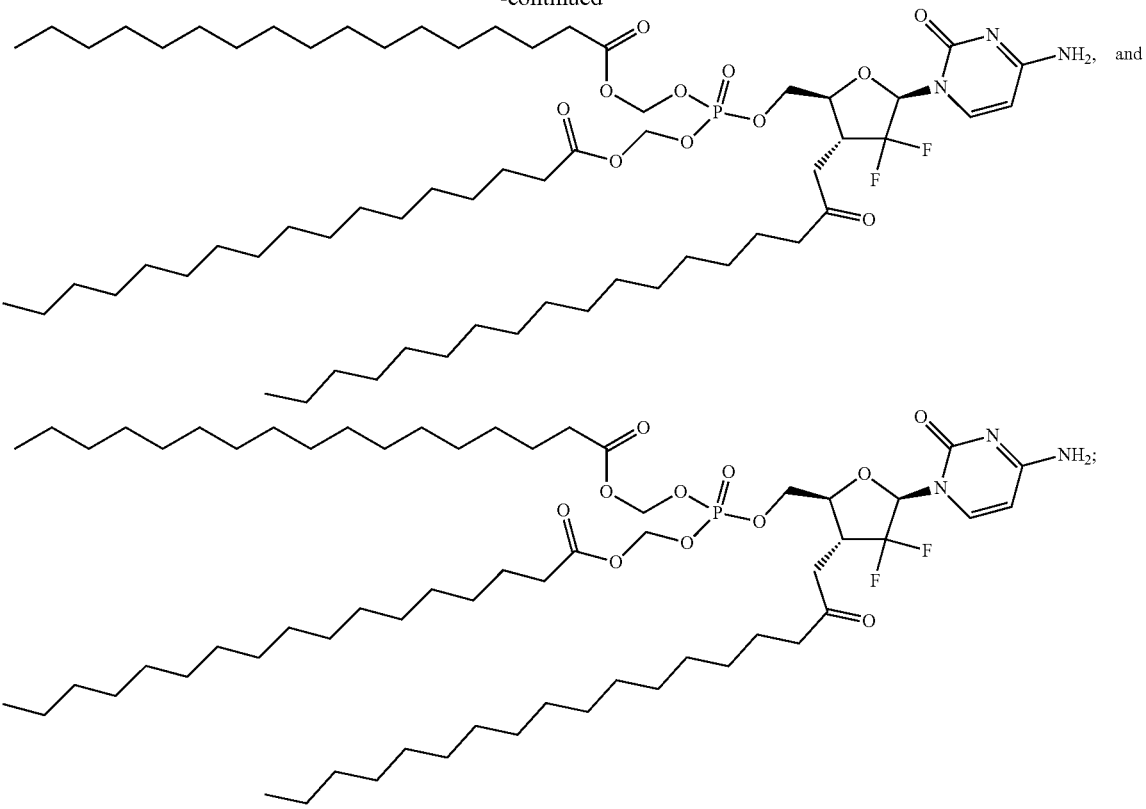

or a pharmaceutically acceptable salt thereof.

Preparation of Compounds

The compounds used in the reactions described herein are made according to organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C.). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (F), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, Phosphorous, sulfur, fluorine, and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and pharmaceutically acceptable salts, esters, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or MeOH. In addition, the compounds provided herein exist in unsolvated as well as solvated forms. In general, the solvated forms are considered equivalent to the unsolvated forms for the purposes of the compounds and methods provided herein.

Pharmaceutical Compositions

In certain embodiments, the compound of Formula (I), (I'), (Ia), (Ib), (Ic), or (II) as described herein is administered as a pure chemical. In some embodiments, the compound of Formula (I), (I'), (Ia), (Ib), (Ic), or (II) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, Pa. (2005)).

Accordingly, provided herein is a pharmaceutical composition comprising at least one compound of Formula (I), (I'), (Ia), (Ib), (Ic), or (II) described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (I), or a pharmaceutically acceptable salt thereof. Another embodiment provides a pharmaceutical composition comprising a pharmaceutically acceptable excipient and a compound of Formula (I'), or a pharmaceutically acceptable salt thereof. Another embodiment provides a pharmaceutical composition comprising a pharmaceutically acceptable excipient and a compound of Formula (Ia), or a pharmaceutically acceptable salt thereof. Another embodiment provides a pharmaceutical composition comprising a pharmaceutically acceptable excipient and a compound of Formula (Ib), or a pharmaceutically acceptable salt thereof. Another embodiment provides a pharmaceutical composition comprising a pharmaceutically acceptable excipient and a compound of Formula (Ic), or a pharmaceutically acceptable salt thereof. Another embodiment provides a pharmaceutical composition comprising a pharmaceutically acceptable excipient and a compound of Formula (II), or a pharmaceutically acceptable salt thereof.

Another embodiment provides a pharmaceutical composition consisting essentially of a pharmaceutically acceptable excipient and a compound of Formula (I), or a pharmaceutically acceptable salt thereof. Another embodiment provides a pharmaceutical composition consisting essentially of a pharmaceutically acceptable excipient and a compound of Formula (I'), or a pharmaceutically acceptable salt thereof. Another embodiment provides a pharmaceutical composition consisting essentially of a pharmaceutically acceptable excipient and a compound of Formula (Ia), or a pharmaceutically acceptable salt thereof. Another embodiment provides a pharmaceutical composition consisting essentially of a pharmaceutically acceptable excipient and a compound of Formula (Ib), or a pharmaceutically acceptable salt thereof. Another embodiment provides a pharmaceutical composition consisting essentially of a pharmaceutically acceptable excipient and a compound of Formula (Ic), or a pharmaceutically acceptable salt thereof. Another embodiment provides a pharmaceutical composition consisting essentially of a pharmaceutically acceptable excipient and a compound of Formula (II), or a pharmaceutically acceptable salt thereof.

In certain embodiments, the compound of Formula (I), (I'), (Ia), (Ib), (Ic), or (II) as described herein is substantially pure, in that it contains less than about 5%, or less than about 1%, or less than about 0.1%, of other organic small molecules, such as contaminating intermediates or by-products that are created, for example, in one or more of the steps of a synthesis method.

In certain embodiments, the compound of Formula (I), (I'), (Ia), (Ib), (Ic), or (II) described herein is formulated for oral, rectal, topical, buccal, parenteral (e.g., subcutaneous, intramuscular, intradermal, or intravenous), vaginal, ophthalmic, or aerosol administration, although the most suitable form of administration in any given case will depend on the degree and severity of the condition being treated and on the nature of the particular compound being used. For example, disclosed compositions are formulated as a unit dose, and/or are formulated for oral or subcutaneous administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate, or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills, and granules, are scored or prepared with coatings and shells, such as enteric coatings and other coatings.

Compositions for inhalation or insufflation include solutions and suspensions in pharmaceutically acceptable aqueous or organic solvents, or mixtures thereof, and powders. Liquid dosage forms for oral administration include pharmaceutically acceptable emulsions, microemulsions, solutions, suspensions, syrups, and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (optionally, cottonseed, groundnut, corn, germ, olive, castor and sesame oils), glycerol, tetrahydrofuryl alcohol, polyethylene glycols and fatty acid esters of sorbitan, cyclodextrins, and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. In some embodiments, the active component is mixed under sterile conditions with a pharmaceutically acceptable carrier, and with any preservatives, buffers, or propellants as required.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

In some embodiments, the compounds described herein are formulated as eye drops for ophthalmic administration.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non ionic surfactants (Tweens, Pluronics, or polyethylene glycol), sorbitan esters, oleic acid, lecithin, amino acids such as glycine, buffers, salts, sugars, or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils such as olive oil, and injectable organic esters such as ethyl oleate and cyclodextrins. Proper fluidity is maintained, for example, by the use of coating materials, such as lecithin, by the maintenance of the required particle size in the case of dispersions, and by the use of surfactants.

Also contemplated are enteral pharmaceutical formulations including a disclosed compound, an enteric material, and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro.

The dose of the composition comprising at least one compound of Formula (I), (I'), (Ia), (Ib), (Ic), or (II) as described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Methods

In some embodiments is a method of treating cancer in a patient in need thereof, comprising administering to the patient a therapeutically effective amount of a compound of Formula (I), (I'), (Ia), (Ib), (Ic), or (II) described herein, or a pharmaceutically acceptable salt thereof. In some embodiments is a method of treating cancer in a patient in need thereof, comprising administering to the patient a therapeutically effective amount of a compound of Formula (I), (I'), (Ia), (Ib), (Ic), or (II) described herein, or a pharmaceutically acceptable salt thereof, wherein the cancer is breast cancer, ovarian cancer, non-small cell lung cancer, pancreatic cancer, or bladder cancer. In some embodiments is a method of treating breast cancer in a patient in need thereof, comprising administering to the patient a therapeutically effective amount of a compound of Formula (I), (I'), (Ia), (Ib), (Ic), or (II) described herein, or a pharmaceutically acceptable salt thereof. In some embodiments is a method of treating ovarian cancer in a patient in need thereof, comprising administering to the patient a therapeutically effective amount of a compound of Formula (I), (I'), (Ia), (Ib), (Ic), or (II) described herein, or a pharmaceutically acceptable salt thereof. In some embodiments is a method of treating non-small cell lung cancer in a patient in need thereof, comprising administering to the patient a therapeutically effective amount of a compound of Formula (I), (I'), (Ia), (Ib), (Ic), or (II) described herein, or a pharmaceutically acceptable salt thereof. In some embodiments is a method of treating pancreatic cancer in a patient in need thereof, comprising administering to the patient a therapeutically effective amount of a compound of Formula (I), (I'), (Ia), (Ib), (Ic), or (II) described herein, or a pharmaceutically acceptable salt thereof. In some embodiments is a method of treating bladder cancer in a patient in need thereof, comprising administering to the patient a therapeutically effective amount of a compound of Formula (I), (I'), (Ia), (Ib), (Ic), or (II) described herein, or a pharmaceutically acceptable salt thereof.

In some embodiments is a method of treating an infectious disease in a patient in need thereof, comprising administering to the patient a therapeutically effective amount of a compound of Formula (I), (I'), (Ia), (Ib), (Ic), or (II) described herein, or a pharmaceutically acceptable salt thereof.

In certain embodiments, a disclosed compound utilized by one or more of the foregoing methods is one of the generic, subgeneric, or specific compounds described herein, such as a compound of Formula (I), (I'), (Ia), (Ib), (Ic), or (II).

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray, or rectally in dosage unit formulations containing conventional non-toxic pharmaceutically acceptable carriers, adjuvants and vehicles. Parenteral administration include subcutaneous injections, intravenous, or intramuscular injections or infusion techniques.

The following examples are provided merely as illustrative of various embodiments and shall not be construed to limit the invention in any way.

EXAMPLES

List of Abbreviations

As used above, and throughout the description of the invention, the following abbreviations, unless otherwise indicated, shall be understood to have the following meanings:

ACN acetonitrile
Bn benzyl
BOC or Boc tert-butyl carbamate
DCC dichloroethane (ClCH$_2$CH$_2$Cl)
DCM N,N'-dicyclohexylcarbodiimide
DIPEA N,N-diisopropylethylamine
DMAP 4-(N,N-dimethylamino)pyridine
DMF dimethylformamide
DMA N,N-dimethylacetamide
DMSO dimethylsulfoxide
equiv equivalent(s)
EDCI 1-(3-dimethylaminopropyl)-3-ethylcarbodiimide
Et ethyl
EtOH ethanol
EtOAc ethyl acetate
HF hydrofluoric acid HMDS bis(trimethylsilyl)amine
HPLC high performance liquid chromatography
Me methyl
MeOH methanol
MMTr 4-methoxytrityl
MMTrCl 4-methoxytrityl chloride
MS mass spectroscopy
NMM N-methylmorpholine
NMR nuclear magnetic resonance
TBHP tert-butyl hydroperoxide
TEA triethylamine
TFA trifluoroacetic acid
THF tetrahydrofuran
TLC thin layer chromatography
TBDMSCl tert-butyldimethylsilyl chloride
TMSCl trimethylsilyl chloride
TMSOTf trimethylsilyl trifluoromethanesulfonate
Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants (J) are reported in Hertz. For proton spectra the solvent peak was used as the reference peak.

Synthesis of Intermediates:
Synthesis of Int-C:

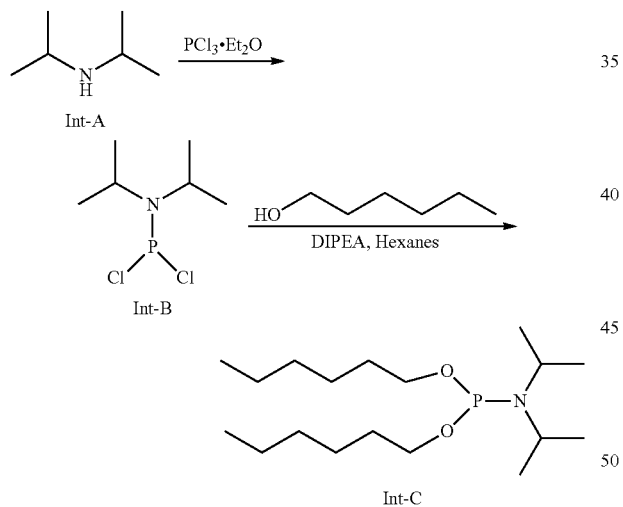

To a solution of PCl$_3$ (7.7 mL, 87.9 mmol) in diethyl ether (60 mL) was added Int-A (16.7 mL, 118.8 mmol) in diethyl ether (60 mL) dropwise over a period of 1 h at 0° C. The reaction mixture was stirred at room temperature for 4 h under argon atmosphere. The reaction mixture was then filtered and washed with diethyl ether (20 mL). The filtrate was concentrated under reduced pressure to give Int-B (13 g) as a colorless liquid. The compound was used directly in the next step without any further purification.

To a solution of 1-hexanol (13.13 g, 128.0 mmol) in hexane (65 mL) was added DIPEA (67.2 mL, 386.0 mmol) followed by Int-B (13.0 g, 64.0 mmol) in hexane (65 mL) dropwise over a period of 1 h at 10° C. The reaction mixture was stirred at room temperature for 4 h and then concentrated under reduced pressure to afford Int-C (16 g) as a light green liquid. The compound was used directly in the next step without any further purification.

Synthesis of Int-E:

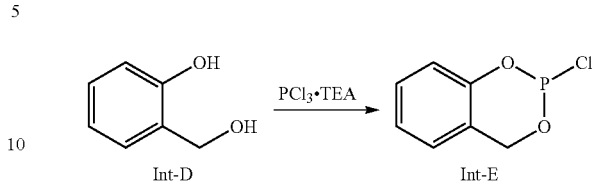

To a solution of Int-D (10.0 g, 80.0 mmol) in diethyl ether (300 mL) was added PCl$_3$ (8.2 mL, 94.2 mmol) over a period of 15 min at −20° C., and then pyridine (19.1 mL, 241.9 mmol) in diethyl ether (200 mL) was added dropwise over a period of 2 h at −20° C. The reaction mixture was allowed to warm to room temperature and maintained at room temperature for 2 h. The reaction mixture was stored at 0° C. for 12 h and filtered. The filtrate was concentrated under reduced pressure to afford crude Int-E (12 g, 80%) as a yellow oil. The compound was used directly in the next step without any further purification.

Synthesis of Int-I:

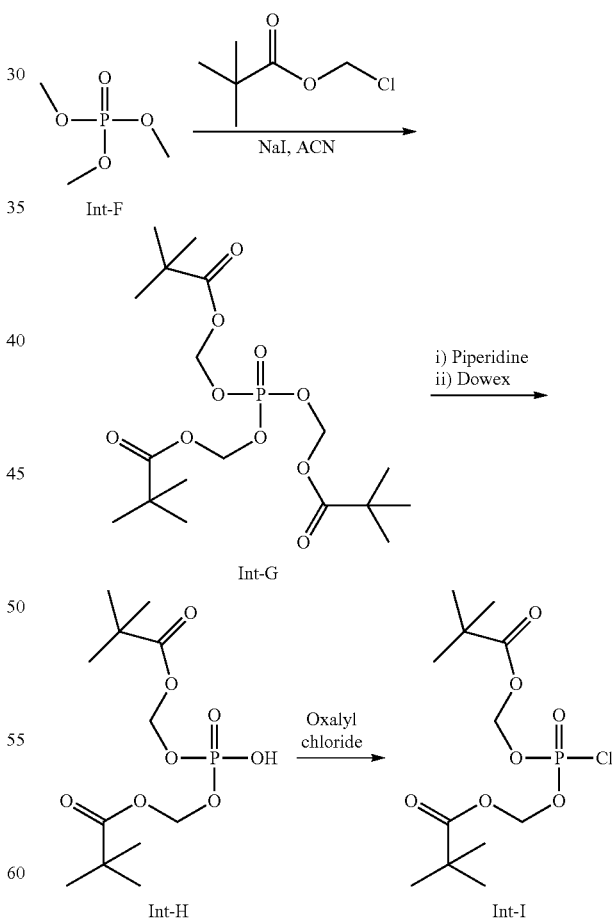

To a stirred solution of Int-F (20 g, 142.8 mmol) in ACN (200 mL) was added NaI (63.8 g, 428.4 mmol) and chloromethylpivalate (85.7 g, 571.4 mmol) at room temperature. The resulting reaction mixture was heated to 80° C. for 3 days. The reaction mixture was cooled and concentrated under reduced pressure. The residue was dissolved in ethyl acetate (200 mL) and washed with water (50 mL) and brine (50 mL). The organic layer was dried over anhydrous $Na_2SO_4$ and filtered. The solvent was evaporated under reduced pressure and the residue was purified by silica gel chromatography to afford Int-G (40 g, 62%) as a light green liquid.

A solution of Int-G (40 g, 90.0 mmol) in piperidine (280 mL) was stirred at room temperature for 12 h. The reaction mixture was distilled. The crude compound was dissolved in water (240 mL) and Dowex $H^+$ resin was added till pH~2 and stirred for 2 h at room temperature. The reaction mixture was filtered and washed with water (2×50 mL). The filtrate was concentrated under reduced pressure to afford pure Int-H (15 g, 51%) as an off-white solid.

To a solution of Int-H (10 g, 30.6 mmol) in DCM (100 mL) was added oxalyl chloride in DCM (100 mL) dropwise at room temperature under argon atmosphere. The reaction mixture was stirred for 2 h at room temperature. The reaction mixture was concentrated under reduced pressure to afford Int-I (10 g) as a yellow oil. The compound was used directly in the next step without any further purification.

Synthesis of Int-J:

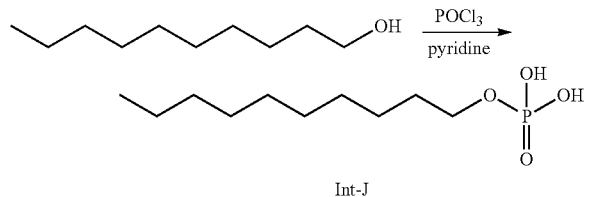

Int-J

To a stirred solution of phosphorus oxychloride (3.7 mL, 39.7 mmol) in distilled tetrahydrofuran (50 mL) was added 1-decanol (5.0 g, 31.59 mmol) as a solution in pyridine (7.7 mL, 95.6 mmol) at 0° C. under argon. The reaction mixture was stirred at 0° C. for 1 h. The reaction was quenched by dropwise addition of saturated aqueous sodium bicarbonate (140 mL) at 0° C. The mixture was poured onto ice water (150 mL) and the mixture was acidified to pH 2 by addition of 6 M hydrochloric acid. The mixture was extracted with ethyl acetate (3×100 mL). The combined organic layers were washed with water (100 mL) and brine (100 mL), dried over anhydrous magnesium sulfate and evaporated to give Int-J (6.50 g, 86%) as a pale yellow semi-solid.

Synthesis of Int-K:

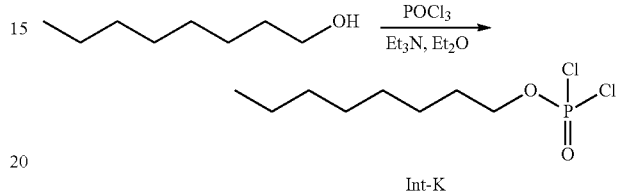

Int-K

Dry $Et_3N$ (15.54 g, 153.58 mmol, 1 eq.) and octan-1-ol (20 g, 153.58 mmol, 1 eq.) in $Et_2O$ (150 mL) was added dropwise with vigorous stirring to $POCl_3$ (23.55 g, 153.58 mmol, 1 eq.) in $Et_2O$ (150 mL) at −78° C. under $N_2$. After addition, the reaction mixture was allowed to warm to 25° C. and stirred for 12 h. The mixture was filtered and the filtrate was concentrated in reduced pressure to yield 1-dichlorophosphoryloxyoctane (20 g, 53% yield) as a yellow liquid. $^1$H NMR (400 MHz, $CDCl_3$) δ 4.36 (td, J=6.4, 9.8 Hz, 2H), 1.90-1.78 (m, 2H), 1.51-1.42 (m, 2H), 1.39-1.28 (m, 8H), 1.02-0.81 (m, 3H).

Example 1: Synthesis of (2R,3R,5R)-5-(4-amino-2-oxopyrimidin-1(2H)-yl)-2-(((bis(hexyloxy)phosphoryl)oxy)methyl)-4,4-difluorotetrahydrofuran-3-yl nonanoate (Compound 1)

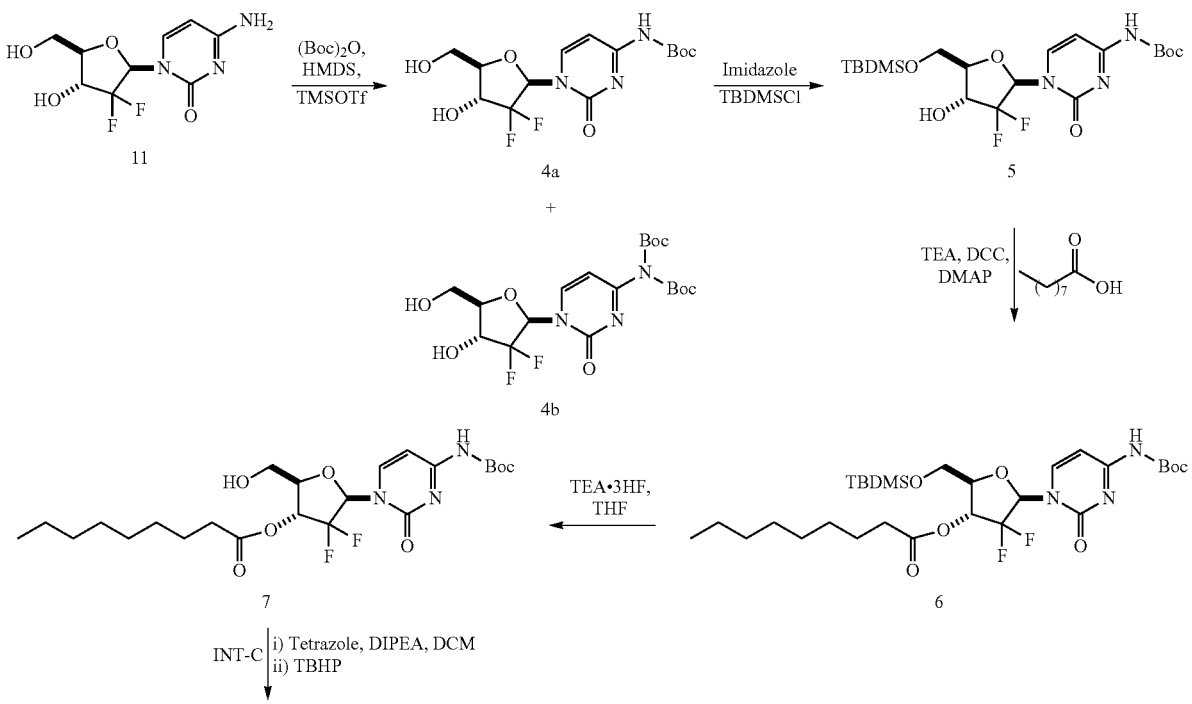

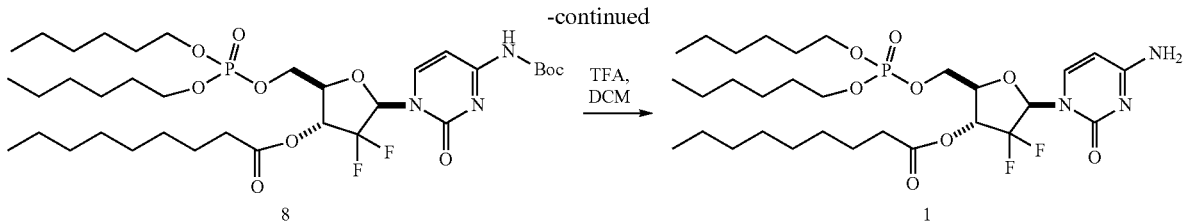

To a suspension of 11 (40 g, 152.0 mmol) in HMDS (73.46 g, 456.2 mmol) were added DMAP (1.8 g, 15.2 mmol) and TMSOTf (1.01 g, 4.56 mmol) at 0° C. The resulting mixture was stirred at room temperature for 12 h. Boc-anhydride (165 g, 760 mmol) was then added dropwise over a period of 1 h at 0° C. The resulting reaction mixture was stirred at room temperature for 16 h and then methanol (400 mL) and TEA (200 mL) were added at 0° C. for 1 h. The resulting reaction mixture was stirred at room temperature for 20 h. The reaction mixture was concentrated under reduced pressure and the residue was diluted with water (100 mL) and extracted with ethyl acetate (3×200 mL). The combined organic layers were washed with water (100 mL) and brine (100 mL). The organic layer was dried over anhydrous $Na_2SO_4$, filtered and the solvent was evaporated under reduced pressure. The crude compound was purified by silica gel chromatography to afford 4a (35.0 g, 63%) and 4b (12 g, 17%) as off-white solids.

To a stirred solution of 4a (35.0 g, 96.4 mmol) in pyridine (350 mL) at 0° C. were added imidazole (9.18 g, 134.9 mmol) and TBDMSCl (26.03 g, 173.5 mmol). The reaction mixture was stirred at room temperature for 8 h. The pyridine was evaporated under reduced pressure and the residue was co-distilled with toluene repeatedly 3 times. The crude reaction mass was diluted with water (100 mL) and extracted with ethyl acetate (3×200 mL). The combined organic layers were washed with water (100 mL) and brine (100 mL). The organic layer was dried over anhydrous $Na_2SO_4$, filtered, and the solvent was evaporated under reduced pressure. The crude product was purified by silica gel chromatography to afford 5 (30 g, 65%) as an off-white solid.

To a solution of 5 (30 g, 62.8 mmol) in 1,4-dioxane (300 mL) at 0° C. was added TEA (43.7 mL, 314.4 mmol), DCC (38.86 g, 188.0 mmol), and DMAP (767 mg, 6.2 mmol) followed by nonanoic acid (29.81 g, 188 mmol). The reaction mixture was stirred at room temperature overnight. The solvent was evaporated under reduced pressure and the residue was dissolved in DCM (500 mL) and washed with water (100 mL) and brine (100 mL). The organic layer was dried over anhydrous $Na_2SO_4$ and filtered. The solvent was evaporated under reduced pressure to give the crude compound which was purified by silica gel chromatography to afford 6 (30 g, 77%) as a light brown liquid.

To a solution of 6 (30 g, 48.6 mmol) in THF (300 mL), was added TEA.3HF (39.14 g, 243 mmol) dropwise at 0° C. The reaction mixture was slowly warmed to room temperature and stirred for 12 h at room temperature. The solvent was evaporated under reduced pressure and the residue was dissolved in ethyl acetate (500 mL) and washed with water (100 mL) and brine (100 mL). The organic layer was dried over anhydrous $Na_2SO_4$ and filtered. The solvent was evaporated under reduced pressure to give the crude compound which was purified by silica gel chromatography to afford 7 (20 g, 82%) as a light brown liquid.

To a stirred solution of 7 (5 g, 9.9 mmol) in DCM (100 mL), was added DIPEA (8.65 mL, 49.6 mmol) and tetrazole (1.74 g, 24.8 mmol). Int-C (8.27 g, 24.8 mmol) in DCM (20 mL) was then added dropwise at 0° C. over 15 min. The reaction mixture was stirred at room temperature for 16 h and then TBHP (5.96 ml; 5M in decane, 29.8 mmol) was added to the reaction mixture dropwise at 0° C. The resulting reaction mixture was stirred for 6 h at room temperature. The reaction mixture was concentrated under reduced pressure and the residue was dissolved in ethyl acetate (100 mL) and washed with water (50 mL) and brine (50 mL). The organic layer was dried over anhydrous $Na_2SO_4$ filtered solvent was evaporated under reduced pressure to give the crude compound which was purified by silica gel chromatography to afford 8 (2.8 g, 38%) as a red liquid.

To a solution of 8 (2.8 g, 3.72 mmol) in DCM (28 mL) was added TFA (1.42 mL, 18.6 mmol) dropwise at 0° C. The reaction mixture was stirred at room temperature for 16 h. The solvent was evaporated under reduced pressure and the residue was diluted in ethyl acetate (200 mL) and washed with saturated $NaHCO_3$ (2×50 mL). The organic layer was dried over $Na_2SO_4$ and filtered. The solvent was evaporated under reduced pressure to give the crude compound which was purified by silica gel chromatography to afford the title compound (1) (1.3 g, 54%) as a colorless liquid. $^1$H NMR (300 MHz, $d_6$-DMSO): δ 0.83-0.87 (9H, m); 1.25 (22H, broad s); 1.54-1.61 (6H, m); 2.42-2.47 (2H, t); 3.93-3.99 (4H, q); 4.25-4.37 (3H, m); 5.41 (1H, broad m); 5.78-5.80 (1H, d); 6.26 (1H, broad m); 7.48 (2H, broad s); 7.57-7.60 (1H, d). LC-MS (ESI) m/z $(M+H)^+$: 652.5.

Example 2: Synthesis of (2R,3R,5R)-5-(4-amino-2-oxopyrimidin-1(2H)-yl)-4,4-difluoro-2-(((2-oxido-4H-benzo[d][1,3,2]dioxaphosphinin-2-yl)oxy)methyl)tetrahydrofuran-3-yl nonanoate (Compound 2)

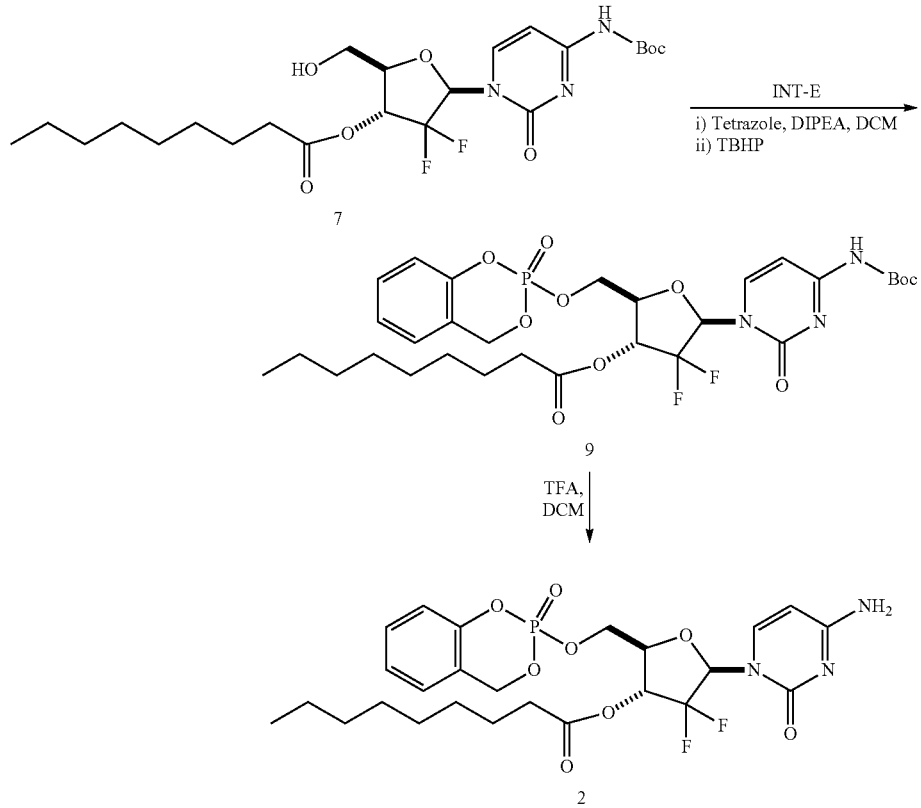

To a solution of 7 (4.5 g, 8.8 mmol) in ACN (90 mL) was added DIPEA (8.8 mL, 49.6 mmol) and a solution of Int-E (3.36 g, 17.8 mmol) in DCM (20 mL) dropwise at 0° C. over 15 min. The reaction mixture was stirred at room temperature for 30 min. TBHP (5.37 mL; 5M in decane, 26.8 mmol) was then added dropwise at 0° C. The reaction mixture was stirred at room temperature for 2 h. The reaction mixture was concentrated under reduced pressure and the residue was dissolved in ethyl acetate (100 mL) and washed with water (50 mL) and brine (50 mL). The organic layer was dried over anhydrous $Na_2SO_4$ and filtered. The solvent was evaporated under reduced pressure to give the crude compound which was purified by silica gel chromatography to afford 9 (1.74 g, 29%) as an off-white solid.

To a solution of 9 (1.74 g, 2.59 mmol) in DCM (34.8 mL) was added TFA (0.98 mL, 12.9 mmol) dropwise at 0° C. The reaction mixture was stirred at room temperature for 16 h. The reaction mixture was concentrated under reduced pressure and the residue was dissolved in ethyl acetate (100 mL) and washed with saturated $NaHCO_3$ (50 mL). The organic layer was dried over anhydrous $Na_2SO_4$ and filtered. The solvent was evaporated under reduced pressure to give the crude compound which was purified by silica gel chromatography to afford the title compound (2) (0.83 g, 56%) as an off-white solid. $^1$H NMR (300 MHz, $d_6$-DMSO): δ 0.84-0.87 (3H, t); 1.25 (10H, broad s); 1.51-1.54 (2H, m); 2.37-2.41 (2H, m); 4.37-4.41 (1H, m); 4.44-4.51 (2H, m); 5.37 (1H, broad s); 5.42-5.57 (2H, m); 5.72-5.75 (1H, m); 6.22 (1H, broad m); 7.11-7.14 (1H, m); 7.19-7.23 (1H, m); 7.28-7.30 (1H, m); 7.35-7.47 (4H, m). LC-MS (ESI) m/z $(M+H)^+$: 572.2.

Example 3: Synthesis of Compound 3

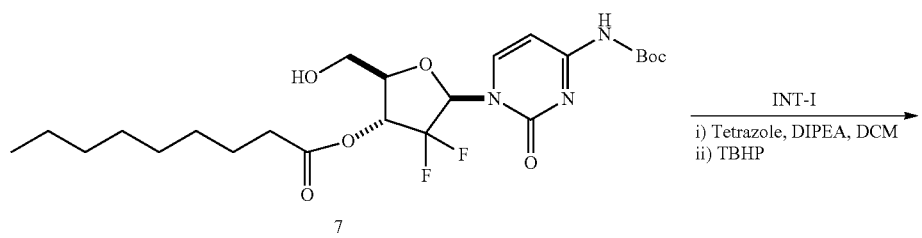

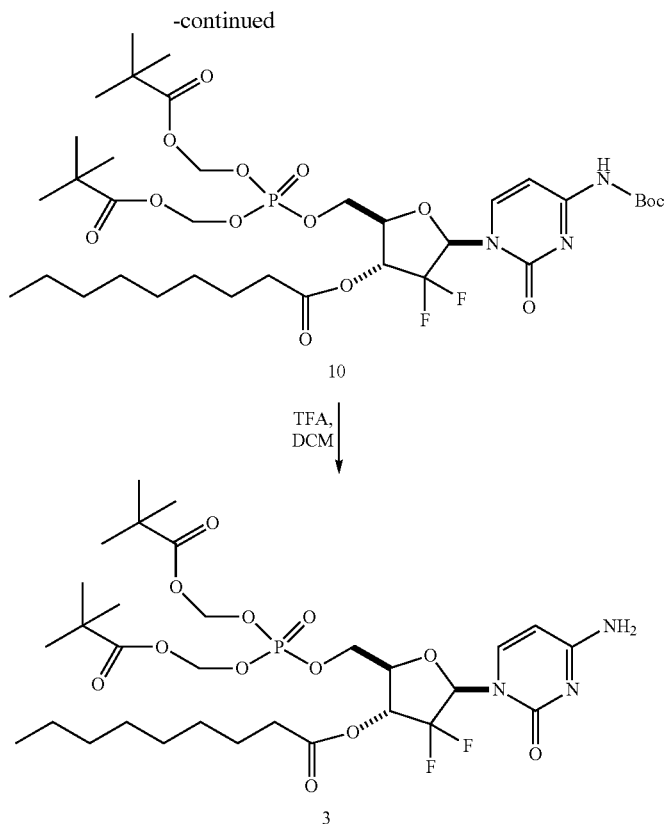

To a solution of 7 (4 g, 7.9 mmol) in DCM (80 mL) was added DIPEA (1.65 mL, 9.4 mmol), DMAP (57 mg, 0.47 mmol), and a solution of Int-I (3.2 g, 9.5 mmol) in DCM (20 mL) dropwise at 0° C. for 15 min. The reaction mixture was stirred at room temperature for 16 h. The reaction mixture was concentrated under reduced pressure and the residue was dissolved in ethyl acetate (100 mL) and washed with water (50 mL) and brine (50 mL). The organic layer was dried over anhydrous $Na_2SO_4$ and filtered. The solvent was evaporated under reduced pressure to afford 10 (3.0 g) as a brown liquid which was used in the next step without further purification.

To a solution of 10 (3.0 g, 3.6 mmol) in DCM (30 mL) was added TFA (1.41 mL, 18.45 mmol) dropwise at 0° C. The reaction mixture was stirred at room temperature for 16 h. The solvent was evaporated under reduced pressure and the residue was diluted in ethyl acetate (100 mL) and washed with saturated $NaHCO_3$ (50 mL). The organic layer was dried over $Na_2SO_4$ and filtered. The solvent was evaporated under reduced pressure to give crude compound which was purified by silica gel chromatography to afford Compound 3 (0.58 g, 33%) as a colorless liquid. $^1$H NMR (300 MHz, $d_6$-DMSO): δ 0.83-0.87 (3H, m); 1.09-1.16 (18H, m); 1.25 (10H, broad s); 1.53-1.60 (2H, m); 2.41-2.46 (2H, t); 4.35-4.37 (3H, broad d); 5.40 (1H, broad s); 5.58-5.63 (4H, d); 5.79-5.82 (1H, d); 6.25 (1H, broad s); 7.46-7.48 (2H, m); 7.57-7.59 (1H, d). LC-MS (ESI) m/z (M+H)$^+$: 712.4.

Examples 4-14

The following compounds were synthesized in a similar manner as described in Example 1.

| Ex. No. | Compound No. | Structure | Chemical Name | LC-MS (ESI) m/z (M + H)$^+$ |
|---|---|---|---|---|
| 4 | 16 | 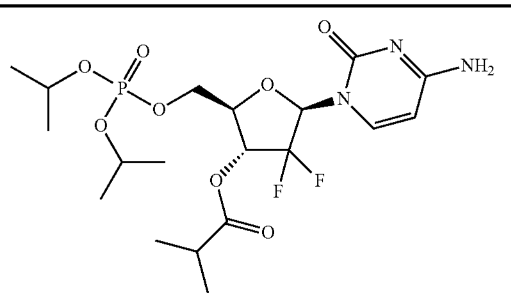 | (2R,3R,5R)-5-(4-amino-2-oxopyrimidin-1(2H)-(((diisopropoxyphosphoryl)oxy)methyl)-4,4-difluorotetrahydrofuran-3-yl isobutyrate | 498.4 |

-continued

| Ex. No. | Compound No. | Structure | Chemical Name | LC-MS (ESI) m/z (M + H)+ |
|---|---|---|---|---|
| 5 | 17 | 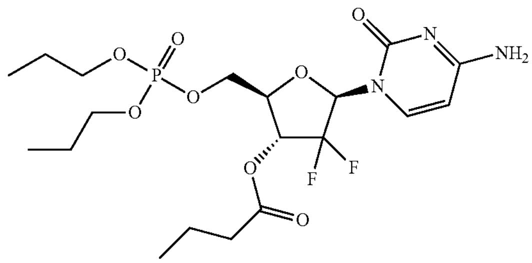 [SMILES: CCCOP(=O)(OCCC)OC[C@H]1O[C@@H](n2ccc(N)nc2=O)C(F)(F)[C@@H]1OC(=O)CCC] | (2R,3R,5R)-5-(4-amino-2-oxopyrimidin-1(2H)-(((dipropoxyphosphoryl)oxy)methyl)-4,4-difluorotetrahydrofuran-3-yl butyrate | 498.4 |
| 6 | 18 | 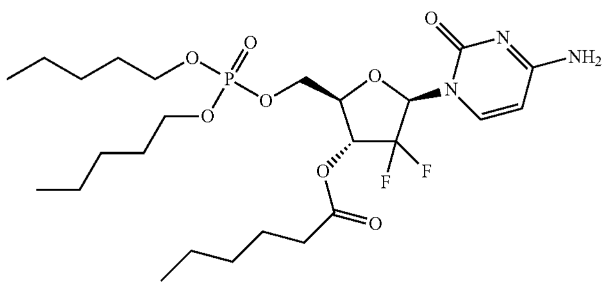 [SMILES: CCCCCOP(=O)(OCCCCC)OC[C@H]1O[C@@H](n2ccc(N)nc2=O)C(F)(F)[C@@H]1OC(=O)CCCCC] | (2R,3R,5R)-5-(4-amino-2-oxopyrimidin-1(2H)-yl)-2-(((bis(pentyloxy)phosphoryl)oxy)methyl)-4,4-difluorotetrahydrofuran-3-yl hexanoate | 582.5 |
| 7 | 19 | 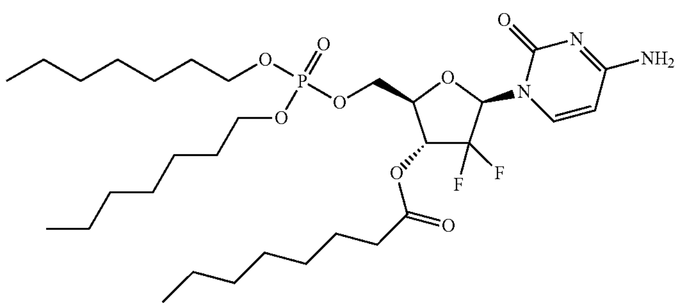 [SMILES: CCCCCCCOP(=O)(OCCCCCCC)OC[C@H]1O[C@@H](n2ccc(N)nc2=O)C(F)(F)[C@@H]1OC(=O)CCCCCCC] | (2R,3R,5R)-5-(4-amino-2-oxopyrimidin-1(2H)-yl)-2-(((bis(heptyloxy)phosphoryl)oxy)methyl)-4,4-difluorotetrahydrofuran-3-yl octanoate | 666.7 |
| 8 | 20 | 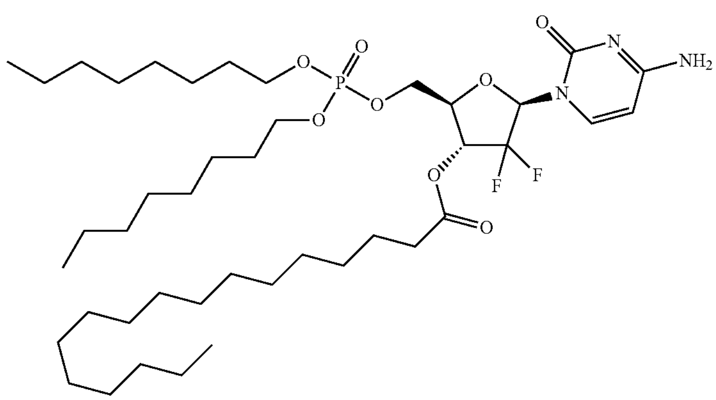 [SMILES: CCCCCCCCCCCCCCCCC(=O)O[C@@H]1[C@@H](COP(=O)(OCCCCCCCC)OCCCCCCCC)O[C@@H](n2ccc(N)nc2=O)C1(F)F] | (2R,3R,5R)-5-(4-amino-2-oxopyrimidin-1(2H)-yl)-2-(((bis(octyloxy)phosphoryl)oxy)methyl)-4,4-difluorotetrahydrofuran-3-yl heptadecanoate | 820.7 |
| 9 | 21 | 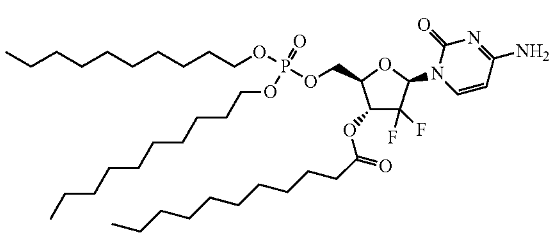 [SMILES: CCCCCCCCCCOP(=O)(OCCCCCCCCCC)OC[C@H]1O[C@@H](n2ccc(N)nc2=O)C(F)(F)[C@@H]1OC(=O)CCCCCCCCCC] | (2R,3R,5R)-5-(4-amino-2-oxopyrimidin-1(2H)-yl)-2-(((bis(decyloxy)phosphoryl)oxy)methyl)-4,4-difluorotetrahydrofuran-3-yl undecanoate | 792.7 |

-continued

| Ex. No. | Compound No. | Structure | Chemical Name | LC-MS (ESI) m/z (M + H)+ |
|---|---|---|---|---|
| 10 | 22 | 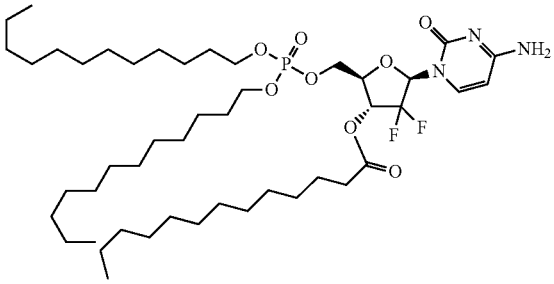 [SMILES: CCCCCCCCCCCCOP(=O)(OCCCCCCCCCCCC)OC[C@H]1O[C@@H](n2ccc(N)nc2=O)C(F)(F)[C@@H]1OC(=O)CCCCCCCCCCCC] | (2R,3R,5R)-5-(4-amino-2-oxopyrimidin-1(2H)-yl)-2-(((bis(dodecyloxy)phosphoryl)oxy)methyl)-4,4-difluorotetrahydrofuran-3-yl tridecanoate | 876.7 |
| 11 | 23 | 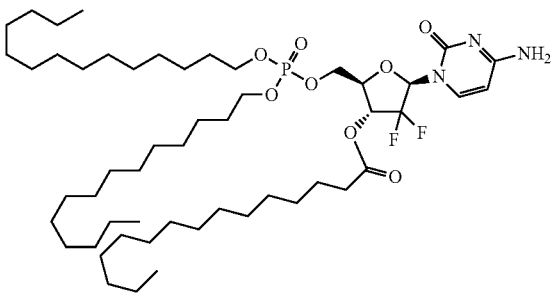 [SMILES: CCCCCCCCCCCCCCOP(=O)(OCCCCCCCCCCCCCC)OC[C@H]1O[C@@H](n2ccc(N)nc2=O)C(F)(F)[C@@H]1OC(=O)CCCCCCCCCCCCCC] | (2R,3R,5R)-5-(4-amino-2-oxopyrimidin-1(2H)-yl)-2-(((bis(tetradecyloxy)phosphoryl)oxy)methyl)-4,4-difluorotetrahydrofuran-3-yl pentadecanoate | 960.8 |
| 12 | 24 | 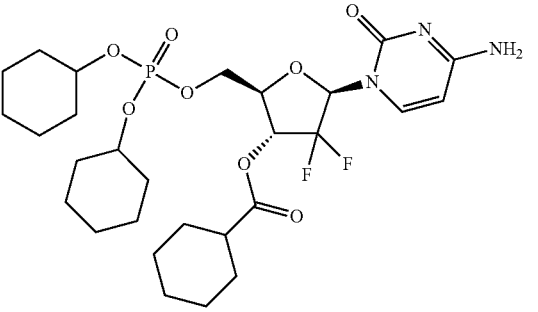 [SMILES: Nc1ccn([C@@H]2O[C@H](COP(=O)(OC3CCCCC3)OC3CCCCC3)[C@@H](OC(=O)C3CCCCC3)C2(F)F)c(=O)n1] | (2R,3R,5R)-5-(4-amino-2-oxopyrimidin-1(2H)-(((bis(cyclohexyloxy)phosphoryl)oxy)methyl)-4,4-difluorotetrahydrofuran-3-yl cyclohexanecarboxylate | 618.5 |
| 13 | 25 | 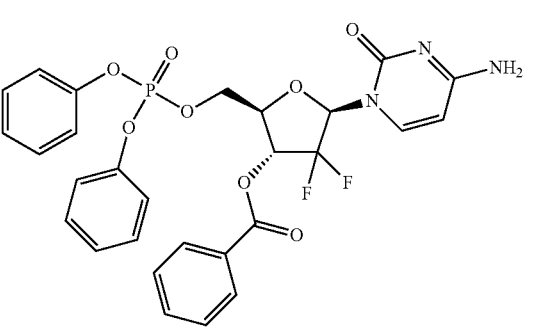 [SMILES: Nc1ccn([C@@H]2O[C@H](COP(=O)(Oc3ccccc3)Oc3ccccc3)[C@@H](OC(=O)c3ccccc3)C2(F)F)c(=O)n1] | (2R,3R,5R)-5-(4-amino-2-oxopyrimidin-1(2H)-yl)-2-(((diphenoxyphosphoryl)oxy)methyl)-4,4-difluorotetrahydrofuran-3-yl benzoate | 600.4 |
| 14 | 26 | 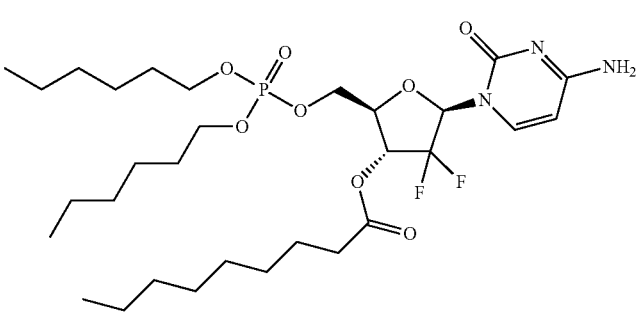 [SMILES: CCCCCCCCC(=O)O[C@@H]1[C@@H](COP(=O)(OCCCCCC)OCCCCCC)O[C@@H](n2ccc(N)nc2=O)C1(F)F] | (2R,3R,5R)-5-(4-amino-2-oxopyrimidin-1(2H)-(((bis(hexyloxy)phosphoryl)oxy)methyl)-4,4-difluorotetrahydrofuran-3-yl nonanoate | 652.5 |

Example 15: Synthesis of (2R,3R,5R)-5-(4-amino-2-oxopyrimidin-1(2H)-yl)-2-((((decyloxy)(hydroxy)phosphoryl)oxy)methyl)-4,4-difluorotetrahydrofuran-3-yl undecanoate (Compound 15)
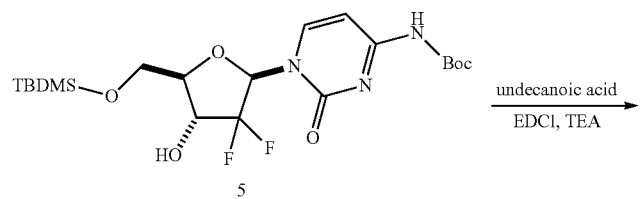
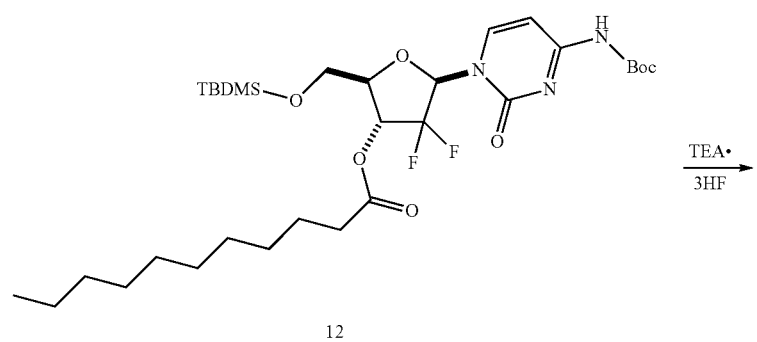
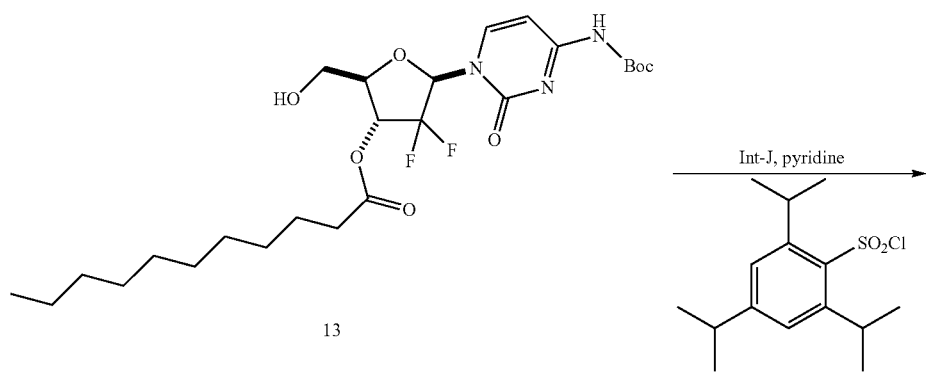
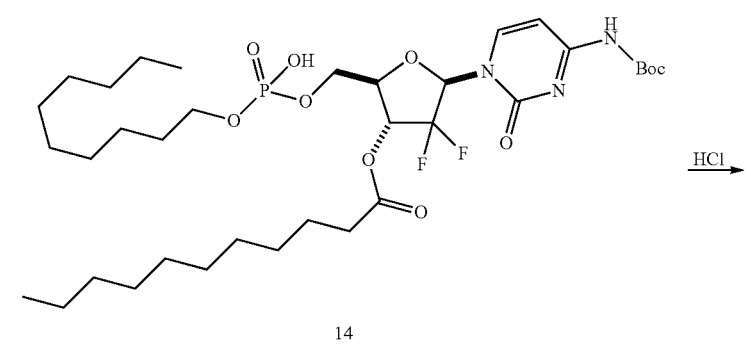

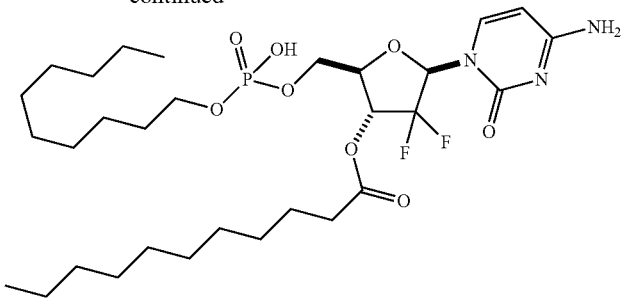

15

To a stirred solution of tert-butyl N-[1-[(2R,5R)-5-[[tert-butyl(dimethyl)silyl]oxymethyl]-3,3-difluoro-4-hydroxytetrahydrofuran-2-yl]-2-oxopyrimidin-4-yl]carbamate (5) (3.64 g, 7.6 mmol) in dry 1,4-dioxane (60 mL) was added undecanoic acid (4.71 g, 25.3 mmol), triethylamine (6.8 mL, 48.8 mmol), 1-(3-dimethylaminopropyl)-3-ethylcarbodiimide hydrochloride (4.39 g, 22.90 mmol) and 4-dimethylaminopyridine (91 mg, 0.7 mmol) while maintaining the temperature between 5-10° C. The reaction mixture was stirred at room temperature for 2 h. The reaction mixture was evaporated. The residue was partitioned between water (100 mL) and dichloromethane (150 mL) and the aqueous layer was extracted with dichloromethane (150 mL). The combined organic layers were washed with water (100 mL), dried over anhydrous magnesium sulfate, filtered and evaporated. The crude product was purified by silica gel column chromatography to give 12 (5.26 g) as a colorless oil.

To a stirred solution of 12 (5.2 g, 8.1 mmol) in distilled tetrahydrofuran (52 mL) was added triethylamine trihydrofluoride (7.6 mL, 46.6 mmol) at 0° C. under argon. The reaction mixture was stirred at room temperature for 18 h. The reaction mixture was evaporated. The residue was taken up in ethyl acetate (100 mL) and the organic layer was washed with saturated aqueous sodium bicarbonate (2×50 mL), water (50 mL), and brine (50 mL). The organic layer was dried over anhydrous magnesium sulfate and evaporated. The crude product was purified by silica gel column chromatography to give 13 (3.38 g, 83%) as a colorless oil.

A solution of 13 (540 mg, 2.3 mmol) in freshly distilled pyridine (17 mL) was stirred at 50° C. for 2 h under argon. The solution was evaporated and the residue was taken up in freshly distilled pyridine (8 mL). To the mixture was added 2,4,6-triisopropylbenzenesulfonyl chloride (1.37 g, 4.5 mmol) as a solution in freshly distilled pyridine (20 mL) and Int-J (1.20 g, 2.3 mmol) as a solution in freshly distilled pyridine (7 mL) at 40° C. under argon. The reaction mixture was stirred at 40° C. for 28 h. To the reaction mixture was added water (1.65 mL) and isopropanol (6.5 mL) and the mixture was stirred at room temperature for 15 min. The mixture was evaporated. To the residue was added toluene (10 mL) and the mixture was evaporated. This evaporation sequence was repeated 4 times. The crude product was purified by silica gel chromatography to give 14 (860 mg, 50%) as a white solid.

A suspension of 14 (1.18 g, 1.58 mmol) and hydrogen chloride (5.3 M in 1,4-dioxane, 11.6 mL, 61.48 mmol) was stirred at room temperature for 29 h under argon. The reaction mixture was evaporated and the residue was purified by preparative HPLC to give the title compound (15) (260 mg, 25%) as an off-white solid. $^1$H NMR (300 MHz, DMSO-$d_6$) δ 7.75-7.58 (m, 2H), 7.43-6.95 (m, 2H), 6.24 (t, J=9.1 Hz, 1H), 5.83 (d, J=7.6 Hz, 1H), 5.46-5.25 (m, 1H), 4.34-4.24 (m, 1H), 4.14-3.96 (m, 2H), 3.81-3.68 (m, 2H), 2.43 (t, J=7.4 Hz, 2H), 1.61-1.44 (m, 4H), 1.32-1.16 (m, 28H), 0.90-0.81 (m, 6H). LC-MS (ESI) m/z (M+H)$^+$: 652.2.

Example 16 (Compound 27) was synthesized in a similar manner as described in Example 15.

| Ex. No. | Compound No. | Structure | Chemical Name | LC-MS (ESI) m/z (M + H)$^+$ |
|---|---|---|---|---|
| 16 | 27 | 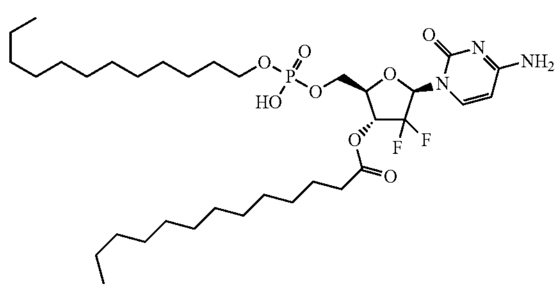 [SMILES: CCCCCCCCCCCCOP(=O)(O)OC[C@H]1O[C@@H](n2ccc(N)nc2=O)C(F)(F)[C@@H]1OC(=O)CCCCCCCCCCCC] | (2R,3R,5R)-5-(4-amino-2-oxopyrimidin-1(2H)-yl)-2-(((((dodecyloxy)(hydroxy)phosphoryl)oxy)methyl)-4,4-difluorotetrahydrofuran-3-yl tridecanoate | 708.3 |

Examples 17-21

The following compounds (Compounds 28-32) were synthesized in a similar manner as described in Example 2.

| Ex. No. | Compound No. | Structure | Chemical Name | LC-MS (ESI) m/z (M + H)+ |
|---|---|---|---|---|
| 17 | 28 | 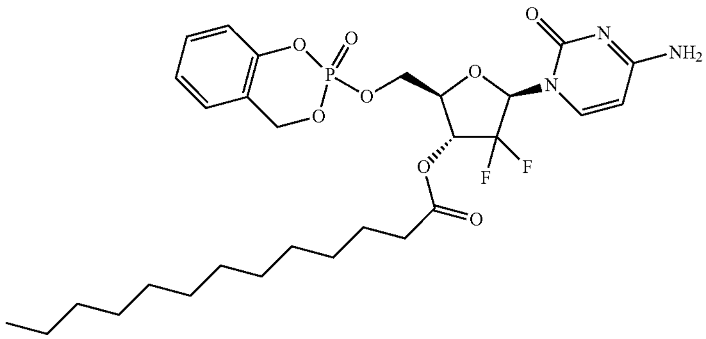 [SMILES: CCCCCCCCCCCCC(=O)O[C@@H]1[C@@H](COP2(=O)OCc3ccccc3O2)O[C@@H](n2ccc(N)nc2=O)C1(F)F] | (2R,3R,5R)-5-(4-amino-2-oxopyrimidin-1(2H)-yl)-4,4-difluoro-2-(((2-oxido-4H-benzo[d][1,3,2]dioxaphosphinin-2-yl)oxy)methyl)tetrahydrofuran-3-yl tridecanoate | 628.5 |
| 18 | 29 | 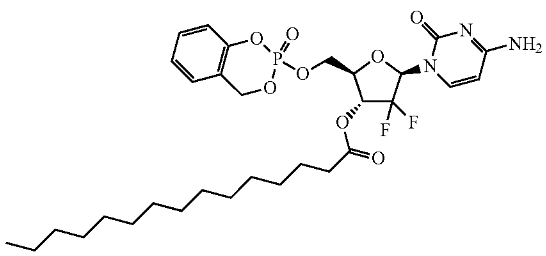 [SMILES: CCCCCCCCCCCCCCC(=O)O[C@@H]1[C@@H](COP2(=O)OCc3ccccc3O2)O[C@@H](n2ccc(N)nc2=O)C1(F)F] | (2R,3R,5R)-5-(4-amino-2-oxopyrimidin-1(2H)-yl)-4,4-difluoro-2-(((2-oxido-4H-benzo[d][1,3,2]dioxaphosphinin-2-yl)oxy)methyl)tetrahydrofuran-3-yl pentadecanoate | 654.6 |
| 19 | 30 | 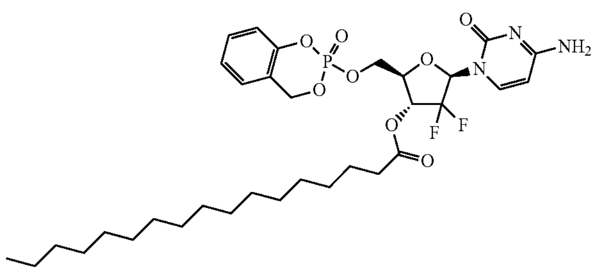 | (2R,3R,5R)-5-(4-amino-2-oxopyrimidin-1(2H)-yl)-4,4-difluoro-2-(((2-oxido-4H-benzo[d][1,3,2]dioxaphosphinin-2-yl)oxy)methyl)tetrahydrofuran-3-yl heptadecanoate | 682.6 |
| 20 | 31 | 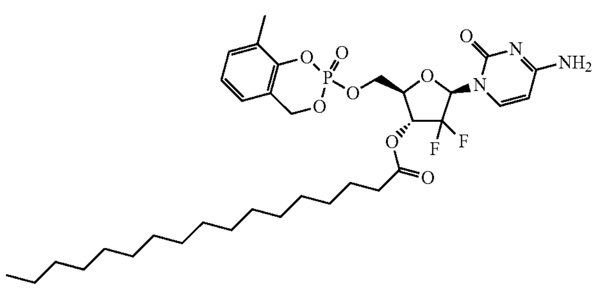 [SMILES: CCCCCCCCCCCCCCCCC(=O)O[C@@H]1[C@@H](COP2(=O)OCc3cccc(C)c3O2)O[C@@H](n2ccc(N)nc2=O)C1(F)F] | (2R,3R,5R)-5-(4-amino-2-oxopyrimidin-1(2H)-yl)-4,4-difluoro-2-(((8-methyl-2-oxido-4H-benzo[d][1,3,2]dioxaphosphinin-2-yl)oxy)methyl)tetrahydrofuran-3-yl heptadecanoate | 698.6 |
| 21 | 32 | 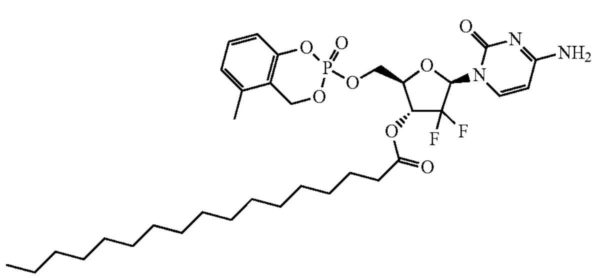 [SMILES: CCCCCCCCCCCCCCCCC(=O)O[C@@H]1[C@@H](COP2(=O)OCc3c(C)cccc3O2)O[C@@H](n2ccc(N)nc2=O)C1(F)F] | (2R,3R,5R)-5-(4-amino-2-oxopyrimidin-1(2H)-yl)-4,4-difluoro-2-(((5-methyl-2-oxido-4H-benzo[d][1,3,2]dioxaphosphinin-2-yl)oxy)methyl)tetrahydrofuran-3-yl heptadecanoate | 698.6 |

Examples 22-25

The following compounds (Compounds 33-36) were synthesized in a similar manner as described in Example 3.

| Ex. No. | Compound No. | Structure | LC-MS (ESI) m/z (M + H)+ |
|---|---|---|---|
| 22 | 33 | 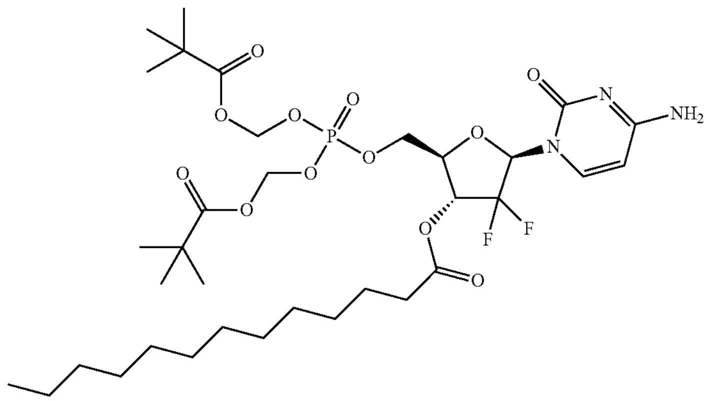 [SMILES: CCCCCCCCCCCCC(=O)O[C@@H]1[C@@H](COP(=O)(OCOC(=O)C(C)(C)C)OCOC(=O)C(C)(C)C)O[C@@H](n2ccc(N)nc2=O)C1(F)F] | 768.6 |
| 23 | 34 | 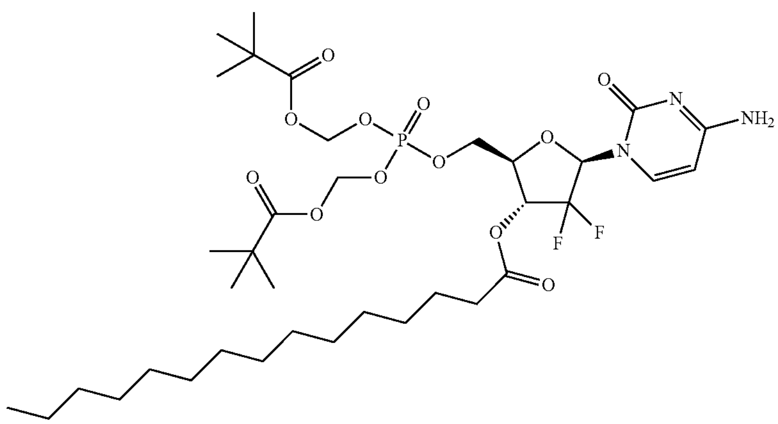 [SMILES: CCCCCCCCCCCCCCC(=O)O[C@@H]1[C@@H](COP(=O)(OCOC(=O)C(C)(C)C)OCOC(=O)C(C)(C)C)O[C@@H](n2ccc(N)nc2=O)C1(F)F] | 796.7 |
| 24 | 35 | 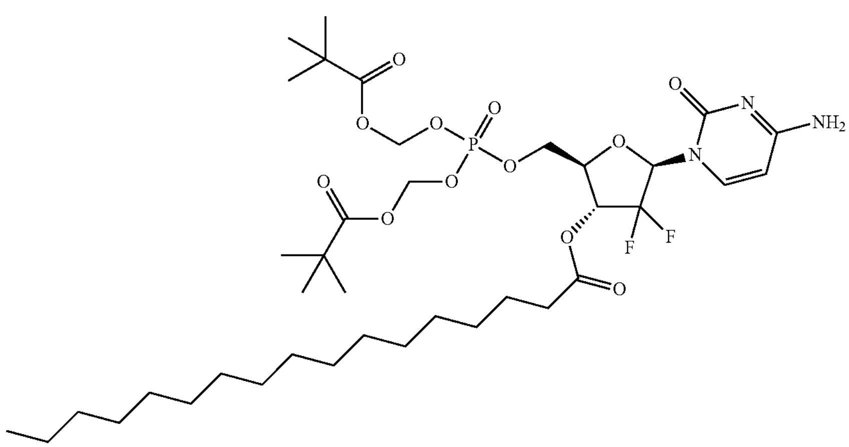 [SMILES: CCCCCCCCCCCCCCCCC(=O)O[C@@H]1[C@@H](COP(=O)(OCOC(=O)C(C)(C)C)OCOC(=O)C(C)(C)C)O[C@@H](n2ccc(N)nc2=O)C1(F)F] | 824.8 |

| Ex. No. | Compound No. | Structure | LC-MS (ESI) m/z (M + H)+ |
|---|---|---|---|
| 25 | 36 | 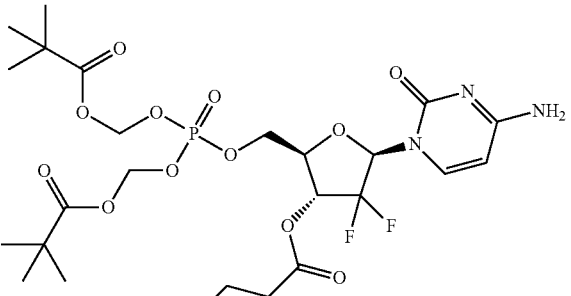 | 852.8 |
Example 26: Synthesis of Isomers 1-[(4aR,6R,7aR)-7,7-difluoro-2-octoxy-2-oxo-4,4a,6,7a-tetrahydrofuro[3,2-d][1,3,2]dioxaphosphinin-6-yl]-4-amino-pyrimidin-2-one (Compound 41A) and (Compound 41B)
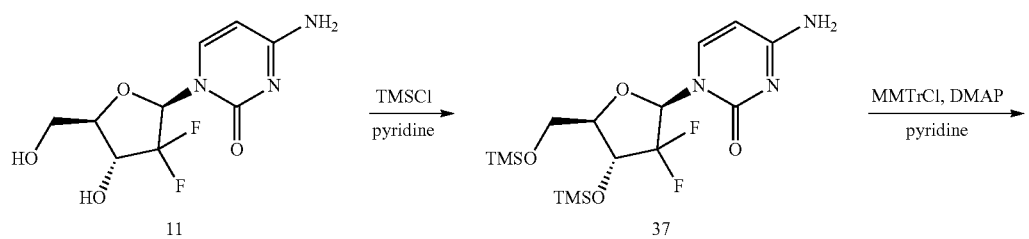
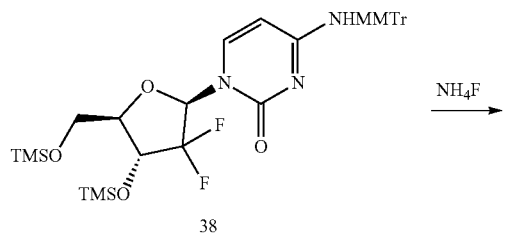
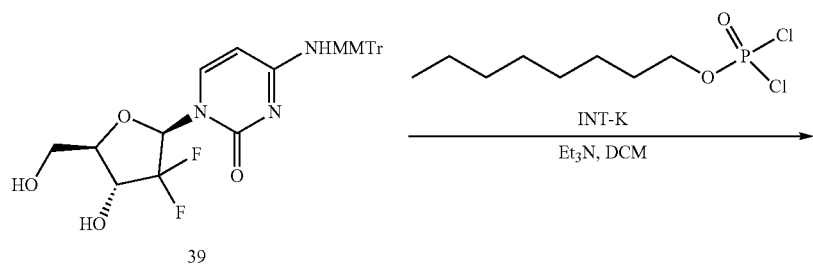

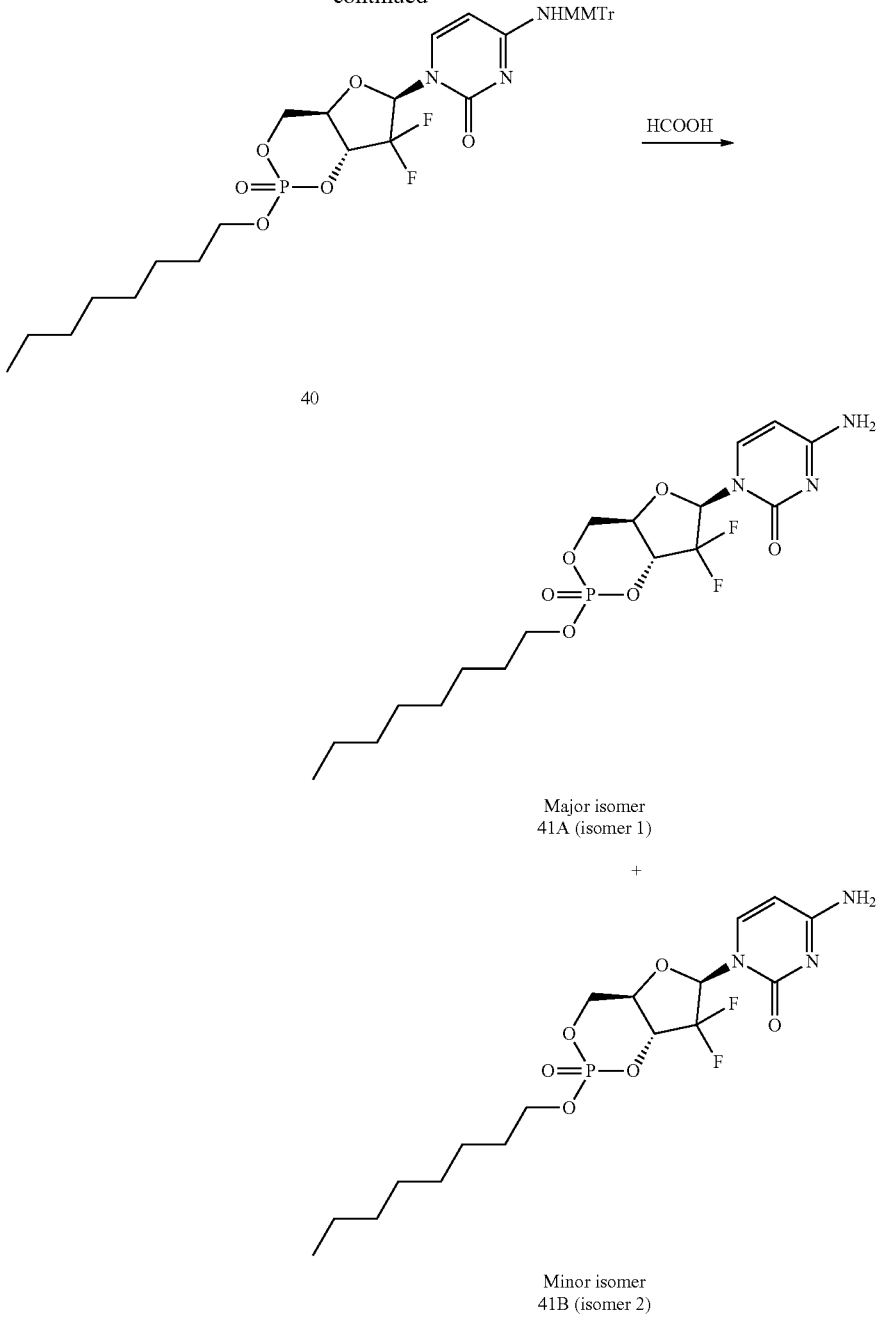

40

Major isomer
41A (isomer 1)

+

Minor isomer
41B (isomer 2)

4-amino-1-[(2R,4R,5R)-3,3-difluoro-4-hydroxy-5-(hydroxymethyl)tetrahydrofuran-2-yl]pyrimidin-2-one (20 g, 75.99 mmol, 1 eq.) was dissolved in pyridine (500 mL) and the mixture was cooled down to 0° C. TMSCl (49.53 g, 455.93 mmol, 6 eq.) was added and the mixture was stirred at 25° C. for 12 h. DMAP (9.28 g, 75.99 mmol, 1 eq.) and MMTrCl (46.93 g, 151.98 mmol, 2 eq.) were added and the reaction mixture was stirred at 50° C. for 16 h. The reaction mixture was quenched with cold sat.aq.NaHCO₃ slowly and extracted with EtOAc (500 mL×3). The organic layer was washed with brine (200 ml), dried over Na₂SO₄ and concentrated in vacuum. The crude product was combined with toluene (100 mL) and then concentrated again to yield 1-[(2R,4R,5R)-3,3-difluoro-4-trimethylsilyloxy-5-(trimethylsilyloxymethyl)tetrahydrofuran-2-yl]-4-[[(4-methoxyphenyl)-diphenyl-methyl]amino]pyrimidin-2-one (38) (103 g, crude, two parallel batches) as a yellow oil, which was used into the next step without further purification.

To a solution of 1-[(2R,4R,5R)-3,3-difluoro-4-trimethylsilyloxy-5-(trimethylsilyloxymethyl)tetrahydrofuran-2-yl]-4-[[(4-methoxyphenyl)-diphenyl-methyl]amino]pyrimidin-2-one (38) (103 g, 151.49 mmol, 1 eq.) in MeOH (1 L) was added NH₄F (28.05 g, 757.47 mmol, 5 eq.). The reaction mixture was stirred at 70° C. for 1 hr and then concentrated in vacuum. The residue was purified by column chromatography to yield 1-[(2R,4R,5R)-3,3-difluoro-4-hydroxy-5-(hydroxymethyl)tetrahydrofuran-2-yl]-4-[[(4-methoxyphenyl)-diphenylmethyl]amino]pyrimidin-2-one (39) (56 g, 69%) as a white solid. $^1$H-NMR (400 MHz, CDCl$_3$) δ 7.26-7.21 (m, 8H), 7.19-7.12 (m, 4H), 7.10-7.12 (m, 2H), 7.02-6.75 (m, 2H), 6.01 (s, 1H), 5.07 (m, 1H), 4.38-4.36 (m, 1H), 3.86-3.81 (m, 2H), 3.72 (s, 3H).

To a mixture of 1-[(2R,4R,5R)-3,3-difluoro-4-hydroxy-5-(hydroxymethyl)tetrahydrofuran-2-yl]-4-[[(4-methoxyphenyl)-diphenyl-methyl]amino]pyrimidin-2-one (39) (14.5 g, 27.08 mmol, 1 eq.) in DCM (300 mL) was added Et$_3$N (19.18 g, 189.53 mmol, 7 eq.). The reaction was cooled to −20° C., and then 1-dichlorophosphoryloxyoctane (Int-K) (13.38 g, 54.15 mmol, 2 eq.) was added dropwise over 10 min. The mixture was stirred at −20° C. for 0.5 h, and then 1-methylimidazole (8.89 g, 108.30 mmol, 4 eq.) was added dropwise over 15 min. The mixture was stirred at −15° C. for 1 h and then slowly warmed to 25° C. and stirred for 12 h. The mixture was concentrated and the residue was purified by column chromatography to yield 1-[(4aR,6R,7aR)-7,7-difluoro-2-octoxy-2-oxo-4,4a,6,7a-tetrahydrofuro[3,2-d][1,3,2]dioxaphosphinin-6-yl]-4-[[(4-methoxyphenyl)-diphenyl-methyl]amino]pyrimidin-2-one (40) (7.8 g, 41%) as a white solid. $^1$H-NMR (400 MHz, CDCl$_3$) δ 7.33-7.25 (m, 10H), 7.20-7.18 (m, 2H), 7.12-7.10 (m, 1H), 6.84-6.82 (m, 3H), 5.12-5.09 (m, 1H), 4.60-4.57 (m, 2H), 4.18-4.10 (m, 4H), 3.80 (s, 3H), 1.77-1.68 (m, 2H), 1.26-1.23 (m, 10H), 0.88-0.84 (m, 3H).

To a solution of 1-[(4aR,6R,7aR)-7,7-difluoro-2-octoxy-2-oxo-4,4a,6,7a-tetrahydrofuro[3,2-d][1,3,2]dioxaphosphinin-6-yl]-4-[[(4-methoxyphenyl)-diphenyl-methyl]amino] pyrimidin-2-one (40) (7.8 g, 10.99 mmol, 1 eq.) in water (20 mL) was added HCOOH (80 mL) and the mixture was stirred at 25° C. for 12 hrs. The mixture was concentrated in vacuum and the residue was purified by prep-HPLC to yield two stereoisomers (two stereoisomers at phosphorous) of 1-[(4aR,6R,7aR)-7,7-difluoro-2-octoxy-2-oxo-4,4a,6,7a-tetrahydrofuro[3,2-d][1,3,2]dioxaphosphinin-6-yl]-4-aminopyrimidin-2-one: major isomer (41A) (1.91 g, 39%) and minor isomer (41B) (1.55 g, 31%) as white solids. The stereochemistry at phosphorous was not assigned for Compounds 41A and 41B. Major isomer (41A): $^1$H-NMR (400 MHz, DMSO) δ 7.80 (s, 1H), 7.52 (d, 2H, J=11.6 Hz), 6.45 (s, 1H), 5.81 (d, 1H, J=7.6 Hz), 4.95 (s, 1H), 4.75-4.71 (m, 2H), 4.28 (s, 1H), 4.15-4.09 (s, 2H), 1.76-1.66 (m, 2H), 1.37-1.35 (m, 2H), 1.27-1.26 (m, 8H), 0.87-0.84 (m, 3H). QC (ESI+): 438.16 (M+H). Minor isomer (41B): $^1$H-NMR (400 MHz, DMSO) δ 7.80 (s, 1H), 7.53 (d, 2H, J=6.8 Hz), 6.45 (s, 1H), 5.80 (d, 1H, J=8.0 Hz), 5.30 (s, 1H), 4.76-4.64 (m, 2H), 4.38 (s, 1H), 4.13-4.08 (s, 2H), 1.65-1.60 (m, 2H), 1.32-1.26 (m, 10H), 0.88-0.85 (m, 3H). QC (ESI+): 438.16 (M+H).

Examples 27-31

The following compounds (Compounds 42A, 42B, 43A, 43B, 44A, 44B, 45A, 45B, 46A, and 46B) were synthesized in a similar manner as described in Example 26. As in Example 26, the stereochemistry at phosphorous was not assigned for the compounds of Examples 27-31.

| Ex. No. | Compd. No. | Structure | Chemical Name | LC-MS (ESI) m/z (M + H)$^+$ |
|---|---|---|---|---|
| 27 | 42A (isomer 1) | 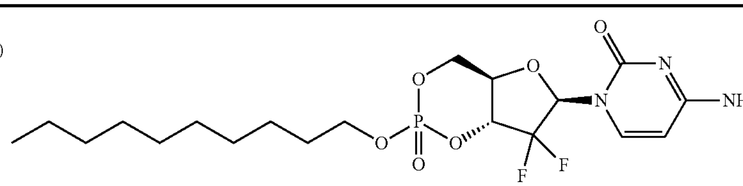 | 4-amino-1-((4aR,6R,7aR)-2-(decyloxy)-7,7-difluoro-2-oxidotetrahydro-4H-furo[3,2-d][1,3,2]dioxaphosphinin-6-yl)pyrimidin-2(1H)-one | 466.2 |
| | 42B (isomer 2) | | 4-amino-1-((4aR,6R,7aR)-2-(decyloxy)-7,7-difluoro-2-oxidotetrahydro-4H-furo[3,2-d][1,3,2]dioxaphosphinin-6-yl)pyrimidin-2(1H)-one | 466.2 |
| 28 | 43A (isomer 1) | 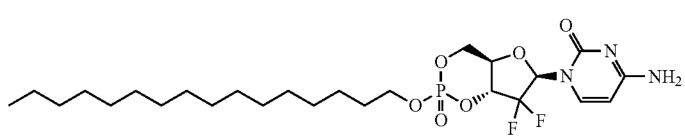 | 4-amino-1-((4aR,6R,7aR)-7,7-difluoro-2-(hexadecyloxy)-2-oxidotetrahydro-4H-furo[3,2-d][1,3,2]dioxaphosphinin-6-yl)pyrimidin-2(1H)-one | 550.3 |
| | 43b (isomer 2) | | 4-amino-1-((4aR,6R,7aR)-7,7-difluoro-2-(hexadecyloxy)-2-oxidotetrahydro-4H-furo[3,2-d][1,3,2]dioxaphosphinin-6-yl)pyrimidin-2(1H)-one | 550.3 |

-continued

| Ex. No. | Compd. No. | Structure | Chemical Name | LC-MS (ESI) m/z (M + H)+ |
|---|---|---|---|---|
| 29 | 44A (isomer 1) | 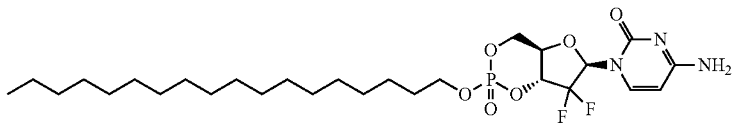 | 4-amino-1-((4aR,6R,7aR)-7,7-difluoro-2-(octadecyloxy)-2-oxidotetrahydro-4H-furo[3,2-d][1,3,2]dioxaphosphinin-6-yl)pyrimidin-2(1H)-one | 578.3 |
| | 44B (isomer 2) | | 4-amino-1-((4aR,6R,7aR)-7,7-difluoro-2-(octadecyloxy)-2-oxidotetrahydro-4H-furo[3,2-d][1,3,2]dioxaphosphinin-6-yl)pyrimidin-2(1H)-one | 578.3 |
| 30 | 45A (isomer 1) | 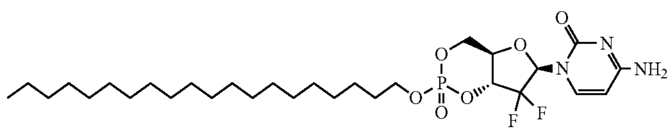 | 4-amino-1-((4aR,6R,7aR)-7,7-difluoro-2-(icosyloxy)-2-oxidotetrahydro-4H-furo[3,2-d][1,3,2]dioxaphosphinin-6-yl)pyrimidin-2(1H)-one | 606.3 |
| | 45B (isomer 2) | | 4-amino-1-((4aR,6R,7aR)-7,7-difluoro-2-(icosyloxy)-2-oxidotetrahydro-4H-furo[3,2-d][1,3,2]dioxaphosphinin-6-yl)pyrimidin-2(1H)-one | 606.3 |
| 31 | 46A (isomer 1) | 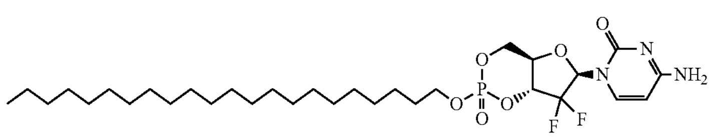 | 4-amino-1-((4aR,6R,7aR)-2-(docosyloxy)-7,7-difluoro-2-oxidotetrahydro-4H-furo[3,2-d][1,3,2]dioxaphosphinin-6-yl)pyrimidin-2(1H)-one | 634.4 |
| | 46B (isomer 2) | | 4-amino-1-((4aR,6R,7aR)-2-(docosyloxy)-7,7-difluoro-2-oxidotetrahydro-4H-furo[3,2-d][1,3,2]dioxaphosphinin-6-yl)pyrimidin-2(1H)-one | 634.4 |

Examples 32-35

The following compounds are synthesized in a similar manner as described in Example 3.

| Ex. No. | Structure |
|---|---|
| 32 | 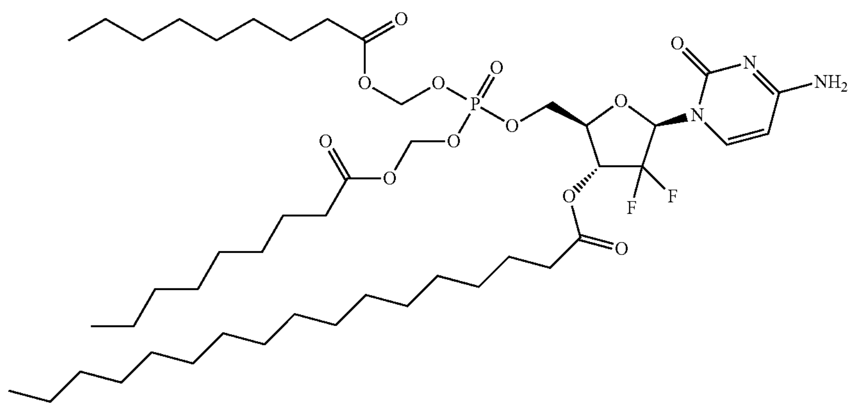 [SMILES: CCCCCCCCCCCCCCCCC(=O)O[C@@H]1[C@@H](COP(=O)(OCOC(=O)CCCCCCCC)OCOC(=O)CCCCCCCC)O[C@@H](n2ccc(N)nc2=O)C1(F)F] |
| 33 | 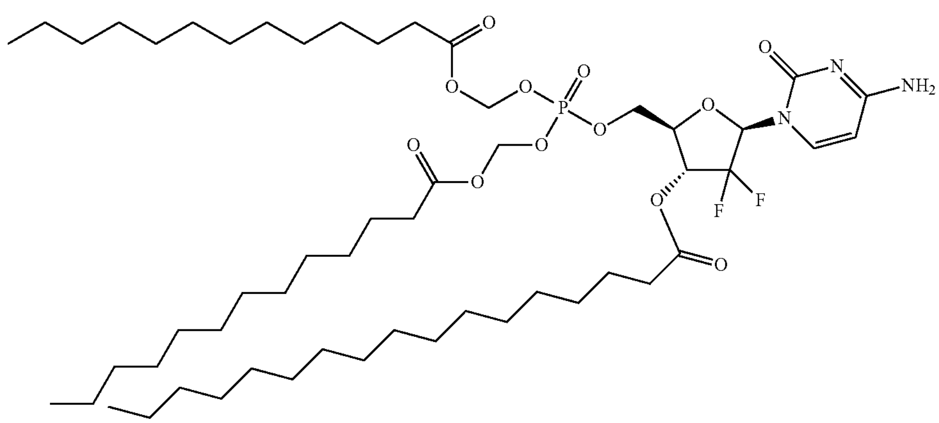 [SMILES: CCCCCCCCCCCCCCCCC(=O)O[C@@H]1[C@@H](COP(=O)(OCOC(=O)CCCCCCCCCCCC)OCOC(=O)CCCCCCCCCCCC)O[C@@H](n2ccc(N)nc2=O)C1(F)F] |
| 34 | 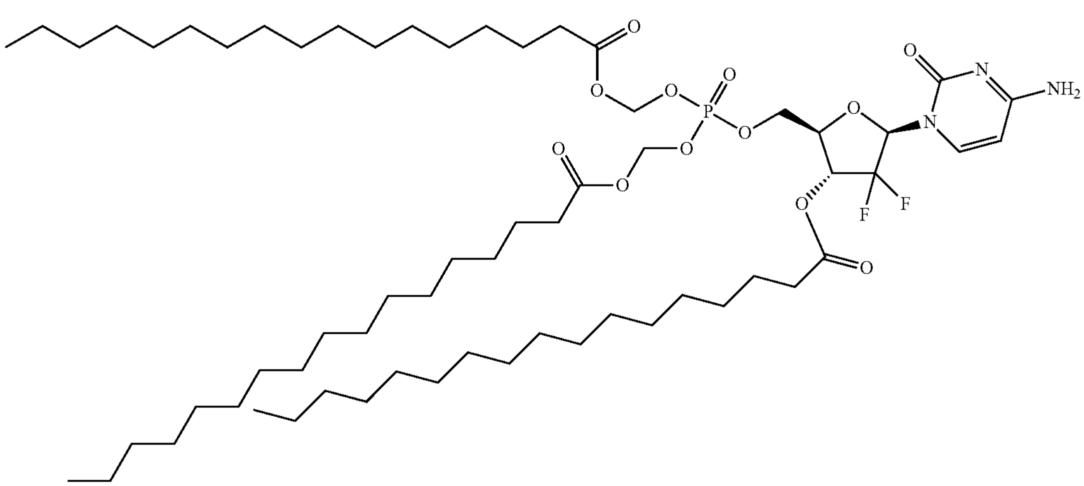 [SMILES: CCCCCCCCCCCCCCCCC(=O)OCOP(=O)(OCOC(=O)CCCCCCCCCCCCCCCC)OC[C@H]1O[C@@H](n2ccc(N)nc2=O)C(F)(F)[C@@H]1OC(=O)CCCCCCCCCCCCCCCC] |

| Ex. No. | Structure |
|---|---|
| 35 | 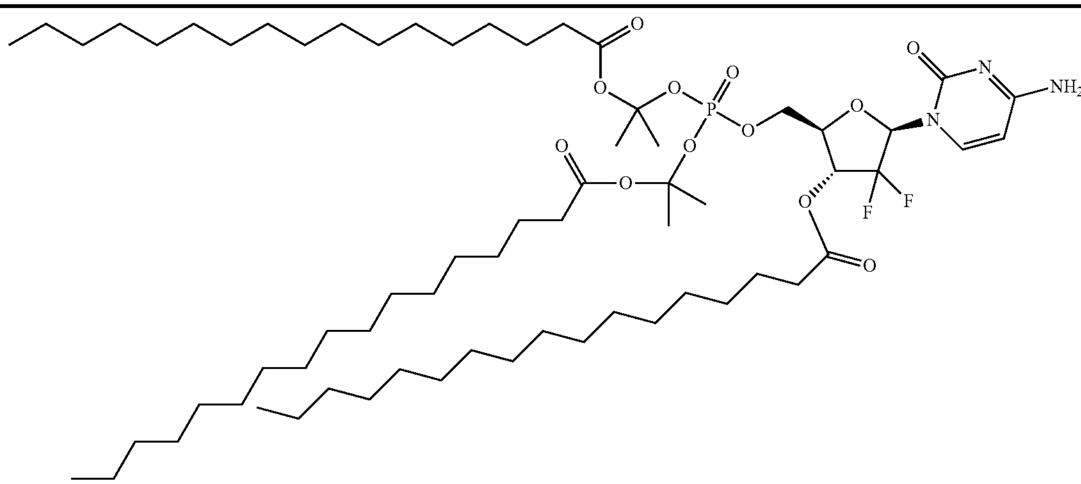 |

Cellular Pharmacology

Compounds are tested for their ability to impair cancer cell proliferation and/or induce cell death. For cellular proliferation studies, cultured cells are treated with the test compound for 24-120 hours. After compound treatment, cell proliferation is assessed by using methods including, but not limited to, Cell-Titer-Glo® (Promega), Alamar Blue, LIVE/DEAD® (ThermoFisher), BrdU incorporation, and live-cell imaging.

The cancer lines used include, but are not limited to, PANC-1, MiaPaCa-2, BxPC-3 (pancreatic cancer), RT112 (bladder cancer), MCF-7 (breast cancer), and A549 (non-small cell lung cancer). Gemcitabine Hydrochloride serves as a control for activity.

Protocol for the Cellular Proliferation Assay in BxPC-3 Cells

BxPC-3 (pancreatic adenocarcinoma) cell line was purchased from the American Type Culture Collection (Catalog #CRL-1687) and grown in RPMI-1640 medium (e.g. Corning #10-040-CV) with 10% Heat Inactivated Fetal Calf Serum at 37° C. and 5% CO2 (as recommended by the ATCC).

Cultures were grown in 175 mm² plates to 80% confluence, and cells were trypsinized to a single-cell suspension. Cells were then resuspended in growth medium to a density of 25,00 cells/ml. They were then plated into 96-well assay plates (Corning #3917) in a volume of 100 ul/well (2,500 cells/well). Cells were allowed to adhere to plates for 24 h at 37° C. and 5% $CO_2$). Compounds were then added to the wells using an 11-fold serial dilution scheme (over 9 dilutions, generally ranging from 30 µM-30 pM), and the cells were incubated for an additional 120 hours. After 120 h, 90 ul of Cell-Titer Glo reagent (Promega #G7572) was added, and the plates were read using a luminescence counter (e.g., BioTek Synergy HTX at 100 ms read time).

Potency determination were performed by 4-parameter fit of the dose vs. luminescence data using XLFit software (IDBS) with a one site dose response model (Model 205; fit=(A+((B−A)/(1+((C/x)^D)))). The $EC_{50}$ was generally expressed as the inflection point (C parameter) for the fit when the upper and lower portions of the response curve were well-defined. In cases where full inhibition of cell growth was not observed at the highest concentration used, $EC_{50}$ was reported as the concentration that resulted in 50% loss of Cell-Titer-Glo signal (compared to untreated control).

Potency of compounds in BxPC-3 cells is shown in Table 1:

TABLE 1

| Compound | $EC_{50}$ |
|---|---|
| Gemcitabine Hydrochloride | +++ |
| 1 | +++ |
| 2 | ++++ |
| 3 | ++++ |
| 16 | ++ |
| 17 | + |
| 18 | ++ |
| 19 | ++ |
| 20 | + |
| 21 | + |
| 22 | + |
| 23 | + |
| 24 | + |
| 25 | + |
| 28 | ++++ |
| 29 | ++++ |
| 30 | ++++ |
| 31 | ++++ |
| 32 | ++++ |
| 33 | ++++ |
| 34 | ++++ |
| 35 | ++++ |
| 36 | ++++ |
| 42A | ++++ |
| 43A | +++ |
| 44A | +++ |
| 45A | ++ |
| 46A | + |

++++ = $EC_{50}$ < 1 nM;
+++ = 1 nM ≤ $EC_{50}$ < 100 nM;
++ = nM ≤ $EC_{50}$ < 1 µM;
+ = 1 µM ≤ $EC_{50}$ < 25 µM

Animal Pharmacology

Compounds are tested to impair tumor growth in rodents using several "xenograft" model systems. Initially, immune-deficient (e.g. SCID) mice are implanted subcutaneously with tumor cells (using either tumor cell lines or human patient-derived tumor tissue) until tumors are palpable (~100-200 mm³). Test article is administered intravenously at varying doses and schedules, and anti-tumor effect is determined by physical measurement of tumors using standard methods (i.e., caliper measurements). Additional measures of anti-tumor effect include time of survival, gain/loss of body weight, non-invasive visualization of tumor mass (i.e., ultrasound, positron emission tomography, optical imaging), or direct visualization of tumor growth/metastasis by necropsy.

In addition to the aforementioned xenograft models, a variety of genetically-engineered mouse models (GEMINI) of cancer are employed. In these models, GEMM mice are allowed to spontaneously grow tumors, at which time test article administration is initiated. Determination of anti-tumor effect is implemented by caliper measurement of lesions, time of survival, gain/loss of body weight, non-invasive visualization of tumor mass (i.e., ultrasound, positron emission tomography, optical imaging), or direct visualization of tumor growth/metastasis by necropsy.

In both types of models, gemcitabine hydrochloride is used as a comparator. Additionally, other common antineoplastic compounds (e.g., paclitaxel, 5-fluorouracil, erlotinib etc.) are used as control compounds depending on the tumor type being studied.

Additional Measurements

In addition to the functional assays described above, a series of cell- and animal-based experiments are performed to determine the uptake (i.e., in tumor vs. normal tissue) and catabolism/metabolism of test compounds. For instance, test compounds are applied to cells growing in culture for varying amounts of time. Subsequently, cells (and media) are collected and analyzed to determine the concentration of parent compound and metabolites.

For example, compounds were evaluated for the liberation of gemcitabine in both human liver microsomes and human hepatocytes.

Protocol for metabolic stability in human liver microsomes:
[Compound]=1 µM
[LM]=0.5 mg/mL
[NADPH]=0 or 1 mM
Buffer=100 mM Potassium Phosphate, pH 7.4
Time=0, 15, 30, and 60 min
Temperature=37° C.

Liver microsomes tissue fractions were used for in vitro assessment of metabolic stability of various compounds by cytochrome P450 (CYP450) mediated phase I oxidation, and metabolism through other pathways. Human liver microsomes tissue fractions were obtained from Corning Gentest.

The assay is carried out in 96-well microtiter plates. Compounds were incubated at 37° C. in the presence of human liver microsomes. Reaction mixtures (25 µL) contain a final concentration of 1 µM test compound, 0.5 mg/mL liver microsomes protein, and 1 mM NADPH in 100 mM potassium phosphate, pH 7.4 buffer. At each of the time points (0, 15, 30, and 60 minutes), 150 µL of quench solution (100% acetonitrile with 0.1% formic acid) with internal standard bucetin was transferred to each well. Verapamil was included as a positive control to verify assay performance. The extent of metabolism is determined as the formation of the drug gemcitabine. Plates were sealed and centrifuged at 4° C. for 15 minutes at 4000 rpm. The supernatant was transferred to fresh plates for LC/MS/MS analysis.

All samples were analyzed on LC/MS/MS using an AB Sciex API 4000 instrument, coupled to a Shimadzu LC-20AD LC Pump system. Analytical samples were separated using a Waters Atlantis T3 dC18 reverse phase HPLC column (50 mm×2.1 mm, 3 um) at a flow rate of 0.3 mL/min. The mobile phase consisted of 0.1% formic acid in water (solvent A) and 0.1% formic acid in 100% acetonitrile (solvent B).

Results:

| Compound | Relative Peak Area Ratio (gemcitabine/internal standard) | | | |
|---|---|---|---|---|
| | 0 min | 15 min | 30 min | 60 min |
| 1 | 7.7 | 15.1 | 12.7 | 18.1 |
| 2 | 10.0 | 17.8 | 17.4 | 47.5 |
| 3 | 0.0 | 0.0 | 0.0 | 8.3 |
| 21 | 0.0 | 0.0 | 0.0 | 1.9 |
| 24 | 0.0 | 0.0 | 0.0 | 0.0 |
| 28 | 0.0 | 14.8 | 18.7 | 58.1 |
| 30 | 0.0 | 4.9 | 8.2 | 25.5 |
| 31 | 0.0 | 1.6 | 6.5 | 23.7 |
| 33 | 0.0 | 21.1 | 19.7 | 26.0 |
| 35 | 0.0 | 0.0 | 1.6 | 6.3 |
| 42A | 0.0 | 0.0 | 4.2 | 7.4 |
| 43A | 0.0 | 0.0 | 0.0 | 9.7 |

Protocol for metabolic stability in human hepatocytes:
[Compound]=1
[Hepatocytes]=0.5 million cells/mL
Time=0, 60, 120, and 180 min
Temperature=37° C.

Metabolic stability of testing compound was evaluated using human hepatocytes to determine the formation of gemcitabine. Human LiverPool™ 20-donor cryopreserved hepatocytes are obtained from BioIVT.

Cryopreserved hepatocytes were removed from the liquid nitrogen tank and thawed in a 37° C. water bath. As soon as the cells pull away from the vial wall, they were decanted into 48 mL of warm HT medium. Cells were centrifuged for four minutes at 420 rpm (50 g). After removing the supernatant, pellet was re-suspended in warm DMEM medium. Cell density was counted by a hemacytometer.

The assay was carried out in 96-well microtiter plates. Compounds were incubated for 0, 60, 120, and 180 minutes at 37° C. with hepatocytes. Reaction mixtures (50 µL) contained a final concentration of 1 test compound, 0.5 million cells/mL hepatocytes in the DMEM medium. At each of the time points (0, 1, 2, and 3 hours), 150 µL of quench solution (100% acetonitrile with 0.1% formic acid) with internal standard bucetin was transferred to each well. Midazolam was included as a positive control to verify assay performance. The extent of metabolism was determined as the formation of the drug gemcitabine. Plates were sealed and centrifuged at 4° C. for 15 minutes at 4000 rpm. The supernatant was transferred to fresh plates for LC/MS/MS analysis.

All samples were analyzed on LC/MS/MS using an AB Sciex API 4000 instrument, coupled to a Shimadzu LC-20AD LC Pump system. Analytical samples were separated using a Waters Atlantis T3 dC18 reverse phase HPLC column (50 mm×2.1 mm, 3 um) at a flow rate of 0.3 mL/min. The mobile phase consisted of 0.1% formic acid in water (solvent A) and 0.1% formic acid in 100% acetonitrile (solvent B).

| Relative Peak Area Ratio (gemcitabine/internal standard) | | | | |
|---|---|---|---|---|
| Compound | 0 min | 15 min | 30 min | 60 min |
| 1 | 0.0 | 0.0 | 0.0 | 2.4 |
| 2 | 0.0 | 55.6 | 58.8 | 49.2 |
| 3 | 0.0 | 54.7 | 55.8 | 47.1 |
| 21 | 0.0 | 0.0 | 0.0 | 0.0 |
| 24 | 0.0 | 0.0 | 0.0 | 0.0 |
| 28 | 0.0 | 41.4 | 54.8 | 42.3 |
| 30 | 0.0 | 0.0 | 0.0 | 6.4 |
| 31 | 0.0 | 0.0 | 7.5 | 6.3 |
| 33 | 0.0 | 18.3 | 24.2 | 23.8 |
| 35 | 0.0 | 0.0 | 0.0 | 0.0 |
| 42A | 0.0 | 0.0 | 3.7 | 8.6 |
| 43A | 0.0 | 0.0 | 0.0 | 0.0 |

Other experiments are performed in tumor-bearing animals to determine the distribution of test article as well as active (and inactive) metabolites in blood, normal tissue, and tumor.

What is claimed is:

1. A compound having the structure of Formula (II):

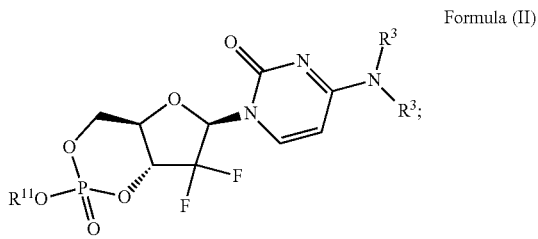

Formula (II)

wherein:
$R^3$ is H, —C(O)$R^9$, or —C(O)O$R^9$;
$R^4$ is H;
$R^9$ is $C_{1-8}$alkyl;
$R^{11}$ is $C_{6-22}$alkyl, $C_{3-22}$alkenyl, $C_{3-22}$alkynyl, $C_{3-22}$haloalkyl, —$C_{1-4}$alkyl-OC(O)$C_{1-8}$alkyl, $C_{6-10}$aryl, —$C_{1-8}$alkyl-$C_{6-10}$aryl, $C_{2-9}$heteroaryl, or —$C_{1-8}$alkyl-$C_{2-9}$heteroaryl, wherein $C_{6-10}$aryl, —$C_{1-8}$alkyl-$C_{6-10}$aryl, $C_{2-9}$heteroaryl, or —$C_{1-8}$alkyl-$C_{2-9}$heteroaryl are optionally substituted with 1, 2, 3, or 4 $R^{12}$;
each $R^{12}$ is independently selected from halogen, $C_{1-8}$alkyl, $C_{1-8}$haloalkyl, $C_{1-8}$alkoxy, and —C(O)$R^{13}$; and
each $R^{13}$ is independently selected from $C_{1-12}$alkyl;
or a pharmaceutically acceptable salt thereof.

2. The compound of claim 1, or a pharmaceutically acceptable salt thereof, wherein $R^{11}$ is $C_{6-22}$alkyl.

3. The compound of claim 1, or a pharmaceutically acceptable salt thereof, wherein $R^{11}$ is $C_{16-22}$alkyl.

4. The compound of claim 1, or a pharmaceutically acceptable salt thereof, wherein $R^{11}$ is —$C_{1-4}$alkyl-OC(O)$C_{1-8}$alkyl.

5. The compound of claim 4, or a pharmaceutically acceptable salt thereof, wherein $R^{11}$ is —$C_{1-2}$alkyl-OC(O)$C_{1-6}$alkyl.

6. The compound of claim 5, or a pharmaceutically acceptable salt thereof, wherein $R^{11}$ is —$CH_2$—OC(O)C($CH_3$)$_3$.

7. The compound of claim 1, or a pharmaceutically acceptable salt thereof, wherein $R^{11}$ is phenyl optionally substituted with 1, 2, or 3 $R^{12}$.

8. The compound of claim 7, or a pharmaceutically acceptable salt thereof, wherein $R^{11}$ is phenyl optionally substituted with 1, 2, or 3 $R^{12}$, and each $R^{12}$ is independently selected from $C_{1-8}$alkyl, $C_{1-8}$alkoxy, and —C(O)$R^{13}$.

9. The compound of claim 8, or a pharmaceutically acceptable salt thereof, wherein $R^{11}$ is phenyl optionally substituted with 1 or 2 $R^{12}$, and each $R^{12}$ is independently selected from $C_{1-8}$alkyl and $C_{1-8}$alkoxy.

10. The compound of claim 1, or a pharmaceutically acceptable salt thereof, wherein $R^{11}$ is —$C_{1-8}$alkyl-$C_{6-10}$aryl optionally substituted with 1, 2, 3, or 4 $R^{12}$.

11. The compound of claim 10, or a pharmaceutically acceptable salt thereof, wherein $R^{11}$ is —$CH_2$-phenyl optionally substituted with 1, 2, or 3 $R^{12}$.

12. The compound of claim 11, or a pharmaceutically acceptable salt thereof, wherein $R^{11}$ is —$CH_2$-phenyl optionally substituted with 1, 2, or 3 $R^{12}$, and each $R^{12}$ is independently selected from $C_{1-8}$alkyl, $C_{1-8}$alkoxy, and —C(O)$R^{13}$.

13. The compound of claim 12, or a pharmaceutically acceptable salt thereof, wherein $R^{11}$ is —$CH_2$-phenyl optionally substituted with 1 or 2 $R^{12}$, and each $R^{12}$ is independently selected from $C_{1-8}$alkyl and $C_{1-8}$alkoxy.

14. The compound of claim 1, or a pharmaceutically acceptable salt thereof, wherein $R^3$ is H.

15. The compound of claim 1, or a pharmaceutically acceptable salt thereof, wherein $R^3$ is —C(O)$R^9$.

16. The compound of claim 1, or a pharmaceutically acceptable salt thereof, wherein $R^3$ is —C(O)O$R^9$.

17. The compound of claim 1 selected from:

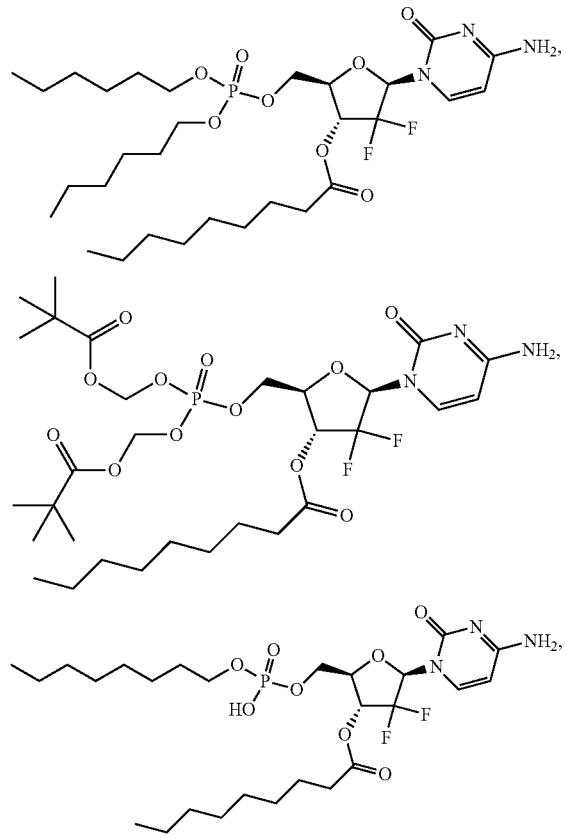

133
-continued
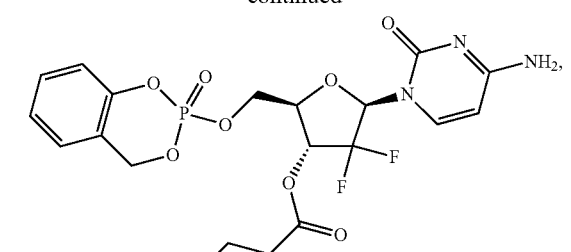
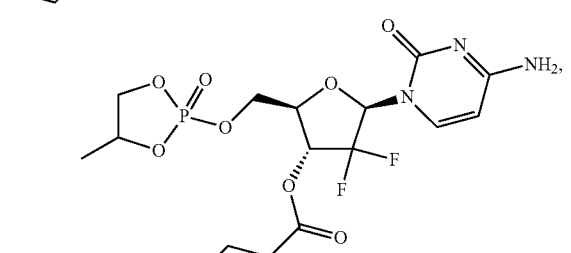
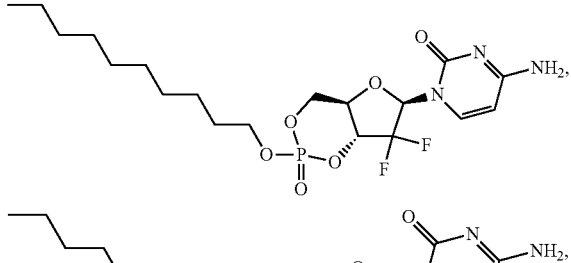
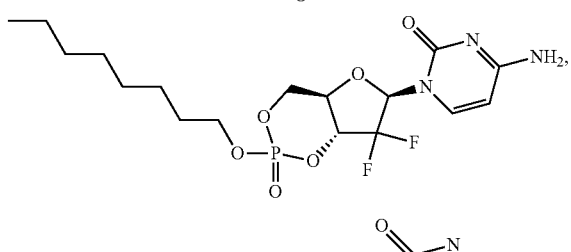
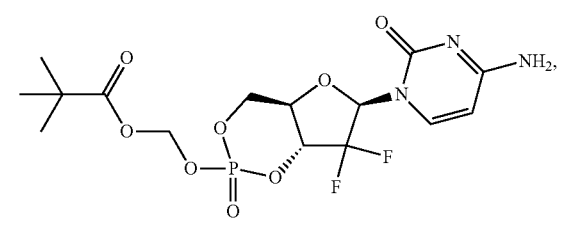
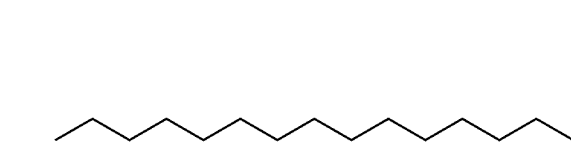
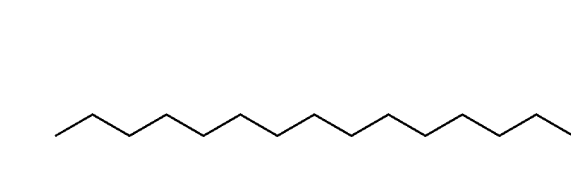
134
-continued
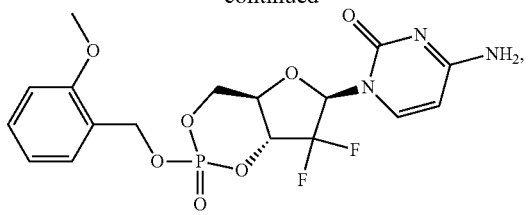
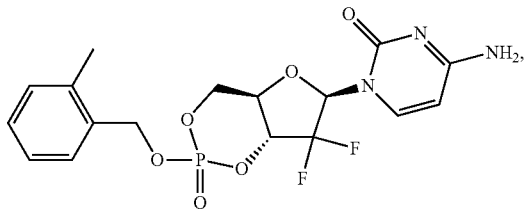
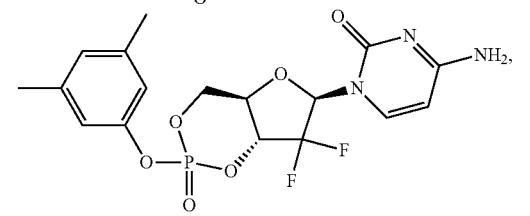
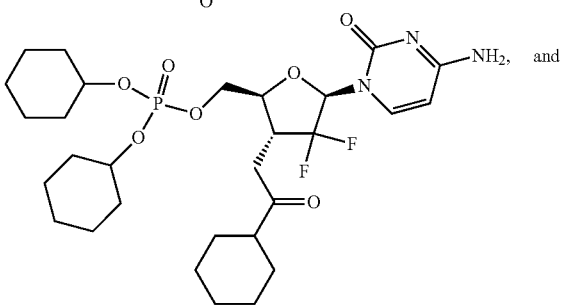 and
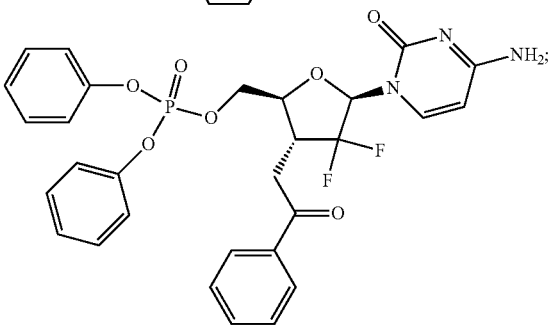
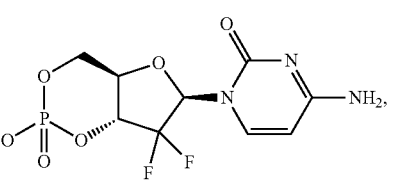
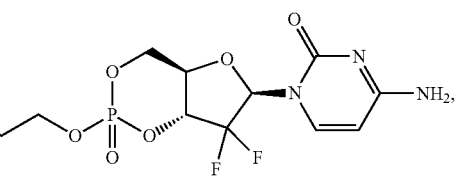

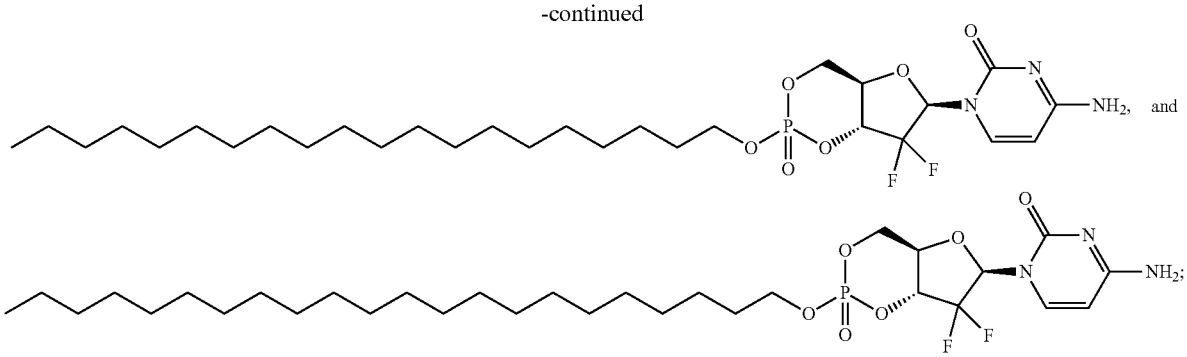

or a pharmaceutically acceptable salt thereof.

18. A pharmaceutical composition comprising a compound of claim 1, or a pharmaceutically acceptable salt thereof, and at least one pharmaceutically acceptable excipient.

19. A method of treating cancer in a patient in need thereof, comprising administering to the patient a therapeutically effective amount of a compound of claim 1, or a pharmaceutically acceptable salt thereof, wherein the cancer is selected from pancreatic cancer, bladder cancer, breast cancer, and non-small cell lung cancer.

* * * * *